(12) United States Patent
Webber et al.

(10) Patent No.: US 7,560,544 B2
(45) Date of Patent: Jul. 14, 2009

(54) 3,5-DISUBSITITUTED AND 3,5,7-TRISUBSTITUTED-3H-OXAZOLO AND 3H-THIAZOLO[4,5-D]PYRIMIDIN-2-ONE COMPOUNDS AND PRODRUGS THEREOF

(75) Inventors: Stephen E. Webber, San Diego, CA (US); Gregory J. Haley, Del Mar, CA (US); Joseph R. Lennox, San Diego, CA (US); Alan X. Xiang, San Diego, CA (US); Erik J. Rueden, Santee, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 119 days.

(21) Appl. No.: 11/304,691

(22) Filed: Dec. 16, 2005

(65) Prior Publication Data

US 2006/0160830 A1   Jul. 20, 2006

Related U.S. Application Data

(60) Provisional application No. 60/636,633, filed on Dec. 17, 2004, provisional application No. 60/636,634, filed on Dec. 17, 2004.

(51) Int. Cl.
C07H 19/00 (2006.01)
A01N 43/04 (2006.01)
A61K 31/70 (2006.01)

(52) U.S. Cl. .................................. 536/27.2; 514/45
(58) Field of Classification Search ........................ None
See application file for complete search history.

(56) References Cited

U.S. PATENT DOCUMENTS

| | | | |
|---|---|---|---|
| 4,539,205 A | 9/1985 | Goodman et al. | |
| 4,643,992 A | 2/1987 | Goodman et al. | |
| 4,746,651 A | 5/1988 | Goodman | |
| 4,880,784 A | 11/1989 | Robins et al. | |
| 5,011,828 A | 4/1991 | Goodman et al. | |
| 5,041,426 A | 8/1991 | Robins et al. | |
| 5,041,542 A | 8/1991 | Robins et al. | |
| 5,166,141 A * | 11/1992 | Goodman et al. | .............. 514/45 |
| 5,248,672 A | 9/1993 | Townsend et al. | |
| 5,395,937 A | 3/1995 | Nikolaides et al. | |
| 5,424,295 A | 6/1995 | Krenitsky et al. | |
| 5,446,045 A | 8/1995 | Revankar et al. | |
| 5,492,897 A | 2/1996 | Krenitsky et al. | |
| 5,821,236 A | 10/1998 | Krenitsky et al. | |
| 5,994,321 A | 11/1999 | Lewis et al. | |
| 6,028,076 A | 2/2000 | Hirota et al. | |
| 6,329,381 B1 | 12/2001 | Kurimoto et al. | |
| 6,376,501 B1 | 4/2002 | Isobe et al. | |
| 6,479,463 B1 | 11/2002 | Wang et al. | |
| 6,509,320 B1 | 1/2003 | Wang et al. | |
| 6,566,344 B1 | 5/2003 | Gosselin et al. | |
| 2002/0058635 A1 | 5/2002 | Averett | |
| 2002/0173655 A1 | 11/2002 | Dellaria et al. | |
| 2003/0065005 A1 | 4/2003 | Charles et al. | |
| 2003/0100764 A1 | 5/2003 | Bonk et al. | |
| 2003/0162806 A1 | 8/2003 | Dellaria et al. | |
| 2003/0176458 A1 | 9/2003 | Dellaria et al. | |
| 2003/0186949 A1 | 10/2003 | Dellaria et al. | |
| 2003/0195209 A1 | 10/2003 | Dellaria et al. | |
| 2003/0199461 A1 | 10/2003 | Averett et al. | |
| 2004/0063658 A1 | 4/2004 | Roberts et al. | |
| 2005/0004144 A1 | 1/2005 | Carson et al. | |

FOREIGN PATENT DOCUMENTS

| | | |
|---|---|---|
| EP | 0 882 727 | 9/1998 |
| EP | 1 035 123 | 9/2000 |
| EP | 1 043 021 | 10/2000 |
| EP | 1 386 923 A1 | 2/2004 |
| WO | WO-89/05649 | 6/1989 |
| WO | WO-92/16215 | 10/1992 |
| WO | WO-94/07904 | 4/1994 |
| WO | WO-94/17043 | 8/1994 |
| WO | WO-94/17090 | 8/1994 |
| WO | WO-98/17279 | 4/1998 |
| WO | WO-03/045968 | 6/2003 |

OTHER PUBLICATIONS

Vippagunta et al. Advanced Drug Delivery Reviews 48 (2001) 3-26.*
Lugemwa et al. The Journal of Biological Chemistry vol 271, No. 32, Aug. 9, 1996, pp. 19159-19165.*
Greene et al. Protective Groups in Organic Synthesis, Third Edition, 1999 John Wily & Sons,Inc., pp. 23-27, 573, 574, and 586-590.*
Akira, "Mammalian Toll-like receptors", *Current Opinion*, 2003, 15: 5-11.
Akira, "Toll-Like Receptor Signalling", *Immunology*, 2004, 4:499-511.
Alexander et al., "(Acyloxy)alkyl Carbamates as Novel Bioreversible Prodrugs for Amines: Increased Permeation through Biological Membranes", J. Med. Chem., 1988, 31:318-322.
Applequist et al., "Variable expression of Toll-like receptor in murine innate and adaptive immune cell lines", *Int. Immunol.*, 2002, 14(9):1065-74.
Barrio et al., "Regioselective Fluorination of Substituted Guanines with Dilute $F_2$: A Facile Entry to 8-Fluoroguanine Derivatives", *J. Org. Chem.*, 1996, 61:6084-6085.
Bottcher et al., "Differential regulation of Toll-like receptor mRNAs in experimental murine central nervous system infections", *Neurosci. Lett.*, 2003, 344(1):17-20.
Bruno et al., "Mouse pre-immunocytes as non-proliferating multipotent precursors of macrophages, interferon-producing cells, $CD8\alpha^+$ and $CD8\alpha^-$ dendritic cells", *Eur. J. Immunol.*, 2001, 31(11):3403-12.
Chuang et al., "Cloning and characterization of a sub-family of human Toll-like receptors: hTLR7, hTLR8 and hTLR9", *Eru. Cytokine Netw.*, Sep. 2000, 11(3):372-8.

(Continued)

*Primary Examiner*—Shaojia Anna Jiang
*Assistant Examiner*—Layla Bland
(74) *Attorney, Agent, or Firm*—Connolly Bove Lodge & Hutz LLP

(57) ABSTRACT

The invention is directed to 3,5-disubstituted and 3,5,7-trisubstituted-3H-oxazolo and 3H-thiazolo[4,5-d]pyrimidin-2-one compounds and prodrugs thereof that have immunomodulatory activity. The invention is also directed to the therapeutic or prophylactic use of such compounds and pharmaceutical compositions containing them, and to methods of treating diseases and disorders described herein, by administering effective amounts of such compounds and prodrugs.

12 Claims, 2 Drawing Sheets

OTHER PUBLICATIONS

Daskalov et al., Synthesis and Properties of O6-Substituted Guanosine Derivatives, Bull. Chem. Soc. Jpn., 54(10:3076-3083 (1981).

Diebold et al, "Innate antiviral responses by means of TLR7-mediated recognition of single-stranded RNA", *Science*, 2004, 303(5663):1481-2.

Doxsee et al, "The Immune Response Modifier and Toll-like Receptor 7 Agonist S-27609 Selectively Induces IL-12 and TNF-α Production in CD11c$^+$CD11b$^+$ CD8$^-$ Dendritic Cells", *J. Immunol.*, 2003, 171(3):1156-63.

Du et al., *Eur. Cytokine Netw.*, 2000, 11(3), 362-71.

Edwards et al., "Toll-like receptor expression in murine DC subsets: lack of TLR7 expression by CD8α$^+$ DC correlates with unresponsiveness to imidazoquinolines", *Eur. J. Immunol.*, 2003, 33(4):827-33.

Fan et al., "Pyrimidines. 24. Analogues and Derivatives of 2-Amino-5-bromo-6-phenyl-4(3$H$)-pyrimidinone (ABPP)", *J. Heterocyclic Chem.*, Nov. 1993, 30:1273-1276.

Fathi et al., "Synthesis of 6-Substituted 2'-Deoxyguanosine Derivatives Using Trifluoroacetic Anhydride in Pyridine", Tetrahedron Letters, 31(3):319-322 (1990).

Fried, et al., "5-Substituted 2-Amino-6-phenyl-4(3$H$)-pyrimidinones. Antiviral- and Interferon-Inducing Agents", *J. Med. Chem.*, 1980, 23:237-239.

Fujiwara et al., "Synthesis and Bioactivities of Novel Piperidylpyrimidine Derivatives: Inhibitors of Tumor Necrosis Factor-Alpha Production", *Bioorg. Med. Chem. Lett.*, 2000, 10(12):1317-1320.

Furneaux et al., "Improved Syntheses of 3$H$,5$H$-Pyrrolo[3,2-$d$]pyrimidines", *J. Org. Chem.*, 64 (22), 8411-8412 (1999).

Gangwar et al., "*Synthesis of a Novel Esterase-Sensitive Cyclic Prodrug of a Hexapeptide Using an (Acyloxy)alkoxy Promoiety)*", *J. Org. Chem.*, 1997, 62:1356-1362.

Gibson et al., "Plasmacytoid dendritic cells produce cytokines and mature in response to the TLR7 agonists, imiquimod and resiquimod", *Cell Immunol.*, 2002, 218(1-2):74-86.

Girgis et al., "Direct C-Flycosylation of Guanine Analogues: The Synthesis and Antiviral Activity of Certain 7- and 9-Deazaguanine C-*Nucleosides*", J. Med. Chem., 1990, 33:2750-2755.

Goodman, "Role of Salvage and Phosphorylation in the Immunostimulatory Activity of C8-Substituted Guanine Ribonucleosides", J. Immunol., 14(7):2394-2399 (1988).

Hall et al., "Aldehyde Oxidase from Rabbit Liver: Specificity Toward Purines and Their Analogs", Archives of Biochemistry and Biophysics, 25(1):36-46 (1986).

Heil et al., "The Toll-like receptor 7 (TLR7)-specific stimulus Ioxoribine uncovers a strong relationship within the TLR7, 8 and 9 subfamily", *Eur. J. Immunol.*, 2003, 33(11):2987-97.

Hemmi et al., "Small anti-viral compounds activate immune cells via the TLR7 MyD88-dependent signaling pathway", *Nat. Immunol.*, 2002, 3(2):196-200.

Henry et al., "Synthesis and Broad-Spectrum Antiviral Activity of 7,8-Dihydro-7-methyl-8-thioxoguanosine", *J. Med. Chem.*, 1990, 33:2127-2130.

Hirota et al., "Discovery of 8-Hydroxyadenines as a Novel Type of Interferon Inducer", *J. Med. Chem.*, 2002, 45:5419-5422.

Horng et al., "The adaptor molecule TIRAP provides signaling specificity for Toll-like receptors", *Nature*, 2002, 420(6913):329-333.

Hornung et al., "Quantitative Expression of Toll-Like Receptor 1-10 mRNA in Cellular Subsets of Human Peripheral Blood Mononuclear Cells and Sensitivity to CpG Oligodeoxynucleotides", *J. Immunol.*, 2002, 168(9):4531-4537.

Isobe et al, "Synthesis and Structure-Activity Relationships of 2-Substituted-8-hydroxyadenin Derivatives as Orally Available Interferon Inducers without Emetic Side Effects", *Bioorganic & Medicinal Chemistry*, 2003, 11:3641-3647.

Ito et al., "Roles of Toll-Like Receptors in Natural Interferon-Producing Cells as Sensors in Immune Surveillance", *Hum. Immunol.*, 2002, 63(12):1120-1125.

Jarrossay, "Specialization and complementarity in microbial molecule recognition by human myeloid and plasmacytoid dendritic cells", *Eur. J. Immunol.*, 2001, 31(11):3388-3393.

Kerr et al, "Isatoribine, a Toll Like Receptor 7 Agonist, Significantly Reduced Plasma Viral Load in a Proof-of-Concept Study in Patients with Chronic Hepatitis C Virus Infection", . . . .

Kini et al., "Synthesis and Antiviral Activity of Certain Guanosine Analogues in the Thiazolo[4,5-$d$]pyrimidine Ring System", *J. Med. Chem.*, 1991, 34:3006-3010.

Krasny et al., "Metabolism and Pharmacokinetics of a Double Prodrug of Ganiclovir in the Rat and Monkey", Drug Metabolism and Disposition, 23(11):1242-1247 (1995).

Krasny et al., "Allopurinol as an Inhibitor of the in vivo Formation of Acyclovir from Desiclovir", Biochem. Pharm., 35(23):4339-4340 (1986).

Krenitsky et al., "6-Deoxyacyclovir: A xanthjne oxidase-activated prodrug of acyclovir", Proc. Natl. Acad. Sci., 81:3209-3213 (1984).

Krenitsky et al., "Xanthine Oxidase from Human Liver: Purification and Characterization", Archives of Biochemistry and Biophysics, 247(1):108-119 (1986).

Kurimoto et al., "Prodrugs of 9-Benzyl-8-hydroxy-2-(2-hydroxyethylthio)adenine: Potent Interferon Inducing Agents in Monkeys", *Chem. Pharm. Bull.*, 2004, 52(4):466-469.

Kurimoto et al., "Synthesis and evaluation of 2-substituted 8-hydroxyadenines as potent inferferon inducers with improved oral bioavailabilities", *Bioorg. Med. Chem.*, 2004, 12:1091-1099.

Le Quesne et al., "Biomimetic Synthesis of Catechol Estrogens" Potentially Mutagenic Arene Oxide Intermediates in Estrogen Metabolism, *J. Med. Chem*, 1980, 23:239-240.

Lee et al., "Molecular basis for the immunostimulatory activity of guanine nucleoside analogs: activation of Toll-like receptor 7" *PNAS*, 2003, 100(11): 6646-6651.

Lewis et al., "Thiazolo[4,5-$d$]pyrimidines. Part I. Synthesis and Anti-Human Cytomegalovirus (HCMV) Activity in vitro of Certain Alkyl Derivatives", J. Het. Chem., 32, 547-56.

Lore et al, "Toll-Like Receptor Ligands Modulate Dendritic Cells to Augment Cytomegalovirus- and HIV-1-Specific T Cell Responses", *J. Immunol.*, 2003, 171(8): 4320-4328.

Mealy, "ANA-971", *Drugs of the Future*, 2004, 29(5):507.

Mealy, "ISIS-14803—20-Mer antisense phosphorothioate oligodeoxynucleotide whose sequence is: 5'GTGCmTCmATG-GTGCmACmGGTCmT-3' where Cm represents 5-methylcytidine", *Drugs of the Future*, May 2004, 29(5):526-27.

Michael et al, "Alkylpurines as Immunopotentiating Agents. Synthesis and Antiviral Activity of Certain Alkylguanines", *J. Med. Chem.*, 1993, 36:3431-3436.

Miettinen et al., "IFNs activate toll-like receptor gene expression in viral infections", *Genes Immun.*, 2001, 2(6):349-355.

Mohty et al., "IFN-α Skews Monocyte Differentiation into Toll-Like Receptor 7-Expressing Dendritic Cells with Potent Functional Activities", *J. Immunol.*, 2003, 171(7):3385-93.

Nagahara et al., "Thiazolo[4,5-d] pyrimidine Nucleosides. The Synthesis of Certain 3-B-D-Ribofuranosylthiazolo[4,5-d]pyrimidines as Potential Immunotherapeutic Agents", J. Med. Chem., 33(1):407-415 (1990).

Nagase et al., "Expression and Function of Toll-Like Receptors in Eosinophils: Activation by Toll-Like Receptor 7 Ligand[1]", *J. Immuno.*, 2003, 171(8):3977-3982.

O'Neill, "After the Toll Rush", *Science*, 2004, 303:1481-1482.

Okada et al., "Murine thymic plasmacytoid dendritic cells", *Eur. J. Immunol.*, 2003, 33(4): 1012-9.

Pinhal-Enfield et al., "An Angiogenic Switch in Macrophages Involving Synergy between Toll-Like Receptors 2, 4, 7, and 9 and Adenosine $A_{2A}$ Receptors", *Am. J. Pathol.*, 2003, 163(2):711-721.

Pockros et al., "A Phase IIa Placeob-Controlled, Double-Blind Trial to Determine the Safety, Tolerability, PK/PD of An Oral Interferon Inducer, Resiquimod, in chronic HCV", *Gastroenterology*, 2003, 124(Suppl 1): A-766.

Pockros, "Attacking the Hepatitis C Virus with New Mechanisms of Action: Drugs in the Pipeline", *The HCV Advocate: Medical Writers's Circle*, May 2004, pp. 1-5.

Purifoy et al., "Review of Research Leading to New Anti-Herpesvirus Agents in Clinical Development: Valaciclovir Hydrochloride (256U, the L-Valyl Ester of Acyclovir) and 882C, a Specific Agent for Varicella Zoster Virus", Journal of Medical Virology Supplement, 1:139-145 (1993).

Raney et al, "HEP DART 2003: Frontiers in Drug Development for Viral Hepatitis", *Expert Opin. Investig. Drugs*, 2004, 13(3):289-293.

Reitz, et al., "Small-Molecule Immunostimulants. Synthesis and Activity of 7,8-Disubstituted Guasnosines and Structurally Related Compounds", *J. Med. Chem.*, 1994, 37(21):3561-3578.

Revankar et al., "Synthesis and Antiviral/Antitumor Activities of Certain 3-Deazaguanine Nucleosides and Nucleotides", *J. Med. Chem.*, 1984, 27:1389-96.

Revankar et al., "Thiazolo[4,5-d]Pyrimidines. Part II. Synthesis and Anti-human Cytomegalovirus Activity in Vitro of Certain Acyclonucleosides and Acyclonucleotides Derived from Guanine Analogue 5-Aminothiazolo[4,5-d]Pyrimidine-2,7(3H,6H)-dione", Antiviral Chemistry & Chemotherapy, 9:53-63 (1998).

Revankar et al., "Synthesis of Certain *N*- and *C*-Alkyl Purine Analogs", J. Het. Chem., 30, 1341-49 (1993).

Rhodes, "Discovery of immunopotentiatory drugs: current and future strategies", *Clin. Exp. Immunol.*, 2002, 130:363-369.

Rida et al., "Synthesis of Novel Thiazolo[4,5-d]Pyrimidine Derivatives for Antimicrobial, Anti-HIV and Anticancer Investigation", Pharmazie, 51(12):927-931 (1996).

Rothenfusser et al., "Plasmacytoid Dendritic Cells: The Key to CpG", *Hum. Immunol.*, 2002, 63(12):1111-1119.

Sato et al., "A variety of microbial components induce tolerance to lipopolysaccharide by differentially affecting MyD88-dependent and -independent pathways", *Int. Immunol.*, 2002, 14(7):783-91.

Seela et al., :Alternative d(G-C)3 and d(C-G)3 Hexanucleotides Containing 7-Deaza-2'-deoxyguanosine or 8-Aza-7-deaza-2'deoxyguanosine in Place of dG, Nucleic Acids Res., 17(3):901-910 (1989).

Seela et al., "Synthese von 2-Amino-2,7-dihydro-7-(62-D-ribofuranosyl)-4H-pyrrolo[2,3-*d*]pyrimidin-4-on—7-Desazaguanosin—der Stammverbindung des Nucleosids Q", *Chem. Ber.*, 1981, 114 (10):3395-3402.

Skulnick et al. , "Pyrimidinones. 3. N-Substituted 6-Phenylpyrimidinones and Pyrimidinediones with Diuretic/Hypotensive and Antiinflammatory Activity", *J. Med. Chem.*, 1986, 29:1499-1504.

Smee et al., "Broad Spectrum In Vivo Antiviral Activity of 7-Thia-8-Oxoguanoine, a Novel Immunopotentiating Agent", Antimicrobial Agents and Chemotherapy, 33(9):1487-1492 (1989).

Smee et al., "Broad-Spectrum Activity of 8-chloro-7-deazaguanosine Against RNA Virus Infections in Mice and Rats", Antiviral Res., 26:203-209 (1995).

Townsend, "The Synthesis of 2-Amiono-7-β-D-ribofuranosyl)pyrrolo[2,3,d)-pyrimidin-4-one (7-Deazaguanosine), a Nucleoside Q and Q* Analog (1)", *J. Heterocyclic Chem*, Dec. 1976, 13:1363-1364.

Ulevitch, "Therapeutics Targeting the Innate Immune System", *Nature*, 2004, 4:512-520.

Wong et al., "Photochemical Synthesis of 8-Hydroxyguanine Nucleosides", Methods Enzymol., 234:59-65 (1994).

Yamamoto et al., "Cutting Edge: A Novel Toll/IL-1 Receptor Domain-Containing Adapter That Preferentially Activates the IFN-β Promoter in the Toll-Like Receptor Signalinig[1]", *J. Immunol.*, 2002, 169(12):6668-72.

Yamamoto et al., "Essential role for TIRAP in activation of signaling cascade shared by TLR2 and TLR4", *Nature*, 2002, 420(6913):324-9.

"Oral Interferon-Like Molecule", *Updated on New Experimental Therapies*, http://archive.mail-list.com/pkids/msg03975.html, Jul. 21, 2004.

International Search Report and Written Opinion (PCT/US05/45589) dated May 18, 2006.

* cited by examiner

3,5-DISUBSITITUTED AND 3,5,7-TRISUBSTITUTED-3H-OXAZOLO AND 3H-THIAZOLO[4,5-D]PYRIMIDIN-2-ONE COMPOUNDS AND PRODRUGS THEREOF

This application claims the benefit of U.S. Provisional Application No. 60/636,633, filed Dec. 17, 2004, and U.S. Provisional Application No. 60/636,634, filed Dec. 17, 2004.

FIELD OF THE INVENTION

The invention is directed to 3,5-disubstituted and 3,5,7-trisubstituted-3H-oxazolo and 3H-thiazolo[4,5-d]pyrimidin-2-one compounds and prodrugs thereof that have immunomodulatory activity. The invention is also directed to the therapeutic or prophylactic use of such compounds and pharmaceutical compositions containing them, and to methods of treating diseases and disorders described herein, by administering effective amounts of such compounds and prodrugs.

BACKGROUND OF THE INVENTION

The last few decades have seen significant efforts expended in exploring possible therapeutic uses of guanine analogs and nucleosides thereof. A number of nucleoside analogs are currently being marketed as antiviral drugs, including HIV reverse transcriptase inhibitors such as AZT, ddI, ddC, d4T, 3TC and the guanosine nucleoside analog abacavir. While not adhering to a particular theory, nucleoside analogs may provide benefits by directly inhibiting the pathogen or tumor, by stimulation of host immune functions, or some combination of these or other mechanisms.

One of the studied guanosine analogs with demonstrated immunomodulatory activity is 5-amino-3-(O-D-ribofuranosylthiazolo[4,5-d]pyrimidine-2,7(3H,6H) dione (7-thia-8-oxoguanosine). For example, certain pyrimido[4,5-d]pyrimidine nucleosides are disclosed in U.S. Pat. No. 5,041,542 to Robins et al. as being effective in treatment against L1210 in BDF1 mice. In addition, 3-β-D-ribofuranosylthiazolo[4,5-d] pyrimidines demonstrating significant immunoactivity, including murine spleen cell proliferation and in vivo activity against Semliki Forest virus, are disclosed U.S. Pat. Nos. 5,041,426 and 4,880,784 to Robins et al. A number of publications have also described non-glycosyl derivatives of the thiazolo[4,5-d]pyrimidine moiety. See, e.g., U.S. Pat. Nos. 5,994,321 and 5,446,045; Revankar et al., *J. Het. Chem.*, 30, 1341-49 (1993); Lewis et al., *J. Het. Chem.*, 32, 547-56 (1995).

SUMMARY OF THE INVENTION

The present invention describes novel 3,5-disubstituted and 3,5,7-trisubstituted-3H-oxazolo and 3H-thiazolo[4,5-d] pyrimidin-2-one compounds, pharmaceutically active prodrugs, pharmaceutically active metabolites, pharmaceutically acceptable salts, and pharmaceutically acceptable solvates thereof, which are useful as immunomodulators.

In another embodiment, the present invention encompasses a method of treating or preventing a hepatitis C virus infection in a patient in need thereof comprising administering to the patient a therapeutically or prophylactically effective amount of a 3,5-disubstituted and 3,5,7-trisubstituted-3H-oxazolo and 3H-thiazolo[4,5-d]pyrimidin-2-one compound or a prodrug thereof.

In a general aspect, the invention relates to prodrugs that are 3,5-disubstituted and 3,5,7-trisubstituted-3H-oxazolo and 3H-thiazolo[4,5-d]pyrimidin-2-one compounds of Formula I

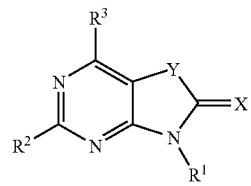

wherein

X is O or S,

Y is O or S, $R^1$ is H, alkyl, aryl, cycloalkyl, or heterocyclyl, $R^2$ is $NH_2$, —NHC(O)$R^4$, —NH$R^5$, —N=CHN$R^6R^7$, $R^3$ is H, Cl, Br, or O$R^8$, $R^4$ is —$C_1$-$C_7$-alkyl or —O($C_1$-$C_7$-alkyl), $R^5$ is —$C_1$-$C_7$-alkyl, $R^6$ and $R^7$ are independently —$C_1$-$C_7$-alkyl or together with nitrogen form a 5- or 6-membered heterocyclic ring, $R^8$ is —CH$R^9R^{10}$, $R^9$ is H, —$C_1$-$C_7$-alkyl, cycloalkyl, aryl, heterocyclyl, —N$R^{11}R^{12}$, or O$R^5$, $R^{10}$ is —$C_1$-$C_7$-alkyl, cycloalkyl, aryl, heterocyclyl, —N$R^{11}R^{12}$, or O$R^5$, $R^{11}$ and $R^{12}$ are independently H, —$C_1$-$C_7$-alkyl, or —C(O)$R^4$, wherein when X is O, Y is S, and $R^3$ is H, Cl, Br, or O$R^8$, $R^1$ is not H or β-D-ribose or esters thereof, wherein the above alkyl, aryl, cycloalkyl, or heterocyclyl moieties are optionally substituted by 1-4 substituents selected from
- hydrogen,
- alkanoyl,
- alkylamine,
- amino,
- aryl, cycloalkyl, heterocyclyl,
- azido,
- $C_1$-$C_6$ alkyl, $C_1$-$C_6$ haloalkyl, $C_1$-$C_6$ hydroxyalkyl, $C_1$-$C_6$ alkoxy, $C_1$-$C_6$ alkylamine, $C_1$-$C_6$ dialkylamine, $C_2$-$C_6$ alkenyl, or $C_2$-$C_6$ alkynyl, wherein each of which may be interrupted by one or more hetero atoms,
- carboxyl,
- cyano,
- halo,
- hydroxy,
- mercapto,
- nitro,
- thioalkyl,
- —N=N—$NH_2$,
- —C(O)$_2$—($C_1$-$C_6$ alkyl), —C(O)$_2$-(aryl), —C(O)$_2$-(cycloalkyl), —C(O)$_2$-(heterocyclyl), —O—($C_1$-$C_6$ haloalkyl), —O—($C_1$-$C_6$ alkyl)aryl, —O—($C_1$-$C_6$ alkyl)cycloalkyl, —O—($C_1$-$C_6$ alkyl)heterocyclyl, —O—($C_1$-$C_6$ alkyl)amino, —O—($C_1$-$C_6$ alkyl)alkylamino, —O—($C_1$-$C_6$ alkyl)dialkylamino, —O—($C_1$-$C_6$ alkyl)-C(O)-amino, —O—($C_1$-$C_6$ alkyl)-C(O)-alkylamino, —O—($C_1$-$C_6$ alkyl)-S(O)$_2$-amino, —O—($C_1$-$C_6$ alkyl)-S(O)$_2$-alkylamino, —O—(C$_1$-C$_6$ alkyl)-S(O)$_2$-dialkylamino, —O—(C$_1$-C$_6$ alkyl)-C(O)-dialkylamino, —O-aryl, —O-heterocyclyl, —NHC(O)—(C$_1$-C$_6$ alkyl), —NHC(O(C$_1$-C$_6$ alkenyl), —NHC(O)-(aryl), —NHC(O)-(cycloalkyl), —NHC(O)-(heterocyclyl), —NHC(O—C$_1$-C$_6$ alkyl)aryl, —NHC(O)—(C$_1$-C$_6$ alkyl)cycloalkyl, —NHC(O)—(C$_1$-C$_6$ alkyl)heterocyclyl, —NHC(O)—(C$_1$-C$_6$ alkyl)amino, —NHC(O)—(C$_1$-C$_6$ alkyl)alkylamine, —NHC(O)—(C$_1$-C$_6$ alkyl)dialkylamine, —NHC(O)—(C$_1$-C$_6$ alkyl)C(O)amino, —NHC(O)—(C$_1$-C$_6$ alkyl)C(O)alkylamine, —NHC(O)—(C$_1$-C$_6$ alkyl)C(O)dialkylamine, —NHC(O)—(C$_1$-C$_6$ alkyl)N(H)—(C$_1$-C$_6$ alkyl)C(O)$_2$—(C$_1$-C$_6$ alkyl), —NH—(C$_1$-C$_6$ alkyl)-C(O)-amino, —NH—(C$_1$-C$_6$ alkyl)-C(O)-alkylamino, —NH—(C$_1$-C$_6$ alkyl)-C(O)-dialkylamino, —NHC(O)—(C$_1$-C$_6$ alkyl)S(O)$_2$(C$_1$-C$_6$ alkyl), —NHC(O)—(C$_1$-C$_6$ alkyl)-S-(heterocyclyl), —NHS(O)$_2$—(C$_1$-C$_6$ alkyl), —NHS(O)$_2$-aryl), —NH—(C$_1$-C$_6$ alkyl)-S(O)$_2$-amino, —NH—(C$_1$-C$_6$ alkyl)-S(O)$_2$-alkylamino, —NH—(C$_1$-C$_6$ alkyl)-S(O)$_2$-dialkylamino, —NHS(O)$_2$-cycloalkyl), —NHS(O)$_2$-heterocyclyl), —NHS(O)(C$_1$-C$_6$ alkyl), —NHS(O)(aryl), —NHS(O)(cycloalkyl), —NHS(O)(heterocyclyl), —NHS(C$_1$-C$_6$ alkyl), —NHS(aryl), —NHS(cycloalkyl), and —NH—S-(heterocyclyl), wherein each of the above substituents can be further optionally substituted by 1-5 substituents selected from amino, C$_1$-C$_6$ alkylamine, C$_1$-C$_6$ dialkylamine, C$_1$-C$_6$ alkyl, C$_1$-C$_6$ alkoxy, C$_1$-C$_6$ alkenyl, C$_1$-C$_6$ hydroxyl, and C$_1$-C$_6$ hydroxyalkyl, each optionally substituted by cyano, halo, and nitro, or a pharmaceutically acceptable salt, hydrate, or stereoisomer thereof.

In one embodiment, the invention relates to compounds of Formula I, wherein R$^2$ is NH$_2$.

In another embodiment, the invention relates to compounds of Formula I, wherein R$^3$ is H.

In another embodiment, the invention relates to compounds of Formula I, wherein X is O and Y is S.

In another embodiment, the invention relates to compounds of Formula I, wherein R$^1$ is selected from

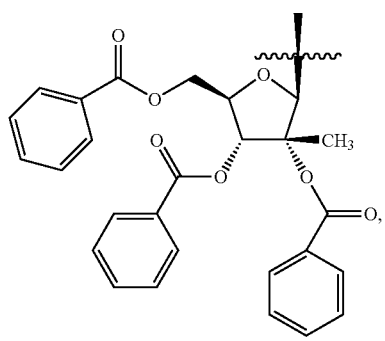

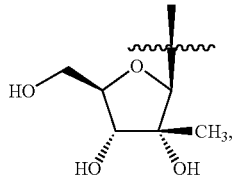

-continued

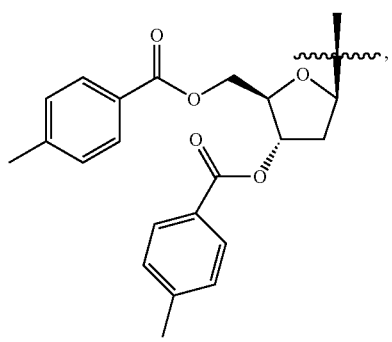

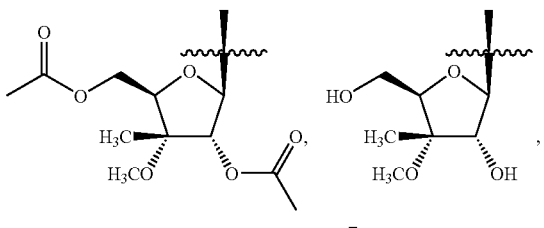

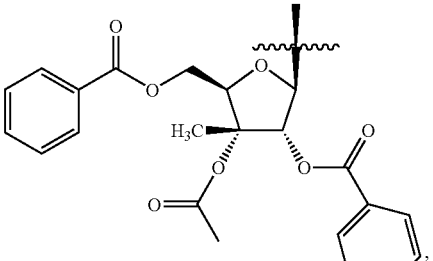

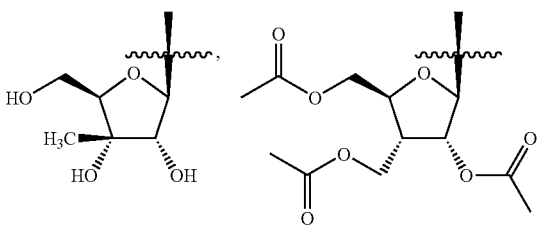

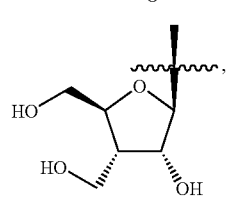

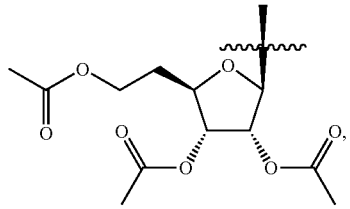

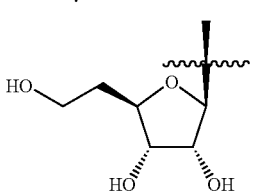

-continued
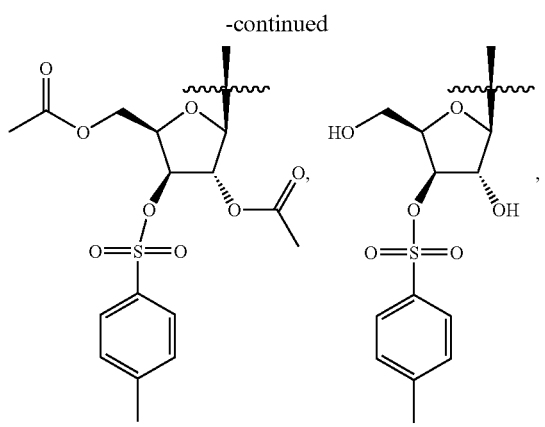
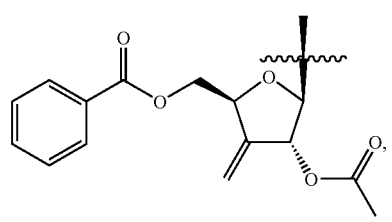
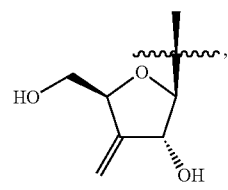
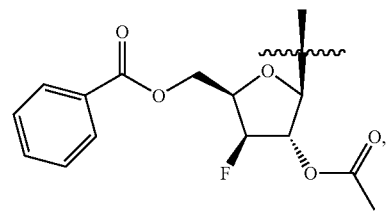
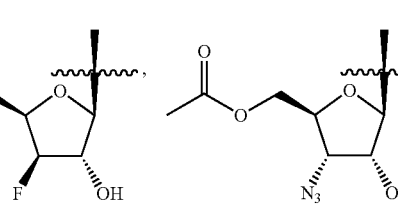
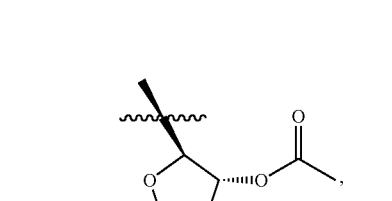
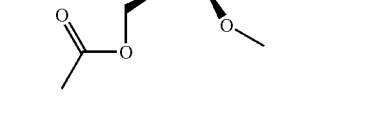
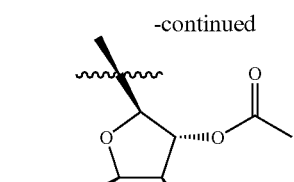
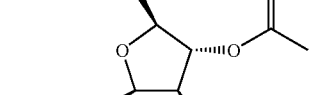

-continued
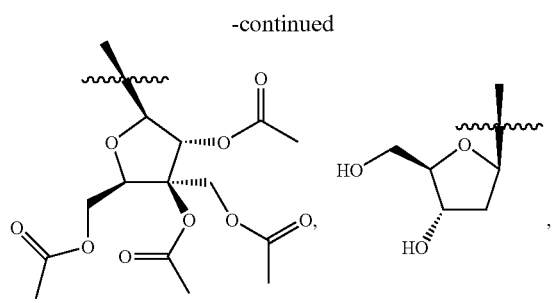
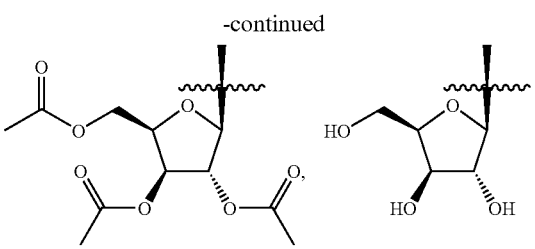
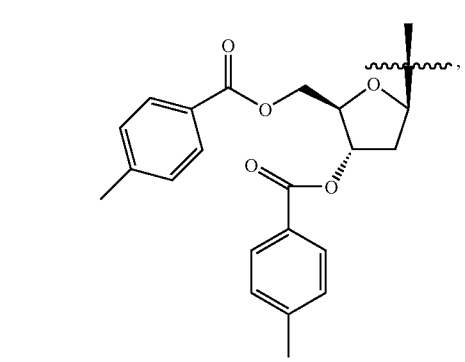
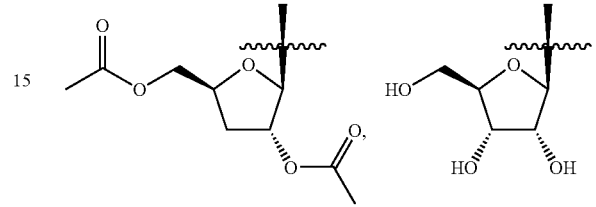
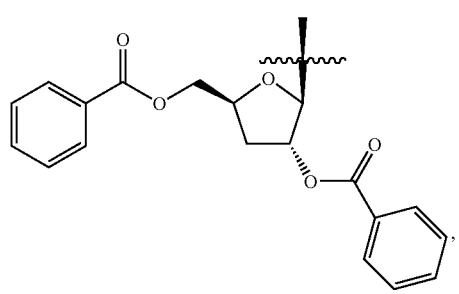
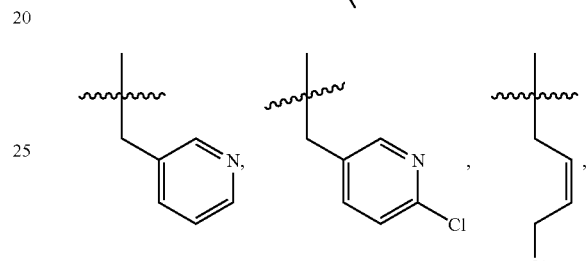
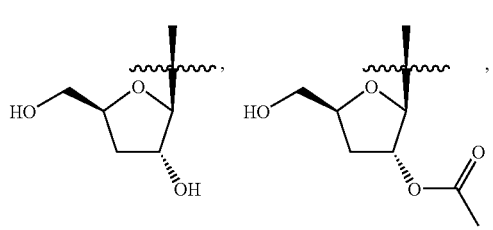
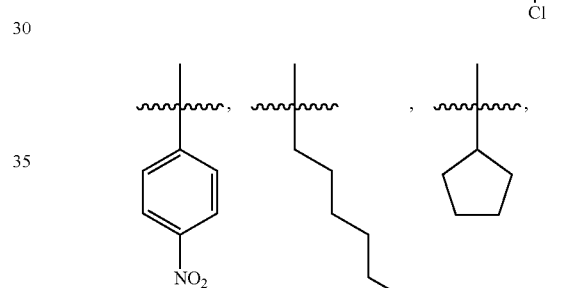
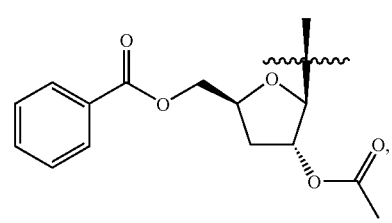
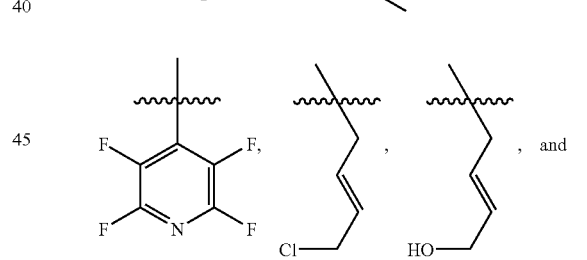
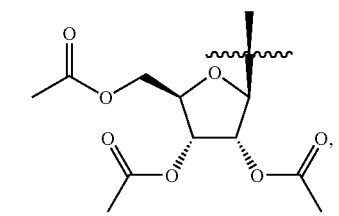
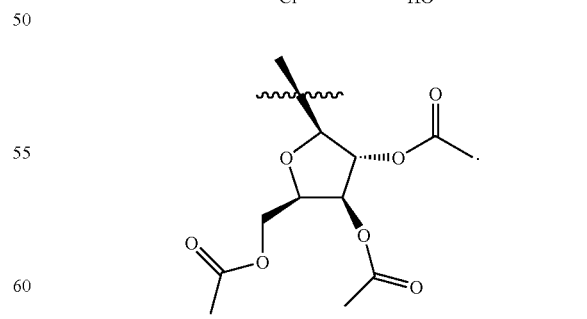
In another embodiment, the invention relates to compounds of the Formula I selected from

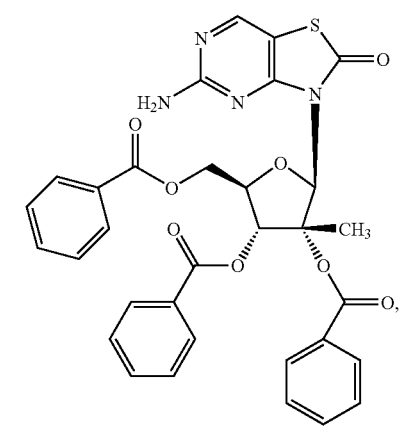
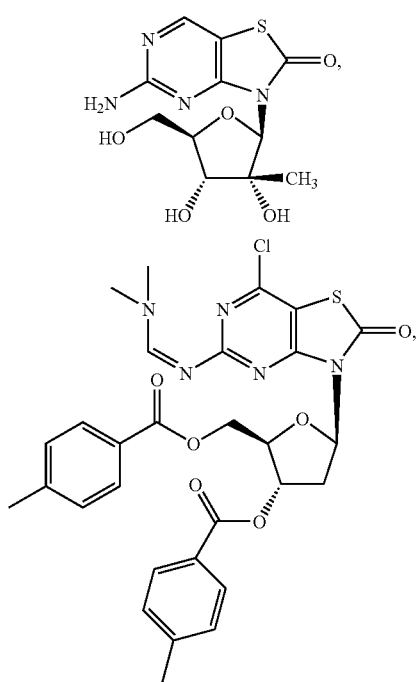
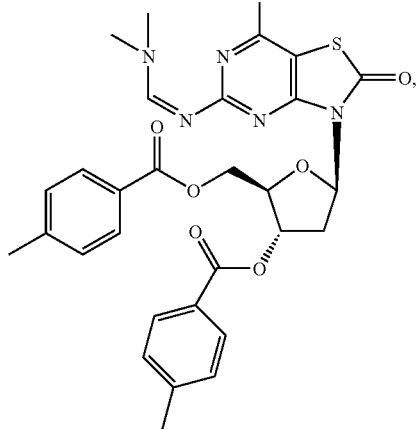
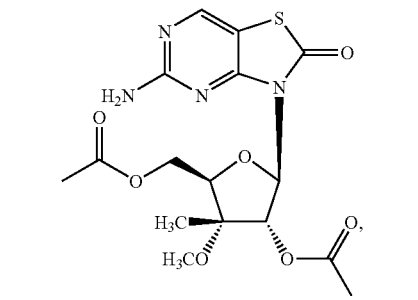
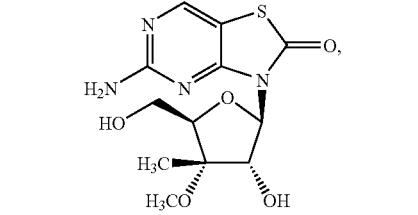
-continued
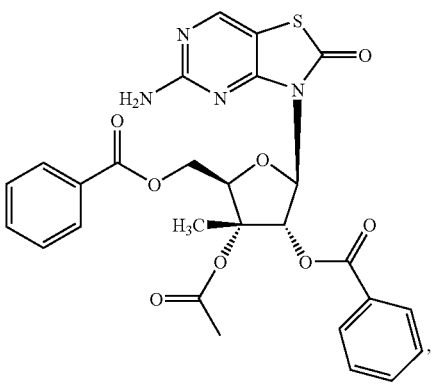
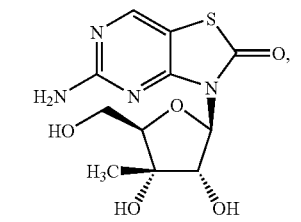
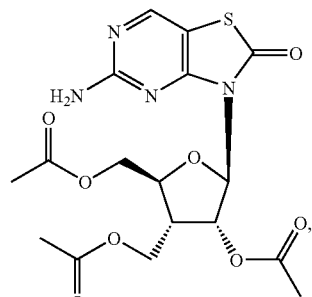
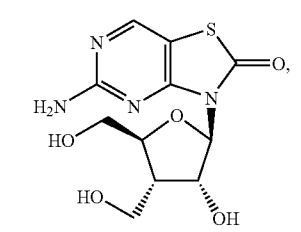
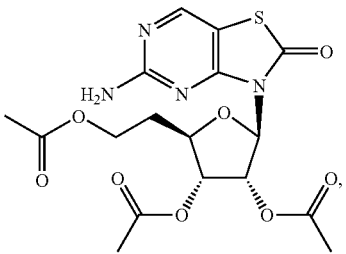
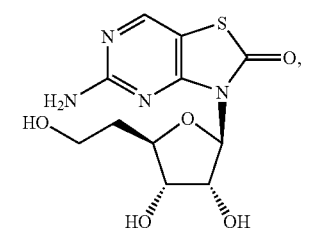

-continued
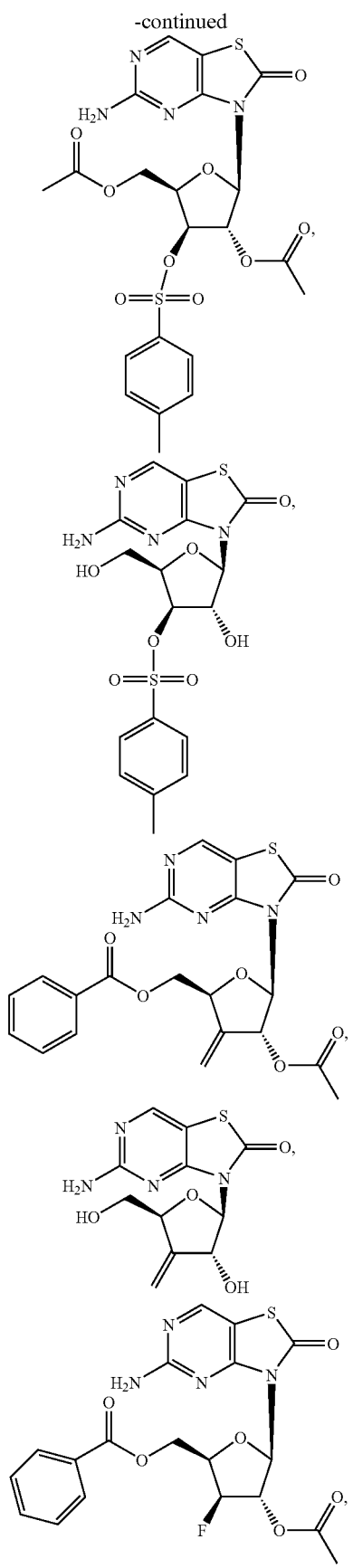
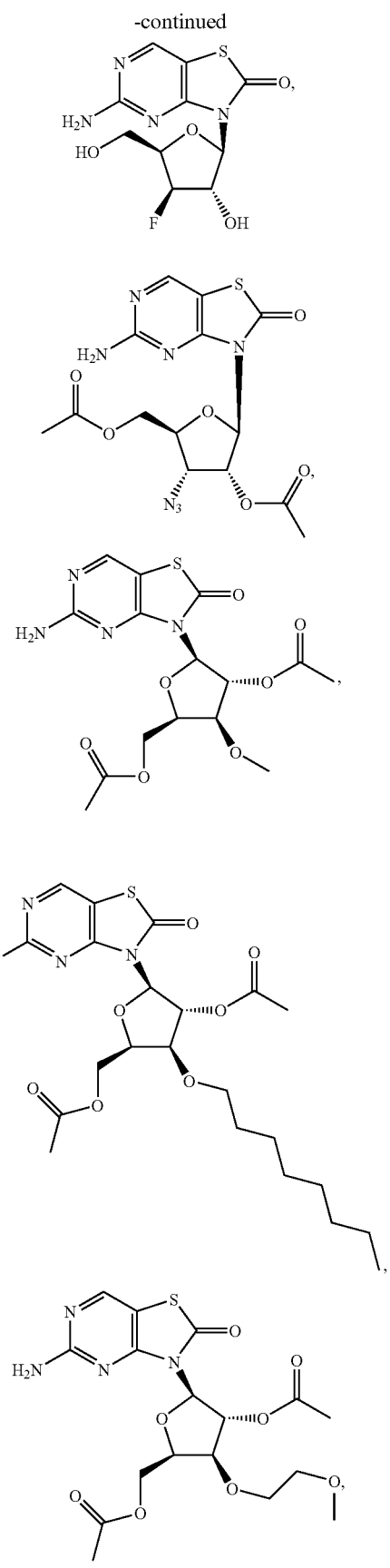

-continued
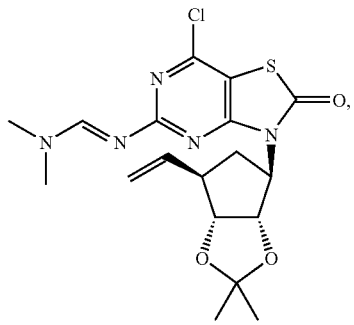
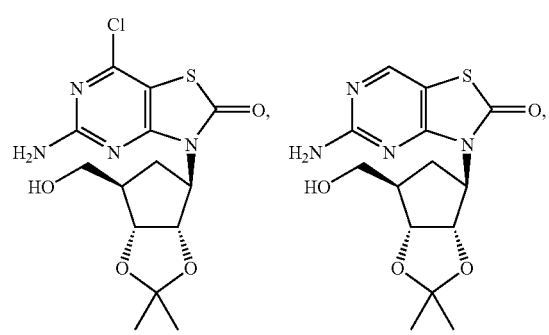
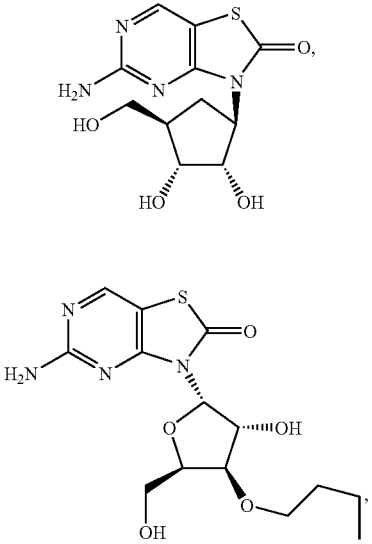
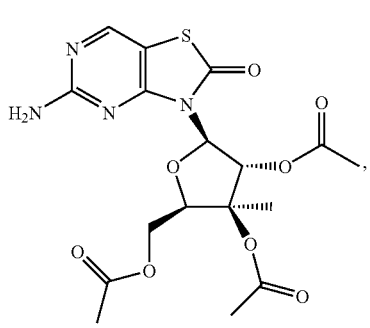
-continued
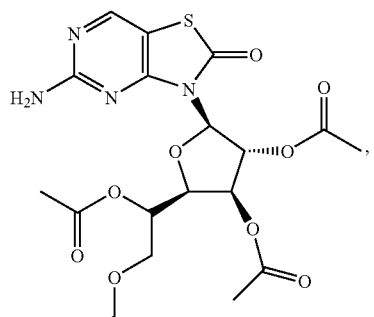
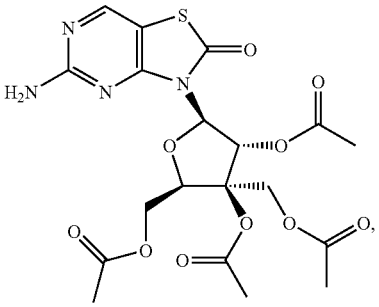
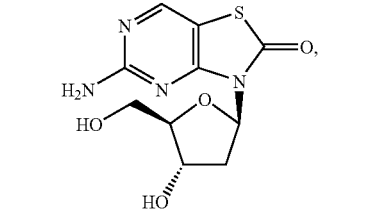
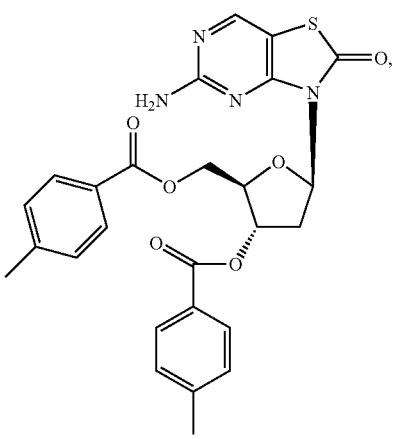
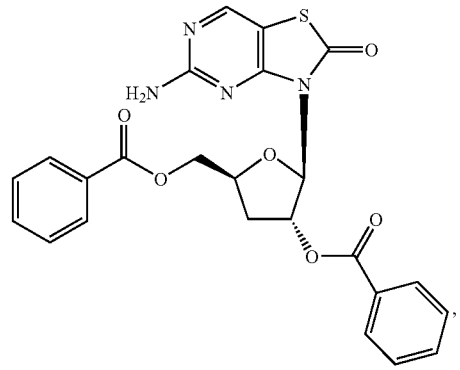

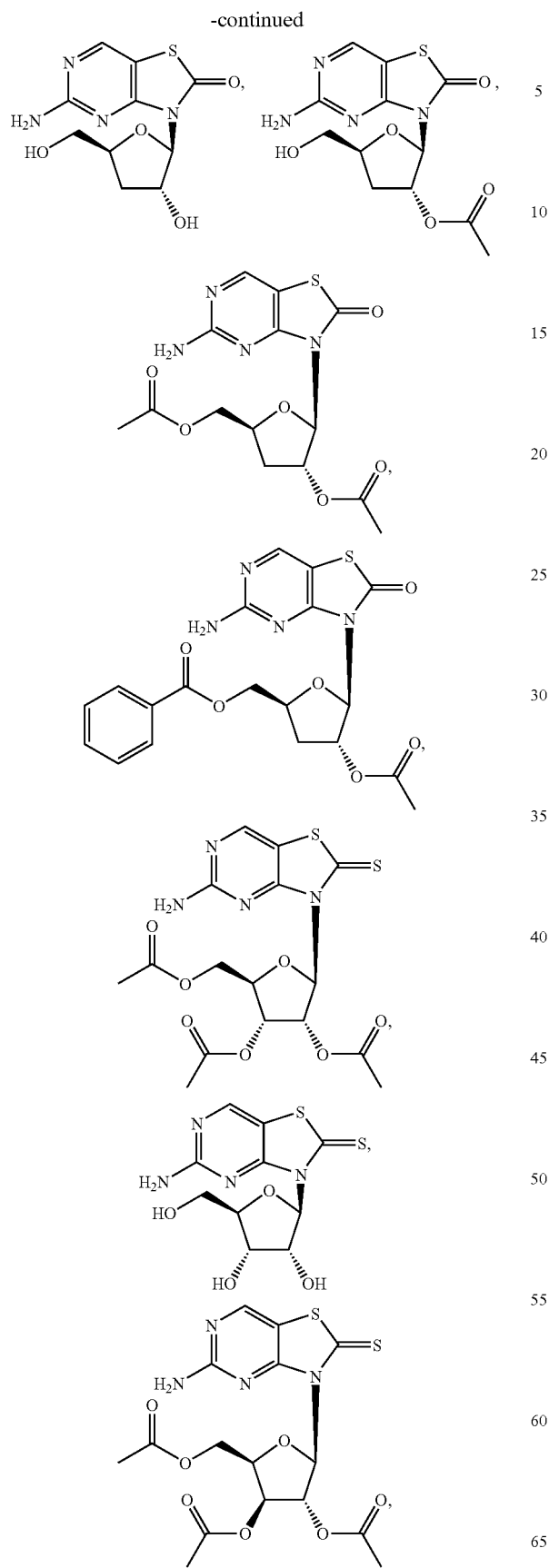
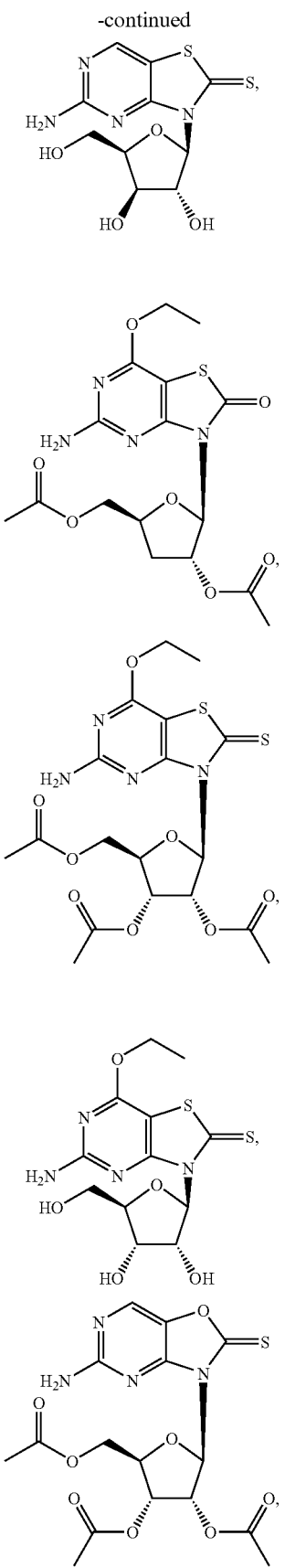

-continued
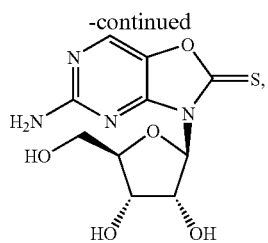
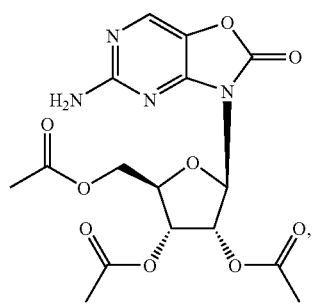
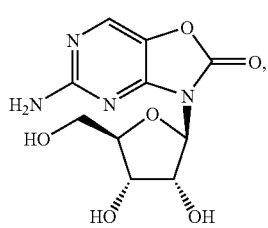
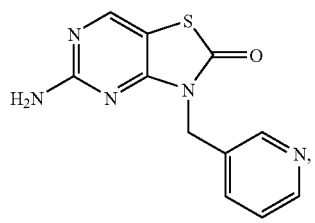
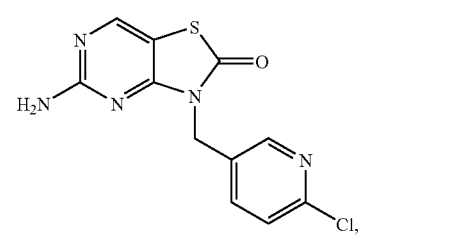
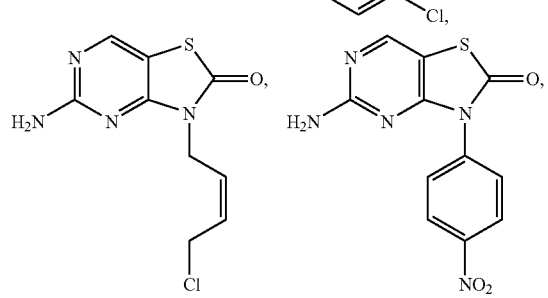
-continued
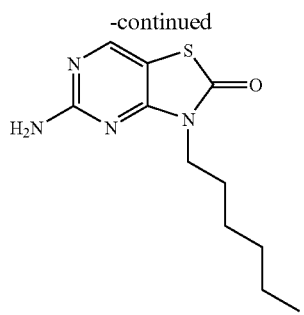
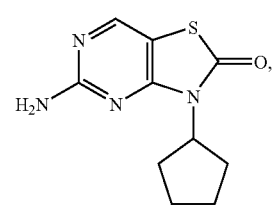
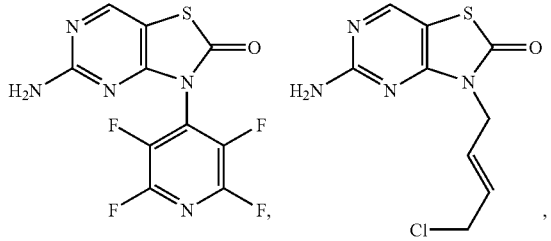
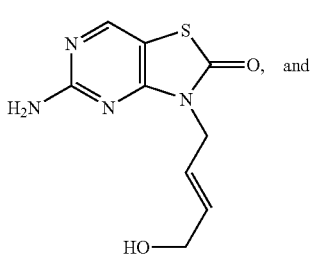
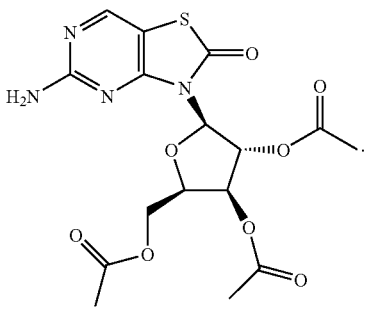
In a another general aspect, the invention relates to 3,5-disubstituted and 3,5,7-trisubstituted-3H-oxazolo and 3H-thiazolo[4,5-d]pyrimidin-2-one compounds of Formula II

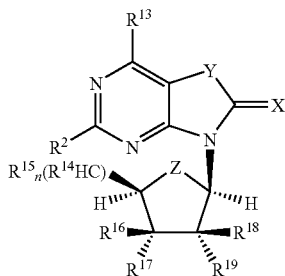

II wherein

X is O or S,

Y is O or S,

Z is O or $CH_2$, $R^2$ is $-NH_2$, $-NHC(O)R^4$, $-NHR^5$, $-N=CHNR^6R^7$, $R^4$ is $-C_1-C_7$-alkyl or $-O(C_1-C_7$-alkyl), $R^5$ is $-C_1-C_7$-alkyl, $R^6$ and $R^7$ are independently $-C_1-C_7$-alkyl or together with nitrogen form a 5- or 6-membered heterocyclic ring, $R^{13}$ is OH or SH, $R^{14}$ is H, $-CH_2OH$, or $-CH_2-O-C(O)C_{1-18}$ alkyl, $R^{15}$ is OH, alkenyl, $-OC(O)C_{1-18}$ alkyl, $-OC(O)$aryl, or $-OC(O)$heterocyclyl, $R^{16}$, $R^{17}$, $R^{18}$, and $R^{19}$ are independently H, halo, $N_3$, alkyl, $-(CH_2)_mOR^{20}$, $-(CH_2)_mOC(O)C_{1-18}$ alkyl, $-OC(O)$aryl, $-OS(O)_2$aryl, or $R^{16}$ and $R^{17}$ are an alkenyl, or $R^{17}$ and $R^{19}$ combine together to form a dioxole ring, $R^{20}$ is H or alkyl, m is 0 or 1, n is 1 or 2, wherein if $R^2$ is $NH_2$, then one of the following must be present:

Z is $CH_2$;

either n is 2 or m is 1;

at least one of $R^{16}$, $R^{17}$, $R^{18}$, and $R^{19}$ is halo, $N_3$, alkyl, or $-(CH_2)_mOR^{20}$ wherein m is 1, and wherein if $R^{17}$ is $N_3$, then $R^{18}$ and $R^{19}$ are not H, and wherein if $R^{17}$ is OH and $R^{16}$ and $R^{19}$ are H, then $R^{18}$ is not F; or $R^{16}$ and $R^{17}$ are an alkenyl, wherein the above alkyl, aryl, cycloalkyl, or heterocyclyl moieties are optionally substituted by 1-4 substituents selected from hydrogen, alkanoyl, alkylamine, amino, aryl, cycloalkyl, heterocyclyl, azido, $C_1-C_6$ alkyl, $C_1-C_6$ haloalkyl, $C_1-C_6$ hydroxyalkyl, $C_1-C_6$ alkoxy, $C_1-C_6$ alkylamine, $C_1-C_6$ dialkylamine, $C_2-C_6$ alkenyl, or $C_2-C_6$ alkynyl, wherein each of which may be interrupted by one or more hetero atoms, carboxyl, cyano, halo, hydroxy, mercapto, nitro, thioalkyl, $-N=N-NH_2$, $-C(O)_2-(C_1-C_6$ alkyl), $-C(O)_2$-(aryl), $-C(O)_2$-(cycloalkyl), $-C(O)_2$-(heterocyclyl), $-O-(C_1-C_6$ haloalkyl), $-O-(C_1-C_6$ alkyl)aryl, $-O-(C_1-C_6$ alkyl)cycloalkyl, $-O-(C_1-C_6$ alkyl)heterocyclyl, $-O-(C_1-C_6$ alkyl)amino, $-O-(C_1-C_6$ alkyl)alkylamino, $-O-(C_1-C_6$ alkyl)dialkylamino, $-O-(C_1-C_6$ alkyl)-C(O)-amino, $-O-(C_1-C_6$ alkyl)-C(O)-alkylamino, $-O-(C_1-C_6$ alkyl)-S(O)_2-amino, $-O-(C_1-C_6$ alkyl)-S(O)_2-alkylamino, $-O-(C_1-C_6$ alkyl)-S(O)_2-dialkylamino, $-O-(C_1-C_6$ alkyl)-C(O)-dialkylamino, $-O$-aryl, $-O$-heterocyclyl, $-NHC(O)(C_1-C_6$ alkyl), $-NHC(O)-(C_1-C_6$ alkenyl), $-NHC(O)$-(aryl), $-NHC(O)$-cycloalkyl), $-NHC(O)$-(heterocyclyl), $-NHC(O)-(C_1-C_6$ alkyl)aryl, $-NHC(O)-(C_1-C_6$ alkyl)cycloalkyl, $-NHC(O)-(C_1-C_6$ alkyl)heterocyclyl, $-NHC(O)-(C_1-C_6$ alkyl)amino, $-NHC(O)-(C_1-C_6$ alkyl)alkylamine, $-NHC(O)-(C_1-C_6$ alkyl)dialkylamine, $-NHC(O)-(C_1-C_6$ alkyl)C(O)amino, $-NHC(O)-(C_1-C_6$ alkyl)C(O)alkylamine, $-NHC(O)-(C_1-C_6$ alkyl)C(O)dialkylamine, $-NHC(O)-(C_1-C_6$ alkyl)N(H)-(C_1-C_6$ alkyl)C(O)_2-(C_1-C_6$ alkyl), $-NH-(C_1-C_6$ alkyl)-C(O)-amino, $-NH-(C_1-C_6$ alkyl)-C(O)-alkylamino, $-NH-(C_1-C_6$ alkyl)-C(O)-dialkylamino, $-NHC(O)-(C_1-C_6$ alkyl)S(O)_2(C_1-C_6$ alkyl), $-NHC(O)-(C_1-C_6$ alkyl)-S-(heterocyclyl), $-NHS(O)_2-(C_1-C_6$ alkyl), $-NHS(O)_2$-(aryl), $-NH-(C_1-C_6$ alkyl)-S(O)_2-amino, $-NH-(C_1-C_6$ alkyl)-S(O)_2-alkylamino, $-NH-(C_1-C_6$ alkyl)-S(O)_2-dialkylamino, $-NHS(O)_2$(cycloalkyl), $-NHS(O)_2$-heterocyclyl), $-NHS(O)(C_1-C_6$ alkyl), $-NHS(O)$(aryl), $-NHS(O)$(cycloalkyl), $-NHS(O)$(heterocyclyl), $-NHS(C_1-C_6$ alkyl), $-NHS$(aryl), $-NHS$(cycloalkyl), and $-NH-S$-(heterocyclyl), wherein each of the above substituents can be further optionally substituted by 1-5 substituents selected from amino, $C_1-C_6$ alkylamine, $C_1-C_6$ dialkylamine, $C_1-C_6$ alkyl, $C_1-C_6$ alkoxy, $C_1-C_6$ alkenyl, $C_1-C_6$ hydroxyl, and $C_1-C_6$ hydroxyalkyl, each optionally substituted by cyano, halo, and nitro, or a pharmaceutically acceptable salt, hydrate, or stereoisomer thereof.

In another embodiment, the invention relates to compounds of Formula II, wherein $R^2$ is $NH_2$.

In another embodiment, the invention relates to compounds of Formula II, wherein $R^{13}$ is OH.

In another embodiment, the invention relates to compounds of Formula II, wherein X is O and Y is S.

In another embodiment, the invention relates to compounds of Formula II selected from 21
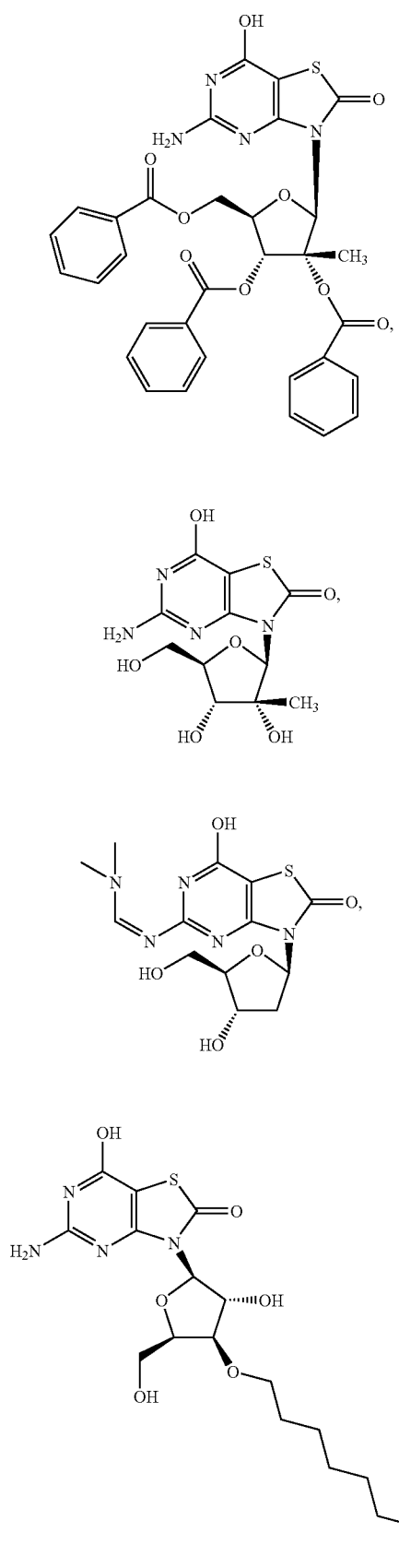
22
-continued
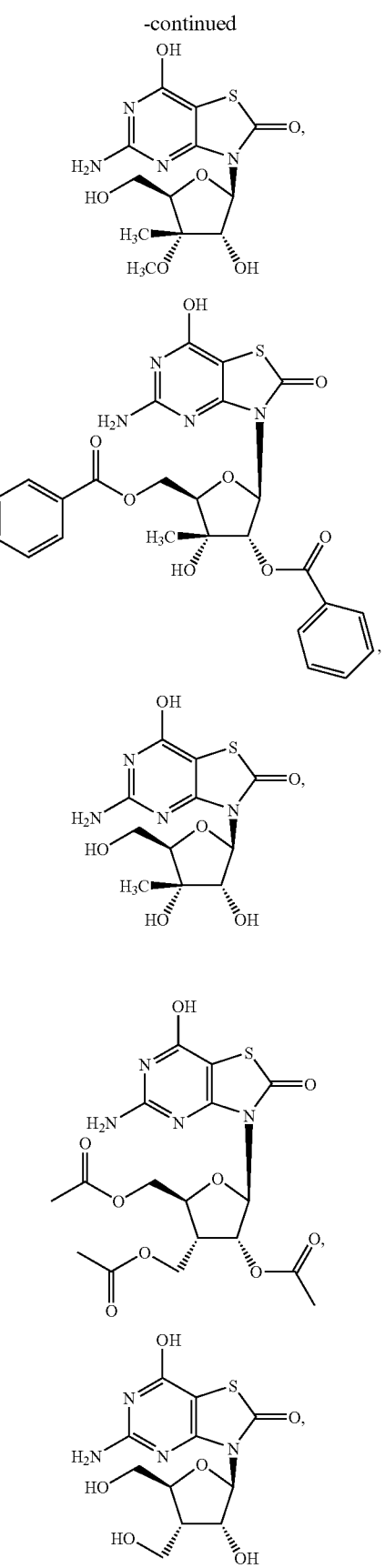

-continued
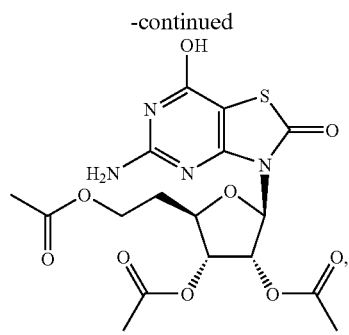
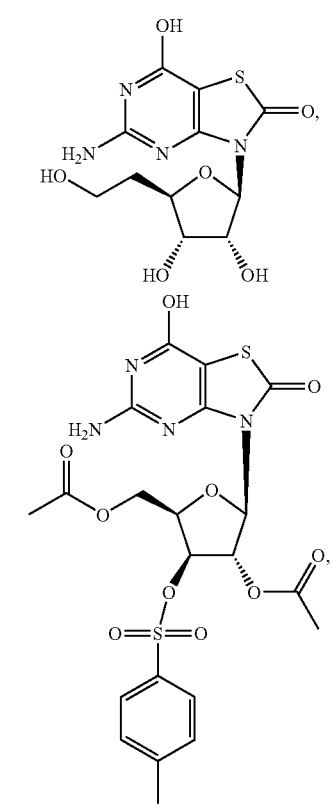
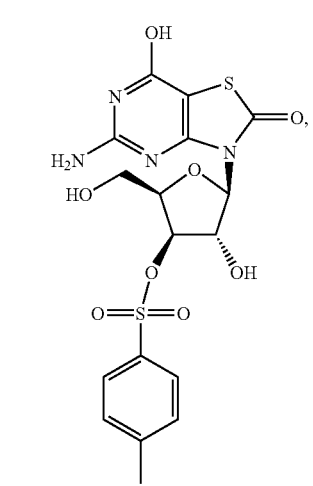
-continued
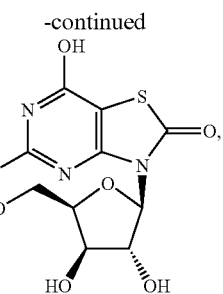
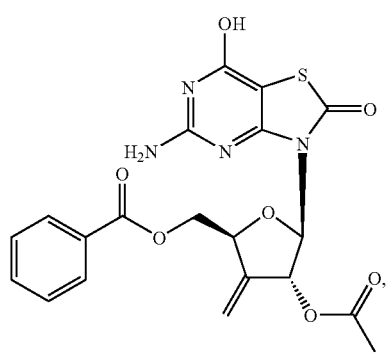
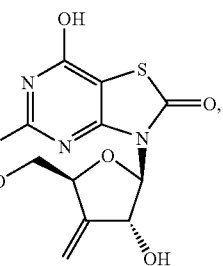
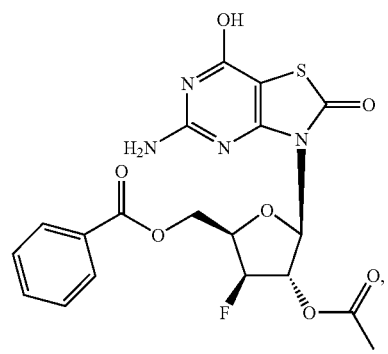
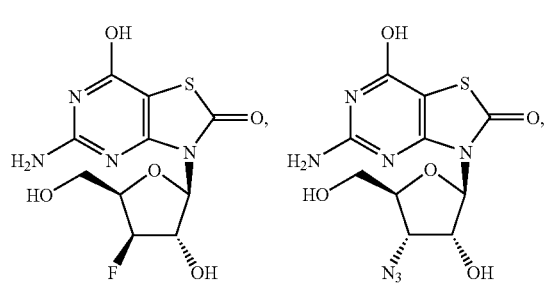

25
-continued
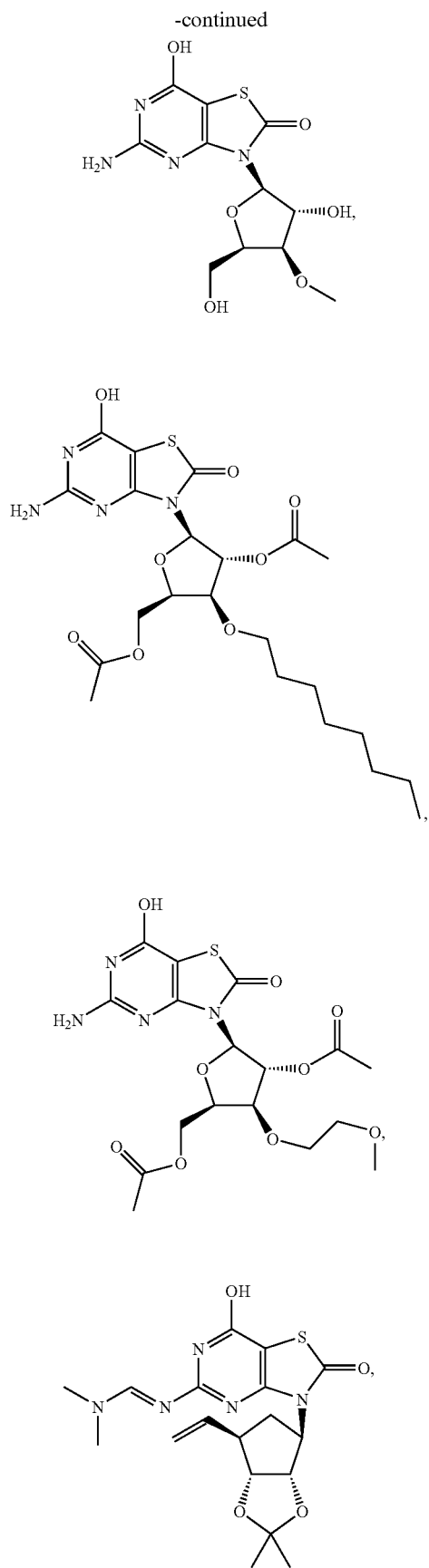
26
-continued
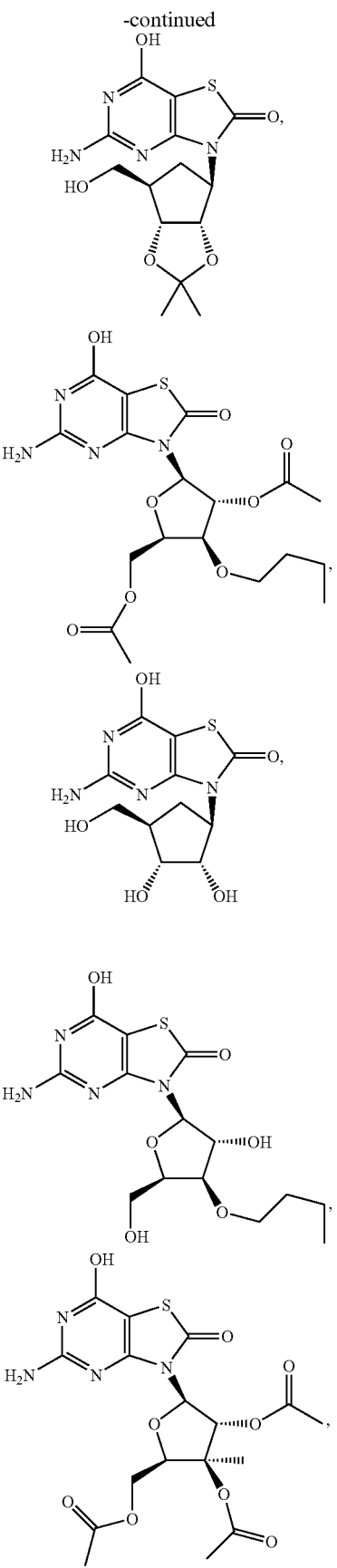

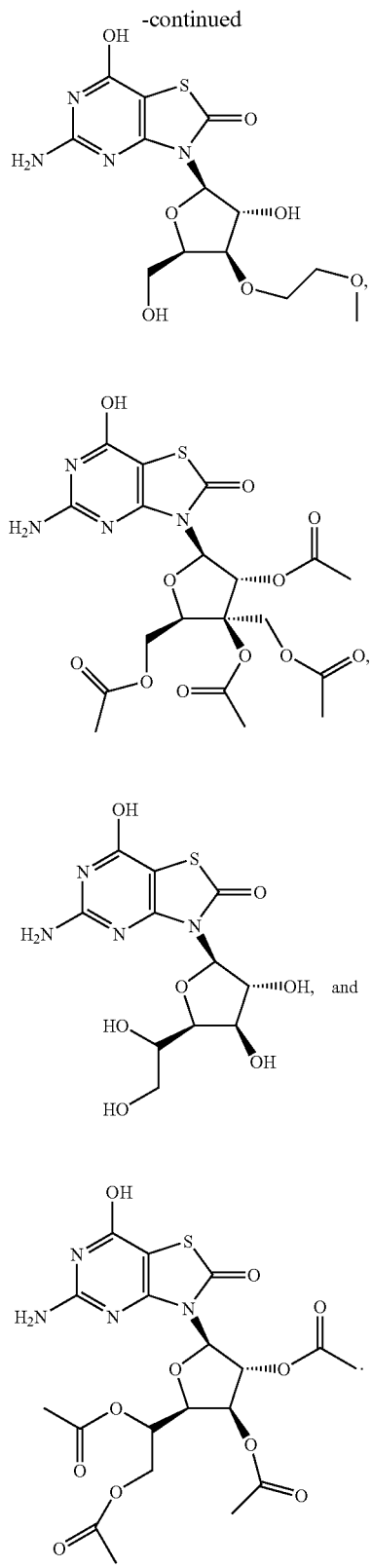
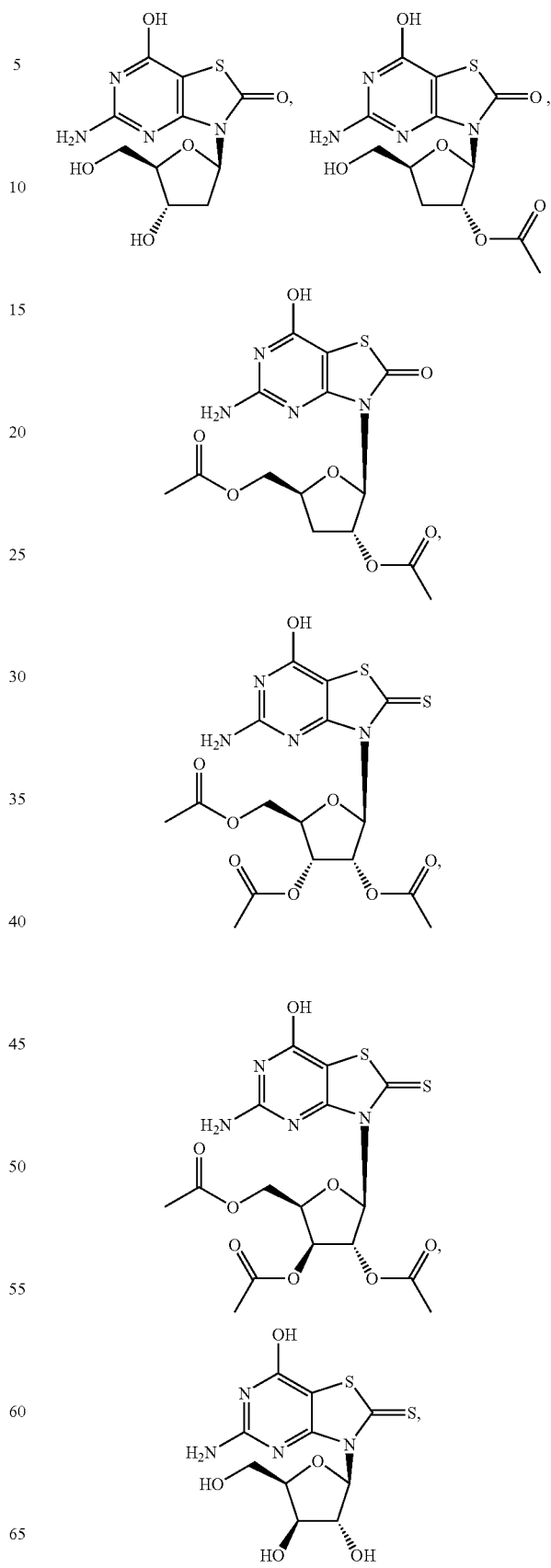
In a another general aspect, the invention relates to 3,5-disubstituted and 3,5,7-trisubstituted-3H-oxazolo and 3H-thiazolo[4,5-d]pyrimidin-2-one compounds selected from -continued

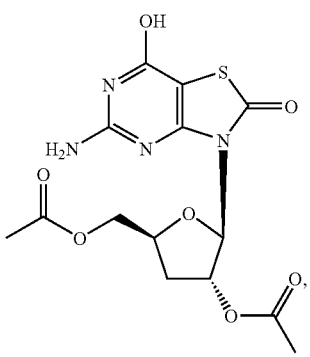
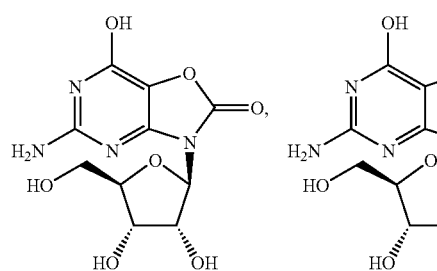
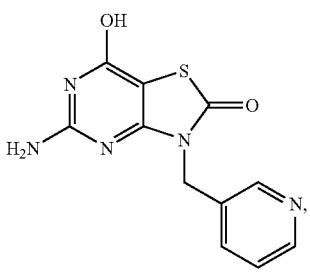
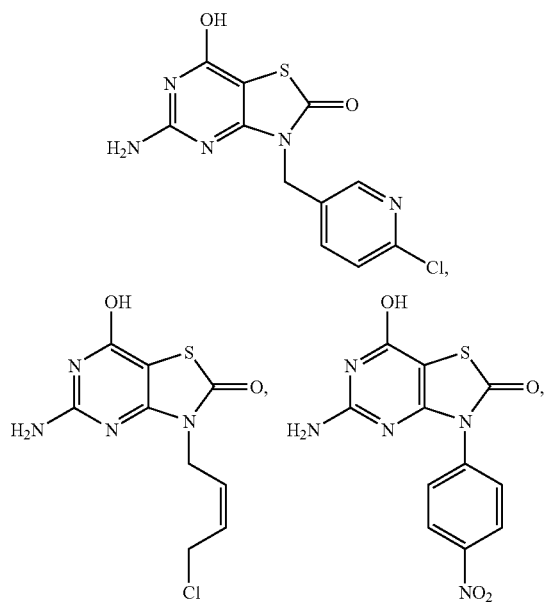

-continued

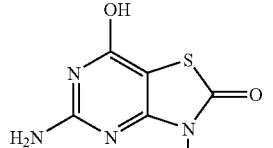
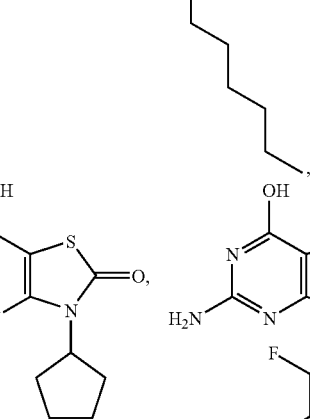
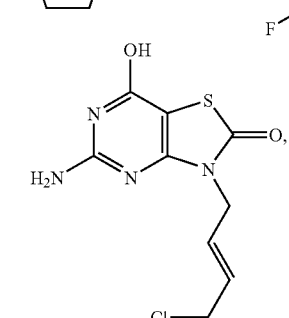
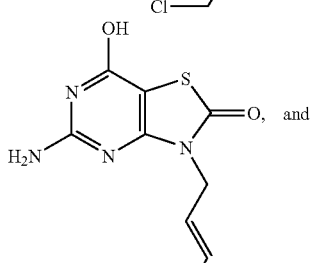
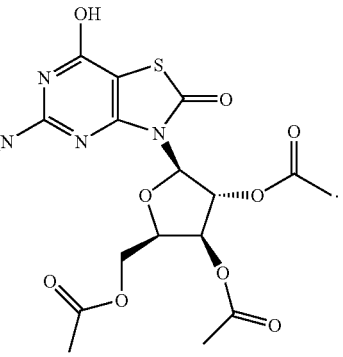

The invention is also directed to pharmaceutically active metabolites, pharmaceutically acceptable salts, and pharmaceutically acceptable solvates of the compounds or metabolites of the Formula I prodrugs, Formula II compounds, and other compounds of the invention. Advantageous methods of making the compounds of the invention are also described.

The Formula I prodrugs, Formula II compounds, and other compounds of the invention are useful as immune system enhancers and have certain immune system properties including modulation, mitogenicity, augmentation, and/or potentiation or they are intermediates for compounds that have these properties. The compounds are expected to express effects on at least the natural killer, macrophages, dendritic or lymphocyte cells of the immune system of a host. Because of these properties they are useful as antiviral and antitumor agents or as intermediates for antiviral and antitumor agents. They can be used to treat an affected host by serving as the active ingredients of suitable pharmaceutical compositions.

In one aspect of the invention, Formula I prodrugs, Formula II compounds, and other compounds of the invention are utilized to treat the full range of viral diseases in mammals, including humans, by administering to the mammal a therapeutically effective amount of the compounds. Viral diseases contemplated to be treated with compounds of the invention include acute and chronic infections caused by both RNA and DNA viruses. Without limiting in any way the range of viral infections that may be treated, Formula I prodrugs, Formula II compounds, and other compounds of the invention are particularly useful in the treatment of infections caused by adenovirus, cytomegalovirus, hepatitis A virus (HAV), hepatitis B virus (HBV), flaviviruses including Yellow Fever virus and hepatitis C virus (HCV), herpes simplex type 1 and 2, herpes zoster, human herpesvirus 6, human immunodeficiency virus (HIV), human papilloma virus (HPV), influenza A virus, influenza B virus, measles, parainfluenza virus, poliovirus, poxvirus (including smallpox and monkeypox virus), rhinovirus, respiratory syncytial virus (RSV), multiple families of viruses that cause hemorrhagic fevers, including the Arenaviruses (LCM, Junin virus, Machup virus, Guanarito virus, and Lassa Fever), the Bunyaviruses (Hanta viruses and Rift Valley Fever) and Filoviruses (Ebola and Marburg virus), a range of viral encephalitides including West Nile virus, LaCrosse virus, California Encephalitis virus, Venezuelan Equine Encephalitis virus, Eastern Equine Encephalitis virus, Western Equine Encephalitis virus, Japanese Encephalitis virus, Kysanur Forest virus, and tickborne viruses such as Crimean-Congo Hemorrhagic fever virus.

In another aspect of the invention, Formula I prodrugs, Formula II compounds, and other compounds of the invention are utilized to treat bacterial, fungal, and protozoal infections in mammals by administering to the mammal a therapeutically effective amount of the compounds. The full range of pathogenic microorganisms is contemplated to be treatable by the compounds of the present invention, including without limitation those organisms that are resistant to antibiotics. The ability of compounds to activate multiple components of the immune system bypasses resistance mechanisms commonly found to reduce susceptibility to antibiotics, and thus treatment of infections in a mammal caused by such resistant microorganisms by Formula I prodrugs, Formula II compounds, and other compounds of the invention is a particular utility of the present invention.

In another aspect of the invention, Formula I prodrugs, Formula II compounds, and other compounds of the invention are utilized to treat tumors in mammals by administering to the mammal a therapeutically effective amount of the compounds. Tumors or cancers contemplated to be treated include but are not limited to those caused by virus, and the effect may involve inhibiting the transformation of virus-infected cells to a neoplastic state, inhibiting the spread of viruses from transformed cells to other normal cells, and/or arresting the growth of virus-transformed cells. The compounds of the invention are expected to be useful against a broad spectrum of tumors including but not limited to carcinomas, sarcomas, and leukemias. Included in such a class are mammary, colon, bladder, lung, prostate, stomach, and pancreas carcinomas and lymphoblastic and myeloid leukemias.

In another aspect of the invention, a method of treating a mammal comprises administering a therapeutically and/or prophylactically effective amount of a pharmaceutical containing a compound of the invention. In this aspect the effect may relate to modulation of some portion of the mammal's immune system, especially modulation of cytokine activities of Th1 and Th2, including but not restricted to the interleukin family, e.g., IL-1 through IL-12, and other cytokines such as TNF alpha, and interferons including interferon alpha, interferon beta, and interferon gamma, and their downstream effectors. Where modulation of Th1 and Th2 cytokines occurs, it is contemplated that the modulation may include stimulation of both Th1 and Th2, suppression of both Th1 and Th2, stimulation of either Th1 or Th2, and suppression of the other, or a bimodal modulation in which one effect on Th1/Th2 levels (such as generalized suppression) occurs at a high concentration, while another effect (such as stimulation of either Th1 or Th2 and suppression of the other) occurs at a lower concentration.

In another aspect of the invention, pharmaceutical compositions containing a Formula I prodrug, Formula II compound, or other compound of the invention are administered in a therapeutically effective dose to a mammal that is receiving anti-infective drugs not included in the compounds of the invention. In a preferred aspect of this invention, the pharmaceutical compositions containing a Formula I prodrug, Formula II compound, or other compound of the invention are administered in a therapeutically effective dose with anti-infective drug(s) that act directly upon the infectious agent to inhibit the growth of or kill the infectious agent.

In another aspect, the invention encompasses a method for treating or preventing hepatitis C virus infection in a mammal in need thereof, preferably in a human in need thereof.

In another aspect, the invention encompasses a method for treating or preventing hepatitis C virus infection in a patient in need thereof, comprising administering to the patient a therapeutically or prophylactically effective amount of a Formula I prodrug, Formula II compound, or other compound of the invention and a pharmaceutically acceptable excipient, carrier, or vehicle.

In a another aspect, the invention encompasses a method for treating or preventing hepatitis C virus infection in a patient in need thereof, comprising administering to the patient a therapeutically or prophylactically effective amount of a compound of a Formula I prodrug, Formula II compound, or other compound of the invention and an additional therapeutic agent, preferably an additional antiviral agent or antitumor agent as appropriate for the intended use.

In a preferred aspect of the invention, a pharmaceutical composition comprising a therapeutically effective amount of a Formula I prodrug provides for improved oral availability and administration as an immunomodulator. In another preferred aspect of the invention, a pharmaceutical composition comprising a therapeutically effective amount of a Formula I prodrug of the invention provides for masking the active structure as the agent passes through lymphoid tissue lining the stomach, thereby minimizing activation of this tissue and allowing for improved oral tolerability.

DETAILED DESCRIPTION OF THE INVENTION AND PREFERRED EMBODIMENTS

Figure 1:
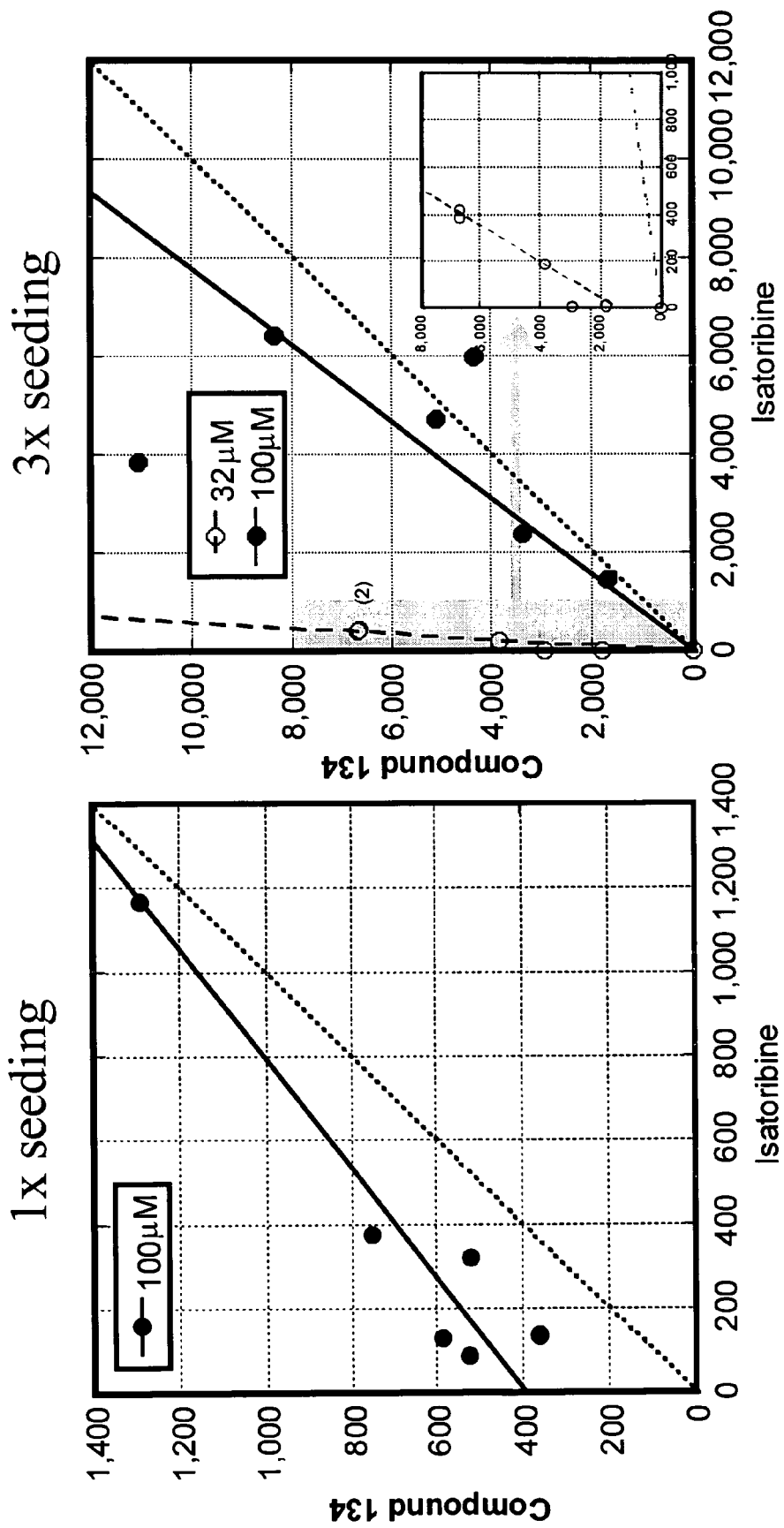
FIG. 1 shows a plot of pg/ml IFN-α induced in human PBMCs from compound 134 vs. pg/ml IFN-α induced by an identical concentration of isatoribine.

Where the following terms are used in this specification, they are used as defined below:

The terms "comprising" and "including" are used herein in their open, non-limiting sense.

The term "pyrimidine" refers to nitrogenous monocyclic heterocycles.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "Me" means methyl, "Et" means ethyl, "Ac" means acetyl, "Bz" means benzoyl, and "Tol" means toluoyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. Illustrative examples of cycloalkyl are derived from, but not limited to, the following:

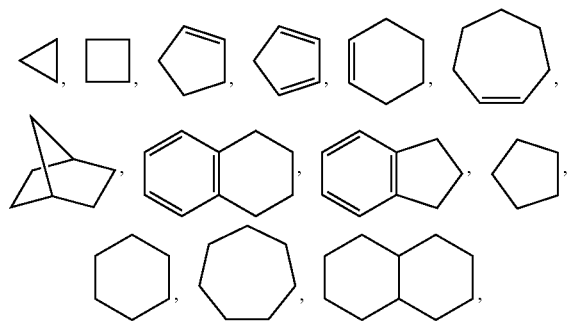

-continued

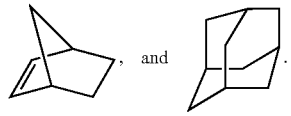, and

The term "aryl", as used herein, unless otherwise indicated, includes an organic radical derived from an aromatic hydrocarbon by removal of one hydrogen, such as phenyl or naphthyl.

The term "heterocyclyl" or "heterocyclic", as used herein, unless otherwise indicated, includes aromatic (e.g., a heteroaryl) and non-aromatic heterocyclic groups containing one to four heteroatoms each selected from O, S and N, wherein each heterocyclic group has from 4-10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4-10 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other illustrative examples of 4-10 membered heterocyclic are derived from, but not limited to, the following:

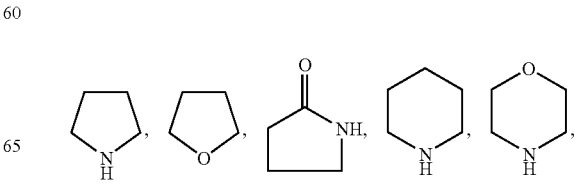

-continued

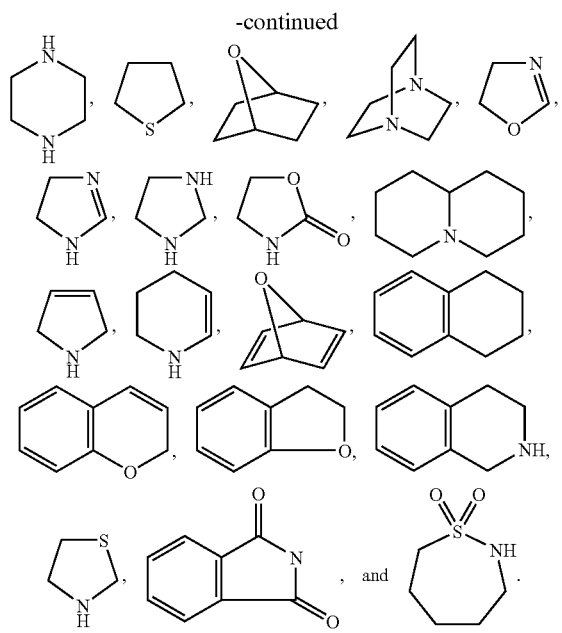

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immunocompromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:

(i) preventing a disease, disorder, or condition from occurring in an animal that may be predisposed to the disease, disorder and/or condition, but has not yet been diagnosed as having it;

(ii) inhibiting the disease, disorder, or condition, i.e., arresting its development; and (iii) relieving the disease, disorder, or condition, i.e., causing regression of the disease, disorder, and/or condition.

The terms "α" and "β" indicate the specific stereochemical configuration of a substituent at an asymmetric carbon atom in a chemical structure as drawn.

The compounds of the invention may exhibit the phenomenon of tautomerism. While the formula drawings cannot expressly depict all possible tautomeric forms, it is to be understood they are intended to represent any tautomeric form of the depicted compound and are not to be limited merely to a specific compound form depicted by the formula drawings. For example, it is understood for Formula II that regardless of whether or not the substituents are shown in their enol or their keto form, they represent the same compound (as shown in the example below).

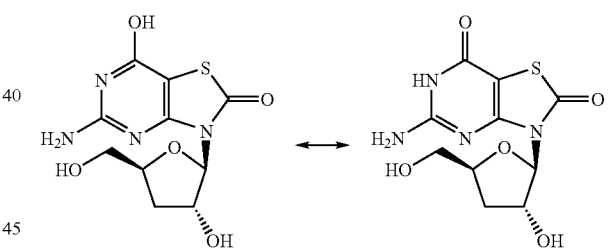

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, Formula I prodrugs, Formula II compounds, and other compounds of the invention are intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to Formula I prodrugs, Formula II compounds, and other compounds of the invention, the invention includes pharmaceutically active metabolites and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect (s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared using methods known in the art, such as those described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Methods of Treatment and Prevention of Hepatitis C Viral Infections

The present invention provides methods for treating or preventing a hepatitis C virus infection in a patient in need thereof.

The present invention further provides methods for introducing a therapeutically effective amount of a Formula I prodrug, Formula II compound, or other compound of the invention or combination of such compounds into the blood stream of a patient in the treatment and/or prevention of hepatitis C viral infections.

The magnitude of a prophylactic or therapeutic dose of a Formula I prodrug, Formula II compound, or other compound of the invention or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lie preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of the compounds may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of Formula I prodrugs, Formula II compounds, and other compounds of the invention are exposed to the ligand and the magnitude of response is measured by an appropriate technique. The assessment of the compounds is then evaluated with respect to the compound potency, and the degree of conversion between the Formula I prodrug and Formula II parent compound. Compounds for use in methods of the invention can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a Formula I prodrug, Formula II compound, or other compound of the invention or a pharmaceutically acceptable salt, solvate, or hydrate thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Also, the dose may differ for various particular compounds of the invention; suitable doses can be predicted on the basis of the aforementioned in vitro measurements and on the basis of animal studies, such that smaller doses will be suitable for those compounds that show effectiveness at lower concentrations than other compounds when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day.

Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In a preferred embodiment, the compounds of the invention are administered to provide systemic distribution of the compound within the patient. In a related embodiment, the compounds of the invention are administered to produce a systemic effect in the body.

In another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, β-interferons, alkylating agents, hormones or cytokines. In a preferred embodiment the invention encompasses the administration of an additional therapeutic agent that is HCV specific or demonstrates anti-HCV activity.

The Formula I prodrugs, Formula II compounds, and other compounds of the invention can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The Formula I prodrugs, Formula II compounds, and other compounds of the invention can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The Formula I prodrugs, Formula II compounds, and other compounds of the invention can be administered or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The Formula I prodrugs, Formula II compounds, and other compounds of the invention can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

The Formula I prodrugs, Formula II compounds, and other compounds of the invention can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The Formula I prodrugs, Formula II compounds, and other compounds of the invention can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the alpha-interferons; beta-interferons; adefovir, clevadine, entecavir, pleconaril.

The Formula I prodrugs, Formula II compounds, and other compounds of the invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), and anti-B7 antibodies (e.g., IDEC-114 (IDEC)) and CTLA4-immunoglobulin. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

The Formula I prodrugs, Formula II compounds, and other compounds of the invention can be administered or formulated in combination with an agent which inhibits viral enzymes, including but not limited to inhibitors of HCV protease, such as BILN 2061 and inhibitors of NS5b polymerase such as NM107 and its prodrug NM283 (Idenix Pharmaceuticals, Inc., Cambridge, Mass.).

The Formula I prodrugs, Formula II compounds, and other compounds of the invention can be administered or formulated in combination with an agent which inhibits HCV polymerase such as those described in Wu, *Curr Drug Targets Infect Disord.* 2003; 3(3):207-19 or in combination with compounds that inhibit the helicase function of the virus such as those described in Bretner M, et al *Nucleosides Nucleotides Nucleic Acids.* 2003; 22(5-8): 1531, or with inhibitors of other HCV specific targets such as those described in Zhang X. *IDrugs.* 2002; 5(2): 154-8.

The Formula I prodrugs, Formula II compounds, and other compounds of the invention can be administered or formulated in combination with an agent which inhibits viral replication.

The Formula I prodrugs, Formula II compounds, and other compounds of the invention can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-alpha, and IFN-gamma).

The Formula I prodrugs, Formula II compounds, and other compounds of the invention can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The Formula I prodrugs, Formula II compounds, and other compounds of the invention can be administered or formulated in combination with β-interferons which include, but are not limited to, interferon beta-1a, interferon beta-1b.

The Formula I prodrugs, Formula II compounds, and other compounds of the invention can be administered or formulated in combination with α-interferons which include, but are not limited to, interferon alpha-1, interferon alpha-2a (roferon), interferon alpha-2b, intron, Peg-Intron, Pegasys, consensus interferon (infergen) and albuferon.

The Formula I prodrugs, Formula II compounds, and other compounds of the invention can be administered or formulated in combination with an absorption enhancer, particularly those which target the lymphatic system, including, but not limited to sodium glycocholate; sodium caprate; N-lauryl-ÿ-D-maltopyranoside; EDTA; mixed micelle; and those reported in Muranishi *Crit. Rev. Ther. Drug Carrier Syst.*, 7-1-33, which is hereby incorporated by reference in its entirety. Other known absorption enhancers can also be used. Thus, the invention also encompasses a pharmaceutical composition comprising one or more Formula I prodrugs, Formula II compounds, and other compounds of the invention and one or more absorption enhancers.

The Formula I prodrugs, Formula II compounds, and other compounds of the invention can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The Formula I prodrugs, Formula II compounds, and other compounds of the invention and the other therapeutics agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more Formula I prodrugs, Formula II compounds, and other compounds of the invention without an additional therapeutic agent.

Pharmaceutical Compositions and Dosage Forms

Pharmaceutical compositions and single unit dosage forms comprising a Formula I prodrugs, Formula II compounds, and other compounds of the invention, or a pharmaceutically acceptable salt, or hydrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, a pharmaceutical composition encompassed by this embodiment includes a Formula I prodrug, Formula II compound, or other compound of the invention, or a pharmaceutically acceptable salt, or hydrate thereof, and at least one additional therapeutic agent. Examples of additional therapeutic agents include, but are not limited to, those listed above.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder.

These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent. Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophylized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof. Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g., Remington's Pharmaceutical Sciences, 18th eds., Mack Publishing, Easton Pa., (1990); and Introduction to Pharmaceutical Dosage Forms, 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The compounds of the invention may also be administered directly to the lung by inhalation. For administration by inhalation, a compound of the inventionr can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a compound directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a compound of the invention to the lung (see, e.g., Raleigh et al., *Proc. Amer. Assoc. Cancer Research Annual Meeting,* 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a compound of the invention to the lung is a liquid spray device supplied, for example, by Aradigm Corporation. Liquid spray systems use extremely small nozzle holes to aerosolize liquid drug formulations that can then be directly inhaled into the lung.

In a preferred embodiment, a nebulizer device is used to deliver a compound of the invention to the lung. Nebulizers create aerosols from liquid drug formulations by using, for example, ultrasonic energy to form fine particles that can be readily inhaled (See e.g., Verschoyle et al., *British J. Cancer,* 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In a particularly preferred embodiment, an electrohydrodynamic ("EHD") aerosol device is used to deliver compounds of the invention to the lung. EHD aerosol devices use electrical energy to aerosolize liquid drug solutions or suspensions (see, e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of the compounds of the invention will be known to the skilled artisan and are within the scope of the invention.

Liquid drug formulations suitable for use with nebulizers and liquid spray devices and EHD aerosol devices will typically include a compound of the invention with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the compound. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611, which are herein incorporated by reference) A compound can also be formulated in rectal or vaginal compositions such as suppositories or retention enemas, e.g., containing conventional suppository bases such as cocoa butter or other glycerides.

In addition to the formulations described previously, a compound of the invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver the compounds of the invention. Certain organic solvents such as dimethylsulfoxide can also be employed, although usually at the cost of greater toxicity. The compounds of the invention can also be delivered in a controlled release system. In one embodiment, a pump can be used (Sefton, *CRC Crit. Ref Biomed Eng.,* 1987, 14, 201; Buchwald et al., *Surgery,* 1980, 88, 507; Saudek et al., *N. Engl. J. Med.,* 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, N.Y. (1984); Ranger and Peppas, *J. Macromol. Sci. Rev. Macromol. Chem.,* 1983, 23, 61; see also Levy et al., *Science,* 1985, 228, 190; During et al., *Ann. Neurol.,* 1989,25,351; Howard et al., 1989, *J. Neurosurg.* 71, 105). In yet another embodiment, a controlled-release system can be placed in proximity of the target of the compounds of the invention, e.g., the lung, thus requiring only a fraction of the systemic dose (see, e.g., Goodson, in *Medical Applications of Controlled Release*, supra, vol. 2, pp. 115 (1984)). Other controlled-release system can be used (see, e.g. Langer, *Science,* 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a Formula I prodrug, Formula II compound, or other compound of the invention useful for the treatment or prevention of a Hepatitis C virus infection. In other embodiments, the invention provides a pharmaceutical pack or kit comprising one or more containers comprising a compound of the invention useful for the treatment or prevention of a Hepatitis C virus infection and one or more containers comprising an additional therapeutic agent, including but not limited to those listed above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) and N,N-dimethylforamide (DMF) were purchased from Aldrich in Sure Seal bottles and used as received. Unless otherwise indicated, the following solvents and reagents were distilled under a blanket of dry nitrogen. THF, and $Et_2O$ were distilled from Na-benzophenone ketyl; $CH_2Cl_2$, diisopropylamine, pyridine and $Et_3N$ were distilled from $CaH_2$; MeCN was distilled first from $P_2O_5$, then from $CaH_2$; MeOH was distilled from Mg; PhMe, EtOAc and i-PrOAc were distilled from $CaH_2$; TFAA was purified via simple atmospheric distillation under dry argon.

The reactions set forth below were done generally under a positive pressure of argon at an ambient temperature (unless otherwise stated) in anhydrous solvents, and the reaction flasks were fitted with rubber septa for the introduction of substrates and reagents via syringe. Glassware was oven dried and/or heat dried. The reactions were assayed by TLC and terminated as judged by the consumption of starting material. Analytical thin layer chromatography (TLC) was performed on aluminum-backed silica gel 60 $F_{254}$ 0.2 mm plates (EM Science), and visualized with UV light (254 nm) followed by heating with commercial ethanolic phosphomolybdic acid. Preparative thin layer chromatography (TLC) was performed on aluminum-backed silica gel 60 $F_{254}$ 1.0 mm plates (EM Science) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $Mg_2SO_4$ prior to filtration and evaporation of the solvents under reduced pressure on a rotary evaporator and noted as solvents removed in vacuo. Column chromatography was completed under positive pressure using 230-400 mesh silica gel or 50-200 mesh neutral alumina. Hydrogenolysis was done at the pressure indicated in the examples or at ambient pressure.

$^1$H-NMR spectra were recorded on a Varian Mercury-VX400 instrument operating at 400 MHz and $^{13}$C-NMR spectra were recorded operating at 75 MHz. NMR spectra were obtained as $CDCl_3$ solutions (reported in ppm), using chloroform as the reference standard (7.27 ppm and 77.00 ppm), $CD_3OD$ (3.4 and 4.8 ppm and 49.3 ppm), DMSO-$d_6$, or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Infrared (IR) spectra were recorded on a FT-IR Spectrometer as neat oils, as KBr pellets, or as $CDCl_3$ solutions, and when given are reported in wave numbers ($cm^{-1}$). Mass spectra reported are (+)-ES LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

The described synthetic pathways and experimental procedures utilize many common chemical abbreviations, THF (tetrahydrofuran), DMF (N,N-dimethylformamide), EtOAc (ethyl acetate), DMSO (di-methyl sulfoxide), DMAP (4-dimethylaminopyridine), DBU (1,8-diazacyclo[5.4.0]undec-7-ene), DCM (4-(dicyanomethylene)-2-methyl-6-(4-dimethylamino-styryl)-4H-pyran), MCPBA (3-chloroperoxybenzoic acid), EDC (1-(3-dimethylaminopropyl)-3-ethylcarbodiimide hydrochloride), HATU (O-(7-azabenzotriazol-1-yl)-1,1, 3,3-tetramethyluronium hexafluorophosphate), HOBT (1-hydroxybenzotriazole hydrate), TFAA (trifluoroacetic anhydride), pyBOP (benzotriazol-1-yloxy)tripyrrolidinophosphonium hexafluorophosphate), DIEA (diisopropylethylamine), BOC (tert-butoxycarbonyl), 2,2-DMP (2,2-dimethoxypropane), IPA (isopropyl alcohol), TEA (triethylamine), DCE (1,2-dichloroethane), PPTS (pyridinium p-toluenesulfonate), DEAD (diethylazodicarboxylate), PS (polymer supported), HF (hydrogen fluoride), MeCN (acetonitrile), MeOH (methanol), Val (valine), Phe (phenyl alanine), HPLC (high pressure liquid chromatography), TLC (thin layer chromatography), Bz (benzoyl), Ac (acetyl), Tol (toluoyl), Me (methyl), and the like.

Example 1

5-Amino-3-(2'-C-methyl-β-ribofuranosyl)-3H-thiazolo[4,5-d]pyrimidin-2-one

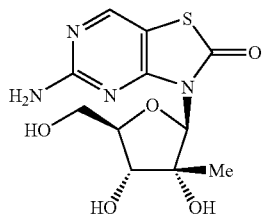

Step 1) Preparation of 5-Amino-3-(2'-C-methyl-2',3',5'-tri-O-benzoyl-β-D-ribofuranosyl)-3H-thiazolo[4,5-d]pyrimidin-2-one (3)

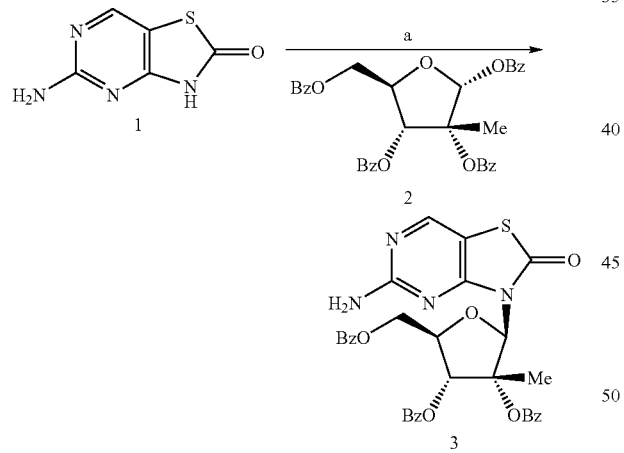

a. BSA, MeCN, rt; TMSOTf, 80° C., 67%

To a heterogeneous mixture of heterocycle 1 (168 mg, 1.00 mmol) and perbenzoyl ribose 2 [prepared according to the method of Wolfe et al. *J. Org. Chem.* 1997, 62, 1754-1759] (522 mg, 0.90 mmol) in anhydrous MeCN (10 mL) was added BSA (742 μL, 3.00 mmol). The resultant mixture was stirred 15 min whereupon TMSOTf (333 μL, 1.50 mmol) was added. The reaction mixture was stirred for 4 h at 65° C., then 3 h at 90° C. The mixture was then cooled to rt, diluted with DCM (150 mL) and partitioned with pH 7 buffer (100 mL). The aqueous phase was further extracted with DCM (3×50 mL), and the combined organic phases were dried over Na$_2$SO$_4$ and filtered. The clear filtrate was diluted with EtOAc (200 mL), filtered through a short pad of SiO$_2$, concentrated and submitted to flash chromatography (10-40% EtOAc-DCM), affording 380 mg (67%) of nucleoside 3 as a white solid: $^1$H (400 MHz, DMSO-d$_6$) δ 8.43 (s, 1H), 7.85-8.02 (m, 6H), 7.46-7.97 (m, 7H), 7.35 (t, J=8.06, 2H), 6.96 (br s, 2H), 6.77 (br s, 1H), 4.54-4.82 (m, 4H), 1.77 (s, 3H); [M+H]$^+$ m/z 627.

Step 2) Preparation of 5-Amino-3-(2'-C-methyl-β-D-ribofuranosyl)-3H-thiazolo[4,5-d]pyrimidin-2-one (4)

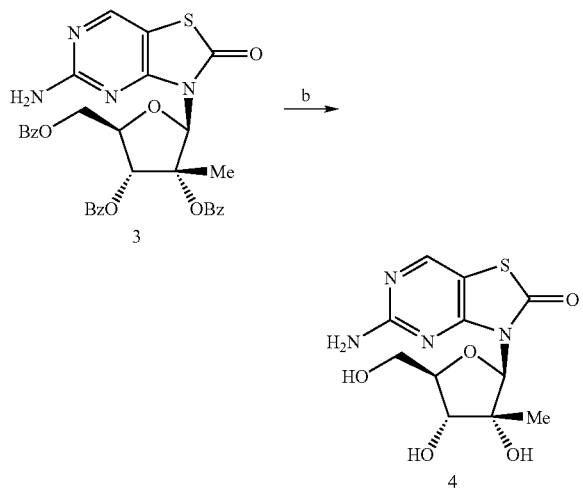

b. K$_2$CO$_3$, MeOH, 10%.

To a suspension of nucleoside 3 (380 mg, 0.606 mmol) in MeOH (20 mL) was added K$_2$CO$_3$ (17 mg, 0.12 mmol) at rt. The resulting mixture was stirred 18 h at rt whereupon it was treated with HOAc (15 μL, 0.25 mmol), concentrated and submitted to HPLC purification (MeCN—H$_2$O), affording 20 mg (10%) of the title compound 4 as a white solid after lyophilization: $^1$H (400 MHz, DMSO-d$_6$) δ 8.33 (s, 1H), 6.86 (br s, 2H), 6.09 (br s, 1H), 5.19 (br s, 1H), 4.88 (br s, 1H), 4.55 (t, J=5.87, 1H), 3.97 (br s, 1H), 3.76-3.81 (m, 1H), 3.61 (br s, 2H), 1.04 (s, 3H); [M+H]$^+$ m/z 315. Analysis calc'd for C$_{11}$H$_{14}$N$_4$O$_5$S.H$_2$O: C, 39.75; H, 4.85; N, 16.86; S, 9.65. Found: C, 40.23; H, 4.76; N, 16.64; S, 9.45.

Example 2

5-Amino-3-(2'-deoxy-β-D-ribofuranosyl)-3H-thiazolo[4,5-d]pyrimidin-2-one

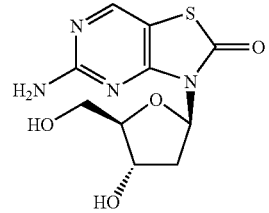

Step 1) Preparation of N'-(7-Chloro-2-oxo-2,3-dihydro-thiazolo[4,5-d]pyrimidin-5-yl)-N,N-dimethylformamidine (7)

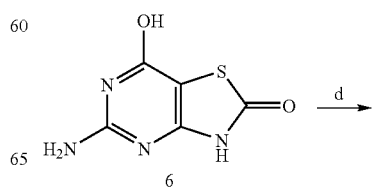

-continued

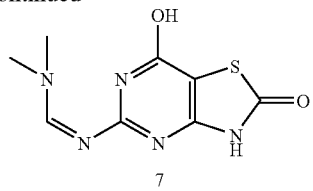

d. SOCl₂, DMF.

To a suspension of 5-amino-7-hydroxy-3H-thiazolo[4,5-d]pyrimidin-2-one (10.0 g, 53.7 mmol) in MeCN (200 mL) at 0° C. was added SOCl₂ (20.0 mL, 274 mmol) dropwise via addition funnel over 20 min. The resulting mixture was slowly warmed to rt then immersed into a 60° C. oil bath where it was stirred for 48 h. The reaction mixture was cooled to rt and slowly poured into 300 g of cracked ice in 300 mL of water containing NaHCO₃ (46 g, 548 mmol). The aqueous mixture was extracted with 20% IPA-DCM (3×500 mL), and the combined organic phases were dried over Na₂SO₄ and concentrated to a residue that was triturated with EtOAc to afford 6.33 g (46%) of chloroamidine 7 as a tan solid: $^1$H (400 MHz, DMSO-d₆) δ 12.60 (s, 1H), 8.69 (s, 1H), 3.25 (s, 3H), 3.11 (s, 3H); [M+H]⁺ m/z 258.

Step 2) Preparation of N'-(7-Chloro-2-oxo-3-[2'-deoxy-3',5'-di-O-(p-toluoyl)-β-D-ribofuranosyl]-2,3-dihydro-thiazolo[4,5-d]pyrimidin-5-yl)-N,N-dimethyl-formamidine (8)

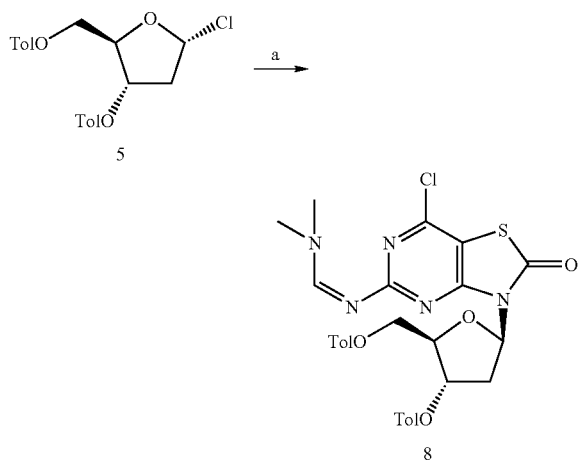

a. 6, NaH, MeCN, 90%.

To a suspension of heterocycle 7 (1.79 g, 6.94 mmol) in anhydrous MeCN (90 mL) at rt was added 95% NaH (183 mg, 7.63 mmol). The resulting mixture was stirred 30 min whereupon chlorosugar 5 (2.70 g, 6.94 mmol) [purchased from Berry & Associates, Inc., Dexter, Mich.] was added. The reaction mixture was heated to 55° C., stirred 1 h, cooled, concentrated, and then submitted to flash chromatography (SiO₂, 5-10% EtOAc-DCM) affording 3.8 g (90%) of nucleoside 8 as a solid material that may be further purified via trituration in MeOH: $^1$H (400 MHz, DMSO-d₆) δ 8.64 (s, 1H), 7.83 (ABq, J$_{AB}$=8.19, Δv$_{AB}$=38.53, 4H), 7.28 (ABq, J$_{AB}$=8.19, Δv$_{AB}$=36.13, 4H), 6.56 (dd, J=8.19, 5.07, 1H), 5.76-5.80 (m, 1H), 4.56-4.60 (m, 1H), 4.45-4.50 (m, 2H), 3.27-3.34 (m, 1H), 3.15 (s, 3H), 3.03 (s, 3H), 2.57-2.64 (m, 1H), 2.35 (s, 3H), 2.39 (s, 3H).

Step 3) Preparation of 5-Amino-3-(2',3'-di-O-(p-toluoyl)-β-D-ribofuranosyl)-3H-thiazolo[4,5-d]pyrimidin-2-one (9)

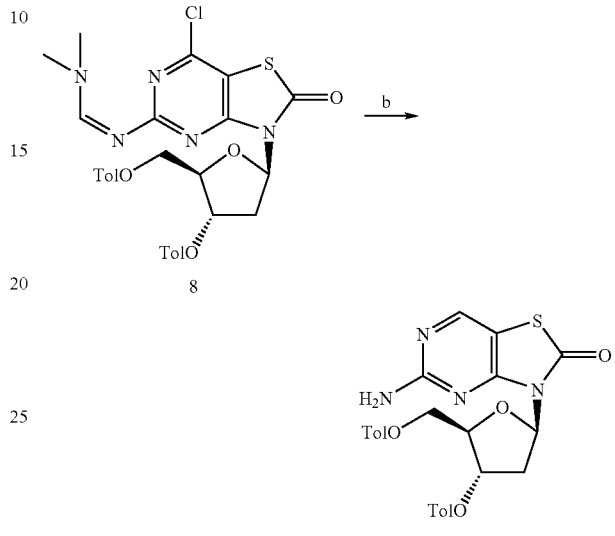

b. Zn—Cu, HOAc, 67%.

To a solution of chloroaryl nucleoside 8 (924 mg, 1.47 mmol) in acetic acid (10.4 mL) at rt was added Zn—Cu couple (1.54 g, 11.9 mmol). The resulting suspension was stirred vigorously at ambient temperature for 3.5 h, filtered through celite, and then concentrated to a solid material that was submitted to flash chromatography (SiO₂, 0-10% EtOAc—CHCl₃), yielding 520 mg (67%) of compound 9 as a tan solid: $^1$H NMR (400 MHz, d₆-DMSO) δ 8.34 (s, 1H), 7.85 (ABq, J$_{AB}$=8.4, Δv$_{AB}$=17.6, 4H), 7.30 (ABq, J$_{AB}$=8.4, Δv$_{AB}$=27.1, 4H), 6.87 (s, 2H), 6.47 (m, 1H), 5.78 (m, 1H), 4.62 (m, 1H), 4.47 (m, 2H), 3.35 (m, 2H), 2.38 (s, 3H), 2.35 (s, 3H).

Step 4) Preparation of 5-Amino-3-(2'-deoxy-β-D-ribofuranosyl)-3H-thiazolo[4,5-d]pyrimidin-2-one (10)

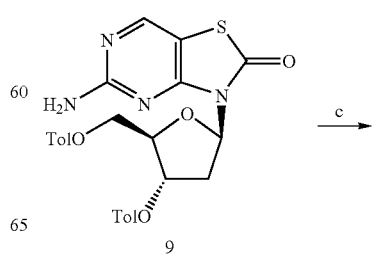

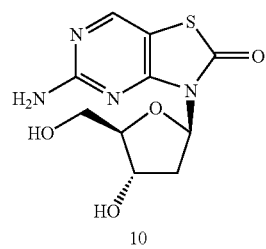

c. K$_2$CO$_3$, MeOH, 46%.

To a suspension of diester 9 (300 mg, 0.577 mmol) from Step 3 (above) in MeOH (20 mL) at rt was added K$_2$CO$_3$ (188 mg, 1.36 mmol). The resulting mixture was stirred 8 h whereupon it was quenched with HOAc (164 µL, 2.86 mmol), then concentrated and submitted to HPLC (MeCN—H$_2$O, TFA) to afford 75 mg (46%) of the title compound 10 as a white solid (TFA salt) after lyophilization: $^1$H (400 MHz, DMSO-d$_6$) δ 8.34 (s, 1H), 7.15 (br s, 2H), 6.33 (t, J=7.0, 1H), 4.33 (br s, 1H), 3.72-3.73 (m, 1H), 3.39-3.56 (m, 2H), 2.89-2.96 (m, 1H), 1.99-2.05 (m, 1H); [M+H]$^+$ m/z 285. Analysis calc'd for C$_{10}$H$_{12}$N$_4$O$_4$S.C$_2$HF$_3$O$_2$: C, 36.18; H, 3.29; N, 14.31; S, 8.05. Found: C, 36.28; H, 3.35; N, 13.96; S, 8.05.

Example 3

5-Amino-3-(2'-O-acetyl-3'-deoxy-β-D-ribofuranosyl)-3H-thiazolo[4,5-d]pyrimidin-2-one (15)

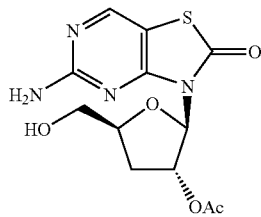

Step 1) Preparation of 5-Amino-3-(2',5'-di-O-benzoyl-3'-deoxy-β-D-ribofuranosyl)-3H-thiazolo[4,5-d]pyrimidin-2-one (12)

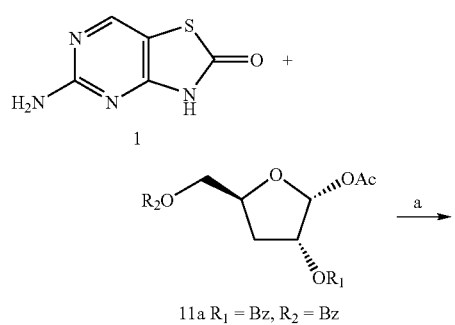

11a R$_1$ = Bz, R$_2$ = Bz

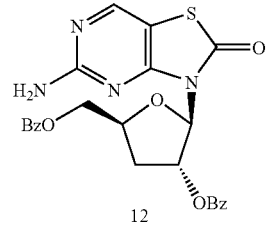

a. 11a, BSA, MeCN, rt; TMSOTf, 80° C., 78%.

To a heterogeneous mixture of heterocycle 1 (25.0 g, 0.149 mol) and deoxyribofuranose 11a (47.0 g, 0.122 mol) [may be prepared from the corresponding methyl ribofuranoside (Walton, et. al. *J. Med. Chem.* 1965, 8, 659-663) via the method of Valdivia, et. al. *Tetrahedron Lett.* 2005, 46, 6511-6514] in anhydrous MeCN (640 mL) at RT was added dropwise via addition funnel BSA (113 mL, 0.458 mol) over 20 min. The resultant suspension was treated dropwise with TMSOTf (41.5 mL, 0.229 mol) at rt over 20 min, whereupon it became nearly homogeneous. The mixture was heated to reflux (internal T 83° C.) and stirred for 8 h, then cooled to rt and concentrated to an oily residue via rotary evaporation. The residue was dissolved in EtOAc (500 mL) and cooled to 10° C. where it was slowly treated with 1 M pH 7 phosphate buffer (400 mL), keeping the internal temperature below 35° C. Upon completed addition of buffer, the pH of the mixture was adjusted to 7.0 with solid K$_2$HPO$_4$ and vigorous stirring was continued for 1 h. Celite (25 g) was added, and the mixture stirred an additional 30 min. Filtration of the triphasic mixture through a short pad of celite provided two clear phases. The aqueous phase was saturated with solid NaCl then extracted with EtOAc (4×250 mL). The combined organic phases were washed with brine (400 mL), dried over Na$_2$SO$_4$ and charcoal (1 g), and then filtered through a short pad of SiO$_2$. The clear amber filtrate was concentrated to dryness, whereupon solid heterocycle had precipitated. The residue was taken up in DCM, treated with a small amount of MgSO$_4$, and then filtered through celite. The clear filtrate was concentrated and further dried under high vacuum at 35° C. to provide a tan, crispy foam (69.5 g). Submission of this solid foam to flash chromatography (SiO$_2$, 5-40% EtOAc-hexanes) afforded 46.3 g (77%) of nucleoside 12 as a light beige solid foam: $^1$H NMR (DMSO-d$_6$) δ 8.35 (s, 1H), 7.93-8.01 (m, 4H), 7.61-7.69 (m, 2H), 7.47-7.56 (m, 4H), 6.94 (s, 2H), 6.09 (d, J=1.9, 1H), 6.00 (d, J=7.4, 1H), 4.64-4.69 (m, 1H), 4.57 (dd, J=12.1, 2.7, 1H), 4.36 (dd, J=12.1, 5.8, 1H), 2.92-3.00 (m, 1H), 2.32 (dd, J=14.0, 5.8, 1H); [M+H]$^+$ m/z 493.

Step 2) Preparation of 5-Amino-3-(3'-deoxy-β-ribofuranosyl)-3H-thiazolo[4,5-d]pyrimidin-2-one (13)

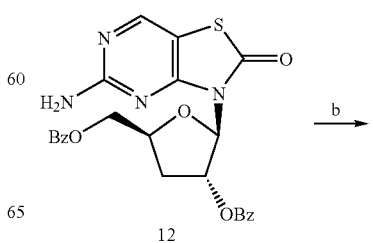

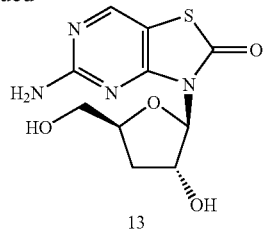

13 b. K₂CO₃, MeOH, 78%.

To a heterogeneous mixture of dibenzoate 12 (46.3 g, 94.0 mmol) and anhydrous MeOH (1.0 L) was added K₂CO₃ (2.59 g, 18.8 mmol) at rt. The mixture became homogeneous within 30 min, then heterogeneous again within 3 h. Additional MeOH (100 mL) was added to increase fluidity, and the reaction mixture was stirred for a total of 24 h. The suspension was treated with HOAc (2.26 mL, 39.5 mmol) and then concentrated at 45° C. whereupon it was cooled, then triturated with EtOH (200 mL) and ether (1800 mL) for 1 h. The solid material was filtered, washed with ether (3×250 mL), air dried and then washed with water (2×250 mL), affording 19.47 g (78%) of diol 13 as a white solid that was dried in vaccuo and recrystallized from water: $^1$H NMR (DMSO-d₆) δ 8.31 (s, 1H), 6.82 (s, 2H), 5.82 (d, 1H), 5.41 (d, 1H), 4.79-4.83 (m, 1H), 4.65 (t, J=5.8, 1H), 4.13-4.20 (m, 1H), 3.40-3.49 (m, 2H), 2.31 (ddd, J=16.0, 9.4, 7.0, 1H), 1.81 (ddd, J=12.5, 5.8, 2.3, 1H); [M+H]⁺ m/z 285. Analysis calc'd for $C_{10}H_{12}N_4O_4S$: C, 42.25; H, 4.25; N, 19.71; S, 11.28. Found: C, 42.36; H, 4.32; N, 19.72; S, 11.23.

Step 3) Preparation of 5-Amino-3-(2',5'-di-O-acetyl-3'-deoxy-β-D-ribofuranosyl)-3H-thiazolo[4,5-d]pyrimidin-2-one (14)

$C_{14}H_{16}N_4O_6S$: C, 45.65; H, 4.38; N, 15.21; S, 8.70. Found: C, 45.69; H, 4.52; N, 15.02; S, 8.64.

Alternatively diacetate 14 may be prepared from heterocycle 1 and deoxyribo-furanose 11b [may be prepared via the method of Valdivia, et. al. Tetrahedron Lett. 2005, 46, 659-663] in a manner similar to Step 1 above with a yield of 63%.

Step 4) Preparation of 5-Amino-3-(2'-O-acetyl-3'-deoxy-β-D-ribofuranosyl)-3H-thiazolo[4,5-d]pyrimidin-2-one (15)

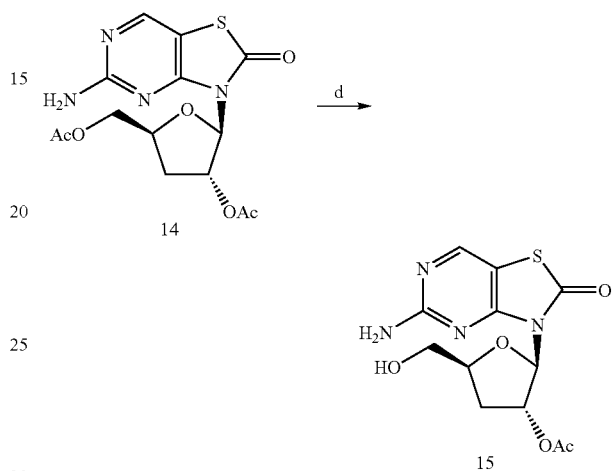

d. Candida Arctica, Acetone, pH 7 buffer 91%.

To a slowly stirring suspension of diacetate 14 (5.08 g. 13.8 mmol) and Candida Arctica lipase acrylic resin (2.50 g) [purchased from Sigma] in acetone (50 mL) was added 50 mM pH 7 phosphate buffer (250 mL) at rt. The resulting mixture was stirred slowly for 18 h whereupon it was filtered, concentrated

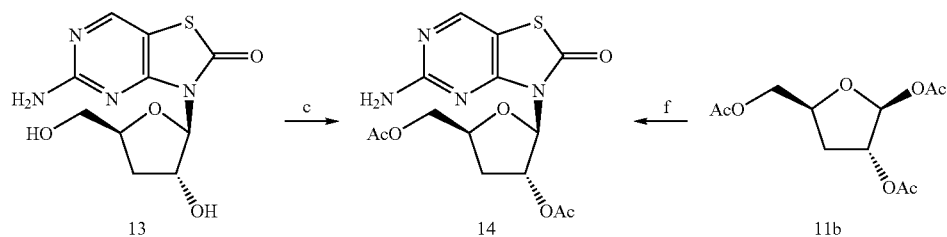

c. Ac₂O, Et₃N, DMAP, MeCN. f. 1, BSA, MeCN, rt; TMSOTf, 80° C.

To a suspension of diol 13 (8.00 g, 28.1 mmol), Et₃N (11.8 mL, 84.4 mmol), and DMAP (344 mg, 2.81 mmol) in anhydrous MeCN (190 mL) at 0° C. was added dropwise Ac₂O (5.44 mL, 57.7 mmol). The resultant mixture, that became homogeneous within 1.5 h, was slowly warmed to rt and stirred for 18 h whereupon it was concentrated to a residue that was submitted to flash chromatography (SiO₂, 0-100% EtOAc-DCM) to afford 8.34 g (80%) of diacetate 14 as a white solid foam that may be further purified via trituration with ether-hexanes: $^1$H (400 MHz, DMSO-d₆) δ 8.34 (s, 1H), 6.91 (s, 2H), 5.90 (d, J=1.9, 1H), 5.65 (d, J=7.4, 1H), 4.33-4.39 (m, 1H), 4.25 (dd, J=12.1, 3.1, 1H), 4.01 (dd, J=11.7, 6.6, 1H), 2.65-2.73 (m, 1H), 2.06 (dd, J=13.6, 6.2, 1H), 2.05 (s, 3H), 1.98 (s, 3H); [M+H]⁺ m/z 369. Analysis calc'd for and extracted with EtOAc (4×250 mL). The combined organic phases were dried over Na₂SO₄, concentrated and then submitted to flash chromatography (SiO₂, 0-15% IPA-DCM) to afford 4.11 g (91%) of the title compound 15 as a white solid that may be further purified via trituration with ether-hexanes: $^1$H (400 MHz, DMSO-d₆) δ 8.33 (s, 1H), 6.87 (s, 2H), 5.88 (d, J=2.3, 1H), 5.66 (d, J=7.8, 1H), 4.76 (t, J=5.8, 1H), 4.11-4.18 (m, 1H), 3.43-3.53 (m, 2H), 2.50-2.57 (m, 1H), 2.05 (s, 3H), 1.98 (dd, J=13.6, 5.8, 1H); [M+H]⁺ m/z 327. Analysis calc'd for $C_{12}H_{14}N_4O_5S$: C, 44.17; H, 4.32; N, 17.17; S, 9.83. Found: C, 44.12; H, 4.45; N, 16.88; S, 9.69.

Example 4

5-Amino-3-(2'-O-acetyl-5'-O-benzoyl-3'-deoxy-β-D-ribofuranosyl)-3H-thiazolo[4,5-d]pyrimidin-2-one (16)

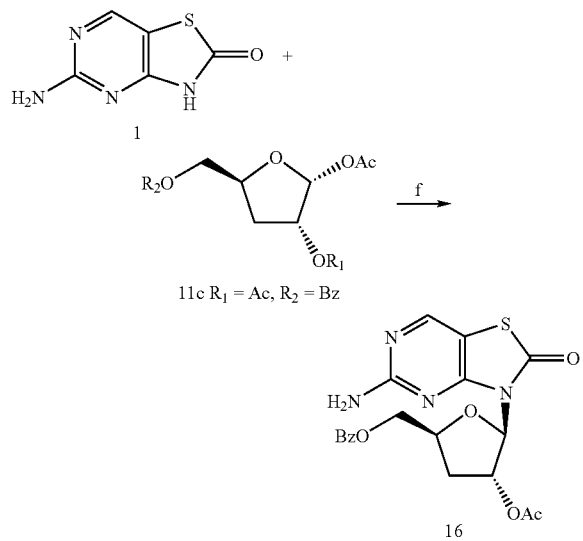

11c R₁ = Ac, R₂ = Bz f. 11c, BSA, MeCN, rt; 80° C.

To a heterogeneous mixture of heterocycle 1 (106 mg, 0.633 mmol) and deoxyribofuranose 11c [purchased from Berry & Associates, Inc., Dexter, Mich.] (183 mg, 0.57 mmol) in anhydrous MeCN (8 mL) was added BSA (464 uL, 1.89 mmol) at rt. The resultant mixture was immersed into a 60° C. oil bath and stirred for 4 h. The mixture was concentrated via rotary evaporation and partitioned between EtOAc (100 mL) and saturated NaHCO₃ (50 mL). The organic phase was dried over Na₂SO₄ and then concentrated. The crude material was triturated with Et₂O-EtOAc to afford 132 mg (54%) of an off-white solid that was submitted to HPLC (MeCN—H₂O) to provide an analytical sample: ¹H (400 MHz, DMSO-d₆) δ 8.33 (s, 1H), 7.91-7.94 (m, 2H), 7.60-7.65 (m, 1H), 7.47-7.50 (m, 2H), 6.94 (s, 2H), 5.93 (d, J=1.8, 1H), 5.72 (dd, J=5.9, 1.5, 1H), 4.50-4.53 (m, 2H), 4.31 (q, J=7.0, 1H), 2.80-2.88 (m, 1H), 2.14 (dd, J=13.2, 5.1, 1H), 2.07 (s, 3H); [M+H]⁺ m/z 431.

Example 5

5-Amino-3-benzyl-3H-thiazolo[4,5-d]pyrimidin-2-one (18)

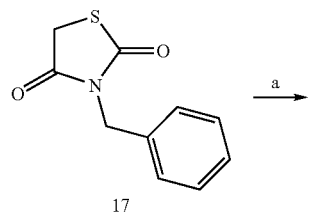

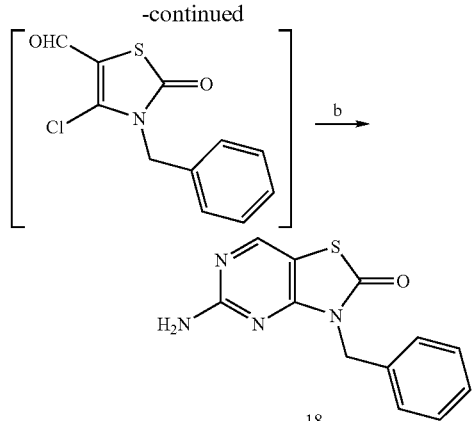

a. POCl₃, DMF, 90° C. b. Guanidine HCl, NaOMe, MeOH, 19% over 2 steps

To POCl₃ (8.09 mL, 86.8 mmol) at 0° C. was added consecutively solid 3-benzyl-thiazolidine-2,4-dione [prepared according to the method of Lo, et. al. *J. Org. Chem.* 1957, 999-1001] and DMF. The reaction mixture was stirred 5 min, then transferred to a 90° C. oil bath where it was stirred 3 h. The dark mixture was poured into ice (100 g) and water (100 mL), and then extracted with EtOAc (3×100 mL). The combined organic phases were dried over MgSO₄ then filtered through celite, concentrated, taken up in DCM, filtered through a short pad of SiO₂ and finally concentrated to a dark oil that was used without further purification.

Guanidine hydrochloride (8.87 g, 92.8 mmol) was added as solid to 25% NaOMe-MeOH (18 mL, 79.6 mmol) in MeOH (48 mL) at −5° C. The resulting mixture was stirred 5 min and then treated with crude chloroaldehyde [from above] as a solution in MeOH (20 mL). The reaction mixture was placed into a 90° C. oil bath, concentrated by distillation of the MeOH over 2 h, and then heated an additional 30 min. The residue was taken up in EtOAc (200 mL) and partitioned with 1 N HCl (100 mL). The aqueous phase was treated with solid NaHCO3 and partitioned with EtOAc (3×100 mL). The combined organic phases from the alkaline extraction were dried over Na₂SO₄ and then concentrated to a residue that was submitted to chromatography (SiO₂, 50-70% EA-DCM), affording 1.4 g (19%) of the title compound 18 as a white solid: ¹H (400 MHz, DMSO-d₆) δ 8.32 (s, 1H), 7.24-7.34 (m, 5H), 6.83 (s, 2H), 5.01 (s, 2H); [M+H]⁺ m/z 259.

Example 6

5-Amino-3-(3',3'-C,O-dimethyl-β-D-ribofuranosyl)-3H-thiazolo[4,5-d]pyrimidin-2-one (23)

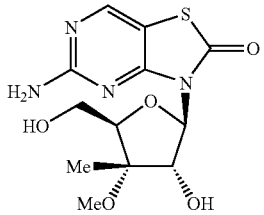

Step 1) Preparation of 1,2-O-Isopropylidene-3-methyl-3-O-methyl-5-O-trityl-α-D-ribofuranose (20)

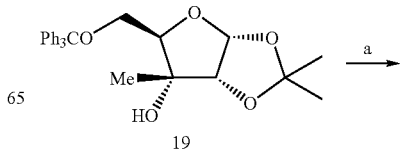

-continued

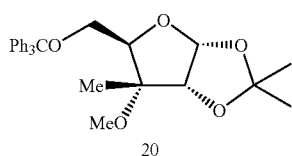

a. KH (xs), dioxane, DMF (3:1); MeI, rt, 72 h, 87%

To a mixture of tertiary alcohol 19 (716 mg, 1.60 mmol) [prepared according to the method of Just et. al. *Tetrahedron Lett.* 2000, 41, 9223-9227] in anhydrous dioxane (6 mL) was added an excess of KH (30% dispersion in mineral oil) at rt. The resulting mixture was stirred 1 h and was then treated with MeI (2 mL, 32 mmol), producing a copious precipitate. DMF (2 mL) was added to keep the reaction mixture fluid enough for stirring over 72 h. The mixture was diluted with EtOAc (100 mL) and partitioned with saturate aqueous NaHCO$_3$ (50 mL). The organic phase was dried over Na$_2$SO$_4$, concentrated and submitted to flash chromatography (SiO$_2$, 10-60% EtOAc-hexanes), affording 640 mg of methyl ether 20 as a white solid: $^1$H (400 MHz, DMSO-d$_6$) δ 7.22-7.35 (m, 15H), 5.72 (d, J=2.9, 1H), 4.30 (d, J=2.9, 1H), 4.07 (dd, J=7.7, 2.6, 1H), 3.14 (s, 3H), 2.92-3.05 (m, 2H), 1.51 (s, 3H), 1.28 (s, 3H), 0.82 (s, 3H).

Step 2) Preparation of 1,2,5-tetra-O-Acetyl-3,3-C,O-dimethyl-β-D-ribofuranose (21)

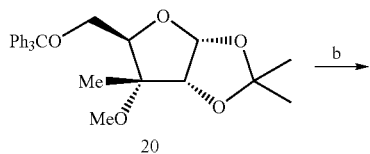

b. HOAc, Ac$_2$O, H$_2$SO$_4$, rt, 33%.

To a solution of HOAc (50.0 mL) and Ac$_2$O (3.83 mL, 40.6 mmol) was added furanose 20 (3.62 g, 8.11 mmol). To this colorless solution was added 1 M H$_2$SO$_4$ in HOAc (0.41 mL, 0.41 mmol), resulting in an intensely yellow colored solution. The solution was stirred at rt for 16 hr, and then concentrated via rotary evaporation. The excess HOAc was azeotroped via several volumes of toluene. The residue was dissolved in DCM (100 mL) and washed with saturated NaHCO$_3$ (30 mL). The organic layer was dried over Na$_2$SO$_4$, decanted, and concentrated to an oily heterogenous mixture. This mixture was subjected to flash chromatography (SiO$_2$, 5-35% EtOAc-hexanes) affording 0.78 g (33%) of triacetate 21 as a pale yellow oil: $^1$H (400 MHz, DMSO-d$_6$) δ 5.91 (d, J=2.0, 1H), 5.07 (d, J=2.4, 1H), 4.29 (dd, J=3.2, 12.0, 1H), 4.15 (dd, J=3.2, 7.2, 1H), 3.96 (dd, J=6.8, 12.0, 1H), 3.17 (s, 31H), 2.10 (s, 31H), 2.04 (s, 6H), 1.33 (s, 3H).

Step 3) Preparation of 5-Amino-3-(2',5'-di-O-acetyl-3',3'-C,O-dimethyl-β-D-ribofuranosyl)-3H-thiazolo[4,5-d]pyrimidin-2-one (22)

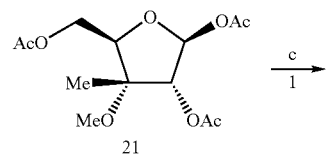

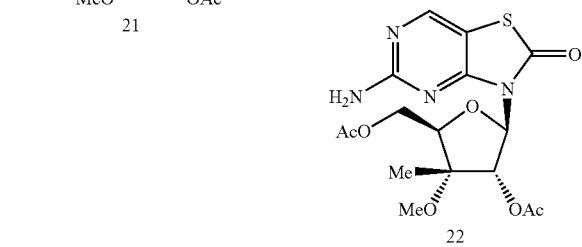

c. BSA, MeCN, rt; TMSOTf, 80° C., 65%.

To a mixture of heterocycle 1 in anhydrous MeCN (5.0 mL) was added dropwise BSA (0.52 mL, 2.11 mmol) at rt. The resulting mixture was immersed in a 40° C. oil bath, and stirred for 90 min whereupon it became homogenous. Furanose 21 (0.20 g, 0.73 mmol) was added followed by TMSOTf (158.4 µL, 0.88 mmol). The reaction mixture was then immersed in an 80° C. oil bath and heated for 2 hr. The reaction was cooled to rt, and partitioned between 1 M pH 7 phosphate buffer (15 mL) and EtOAc (30 mL). The resulting emulsion was filtered through a pad of celite yielding two distinct layers. The organic layer was separated and dried over Na$_2$SO$_4$, filtered, and concentrated in vacuo to a dark orange brown residue. This residue was submitted to flash chromatography (SiO$_2$, 5-50% EtOAc-hexanes) purification affording 0.30 g (59%) of nucleoside 22 as a finely divided pale yellow solid: $^1$H (400 MHz, DMSO-d$_6$) δ 8.34 (s, 1H), 6.90 (br s, 2H), 6.11 (dd, J=8.0, 27.6, 2H), 4.3-4.17 (m, 3H), 2.75 (s, 3H), 2.02 (s, 3H), 2.01 (s, 3H), 1.35 (s, 3H); [M+H]$^+$ m/z 413.

Step 4) Preparation of 5-Amino-3-(3',3'-C,O-dimethyl-β-D-ribofuranosyl)-3H-thiazolo[4,5-d]pyrimidin-2-one (23)

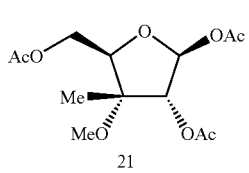

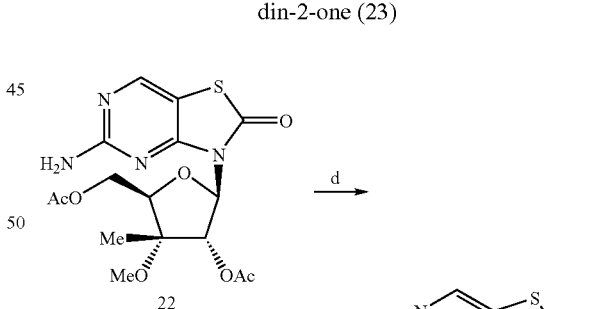

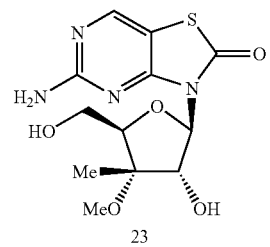

d. K$_2$CO$_3$, MeOH, rt.

Nucleoside 22 (230 mg, 0.56 mmol) was dissolved in 5.6 mL MeOH. Solid K$_2$CO$_3$ (15.4 mg, 0.11 mmol) was added µl, 0.28 mmol) was added and the reaction stirred for 30 min, and then concentrated mixture to dryness in vacuo. The residual yellow solids were triturated with Et₂O (3×10 mL) carefully decanting filtrates via pipette. The solid material was then washed with H₂O (3×5 mL), rinsed with Et₂O (2×5 mL) and dried on house vacuum 24 h to obtain 76.4 mg (42%) of a finely divided white solid: ¹H (400 MHz, DMSO-d₆) δ 8.35 (s, 1H), 6.83 (br s, 2H), 5.93 (d, J=8.58, 1H), 5.24 (d, J=7.02, 1H), 4.95 (t, J=7.4, 1H), 4.57 (t, J=5.46, 1H), 3.95 (t, J=5.07, 1H), 3.46-3.58 (m, 2H), 3.26 (s, 3H), 1.29 (s, 3H); [M+H]⁺ m/z 329.

Example 7

5-Amino-3-(5'-O-Acetyl-2'-O-[2"-O-acetylpropyl]-3-methyl-β-D-ribofuranosyl)-3H-thiazolo[4,5-d]pyrimidin-2-one (27)

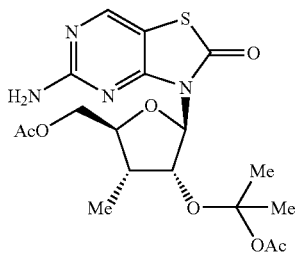

Step 1) Preparation of 1,2-O-Isopropylidine-3-methyl-5-O-trityl-α-D-ribofuranose (25)

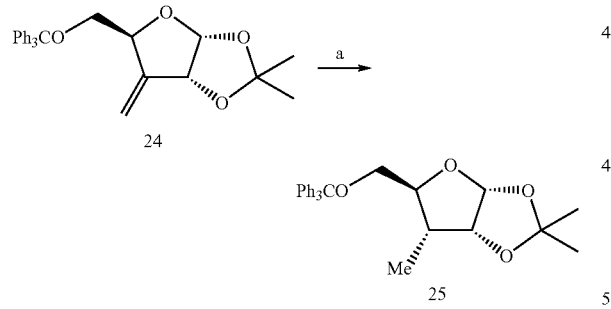

a. H₂, 5% Pd/C, EtOAc, rt, 48 hr, 6:1 (α/β), 78%.

To a solution of 24 (2.40 g, 5.60 mmol) [prepared according to Bera, et. al. *Helvetica Chimica Acta* 2000, 83(7), 1398-1407] dissolved in EtOAc (50 mL), under a blanket of N₂, was added 5% Pd/C (240 mg). The flask was charged with H₂ at 1 atm, and stirred at rt for 72 h. The reaction mixture was filtered through celite, and concentrated in vacuo to a clear colorless oil. Flash chromatography purification (SiO₂, 0-40% EtOAc-hexanes) afforded 1.88 g of 25 (78%) as a 6:1 (α/β) mixture of isomers: ¹H (400 MHz, DMSO-d₆) δ 7.22-7.38 (m, 15H), 7.63 (d, J=3.2, 1H), 4.53 (t, J=4.0, 1H), 3.67 (dq, J=2.8, 1.6, 1H), 3.18 (dd, J=3.2, 10.4, 1H), 2.99 (dd, J=5.2, 10.8, 1H), 1.89-1.98 (m, 1H), 1.38 (s, 3H), 1.24 (s, 3H), 0.81 (d, J=6.8, 3H).

Step 2) Preparation of 1,5-di-O-Acetyl-2-O-(2'-O-acetylpropyl)-3-methyl-β-D-ribofuranose (26)

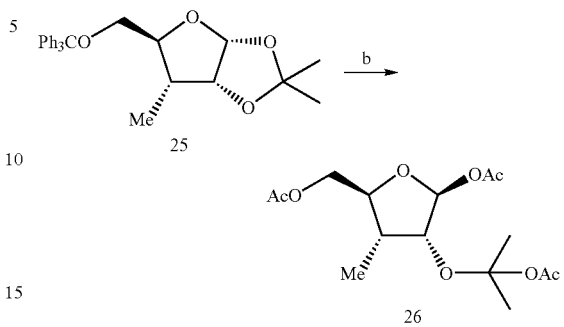

b. HOAc, Ac₂O, H₂SO₄, rt, 19%.

In a manner similar to Step 3 of Example 6, 25 was converted to 26 in a 19% yield. The crude residue was submitted to flash chromatography (SiO₂, 2-30% EtOAc-hexanes), yielding a 5:1 (β/α) mixture of anomers (tainted with triphenylmethane) by ¹H NMR (DMSO-d₆) that was used without further purification in the next step: ¹H (400 MHz, DMSO-d₆) δ 6.07 (d, J=2.8, 1H), 5.02 (ddd, J=6.8, 6.8, 2.8, 1H), 4.25 (dd, J=12.0, 3.2, 1H), 4.06-4.21 (m, 2H), 2.14-2.23 (m, 1H), 2.03 (s, 3H), 2.00 (s, 3H), 1.99 (s, 3H), 1.41 (s, 3H), 1.39 (s, 3H), 0.91 (d, J=6.8, 3H).

Step 3) Preparation of 5-Amino-3-(5'-O-Acetyl-2'-O-[2"-O-acetylpropyl]-3-methyl-β-D-ribofuranosyl)-3H-thiazolo[4,5-d]pyrimidin-2-one (27)

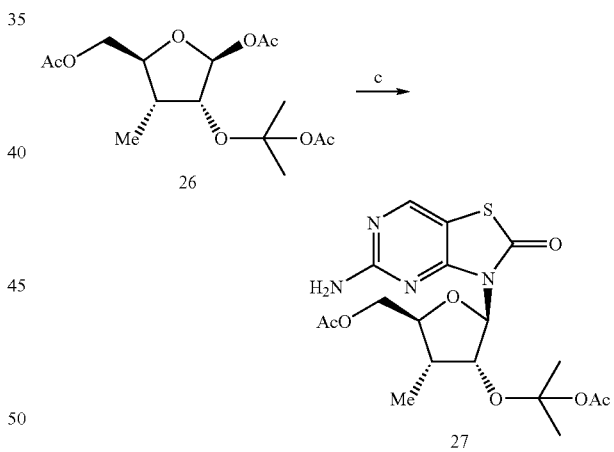

c. BSA, MeCN, rt; TMSOTf, 60° C., 11%.

To a mixture of the heterocycle 1 in anhydrous MeCN (5.0 mL) at rt was added dropwise BSA (0.52 mL, 2.11 mmol). The resulting mixture stirred for 30 min, and then furanose 26 (0.20 g, 0.73 mmol) was added followed by TMSOTf (158.4 μL, 0.88 mmol). The reaction mixture was immersed in a 60° C. oil bath, whereupon it became a homogenous solution. Stirring was continued for 2.5 h. The reaction mixture was cooled to rt, then partitioned between 1M pH 7 phosphate buffer and EtOAc. The mixture was filtered through a pad of celite and the distinct layers were separated. The organic phase was dried over Na₂SO₄, filtered, concentrated and submitted to flash chromatography (SiO₂, 5-50% EtOAc-hexanes), affording 30.0 mg of the title compound 27 as a white solid: $^1$H (400 MHz, DMSO-$d_6$) δ 8.36 (s, 1H), 6.90 (s, 2H), 6.09 (d, J=7.2, 1H), 5.16 (t, J=7.2, 1H), 4.88 (dt, J=6.4, 3.2 1H), 4.20 (dd, J=3.2, 12.0, 1H), 4.08 (dd, J=6.4, 12.0, 1H), 2.28 (dq, J=6.8, 14, 1H), 1.97 (s, 3H), 1.87 (s, 3H), 1.54 (s, 3H), 1.41 (s, 3H), 0.86 (d, J=6.8, 3H); [M+H]$^+$ m/z 441.

Example 8

5-Amino-3-(3'-methyl-β-D-ribofuransyl)-3H-thiazolo[4,5-d]pyrimidin-2-one (30)

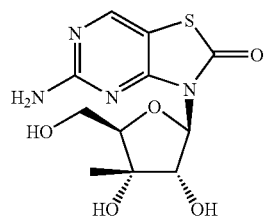

Step 1) Preparation of 5-Amino-3-(3'-O-acetyl-2',5'-di-O-benzoyl-3'-methyl-β-D-ribofuranosyl)-3H-thiazolo[4,5-d]pyrimidin-2-one (29)

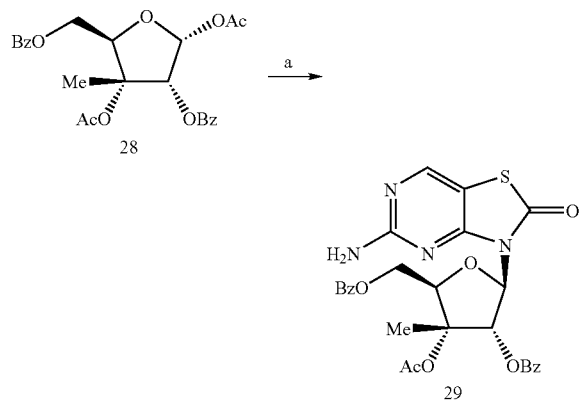

a. Heterocycle 1, BSA, TMSOTf, CH$_3$CN, 88%.

5-Amino-3H-thiazolo[4,5-d]pyrimidin-2-one (123 mg, 0.733 mmol), 3'-C-methyl-ribofuranose 28 [prepared according to the method of Wang et al. *J. Med. Chem.* 2000, 43, 3704-3713] (302 mg, 0.66 mmol), BSA (447 mg, 2.2 mmol) and MeCN (8 mL) were mixed vigorously for 30 min until a homogeneous solution was obtained. The reaction was then charged with TMSOTf (0.186 mL, 1.1 mmol) and placed into a preheated oil bath at 65° C. After 3 h the reaction was cooled to rt and the solvent was removed by rotary evaporation. The resultant solid was dissolved in EtOAc (200 mL) and extracted by saturated aqueous NaHCO$_3$ (2×100 mL). The organic phase was dried with Na$_2$SO$_4$ and concentrated. The crude product was submitted to flash chromatography (SiO$_2$, 0 to 40% EtOAc—CHCl$_3$), yielding 365 mg (88%) of a tan solid: $^1$H NMR (400 MHz, d$_6$-DMSO) δ 8.38 (s, 1H), 7.92 (d, J=6.4, 4H), 7.69 (m, 2H), 7.53 (m, 4H), 6.93 (br s, 2H), 6.90 (s, 1H), 6.43 (d, J=7.2, 1H), 6.10 (t, J=9.2, 1H), 4.80 (br s, 1H), 4.59 (br, s, 1H), 2.09 (s, 3H), 1.97 (s, 3H); [M+H]$^+$ m/z 565.

Step 2) Preparation of 5-Amino-3-(3'-methyl-β-D-ribofuransyl)-3H-thiazolo[4,5-d]pyrimidin-2-one (30)

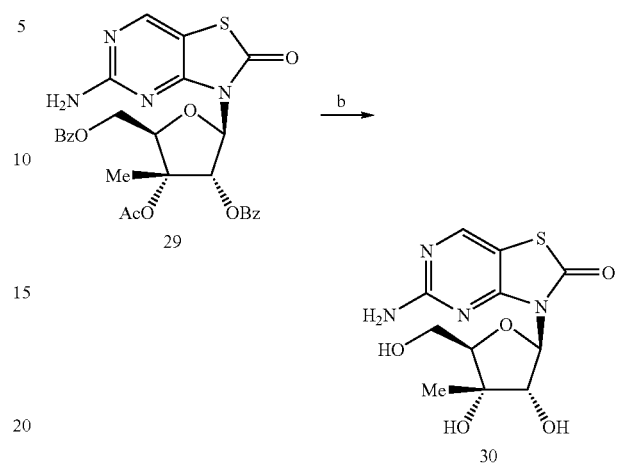

b. K$_2$CO$_3$, MeOH, 66%.

5-Amino-3-(2',5'-di-O-benzoyl-3'-O-acetyl-3'-C-methyl-β-D-ribofuransyl)-3H-thiazolo[4,5-d]pyrimidin-2-one (365 mg, 0.647 mmol) was dissolved in MeOH (10 mL). K$_2$CO$_3$ (17.9 mg, 0.129 mmol) was added, and the reaction was stirred for 16 h at rt. Acetic acid (15.5 mg, 0.258 mmol) was added, and the reaction was concentrated via rotary evaporation. The crude product was then submitted to HPLC purification (MeCN—H$_2$O), yielding 135 mg (66%) of a solid material: $^1$H NMR (400 MHz, d$_6$-DMSO) δ 8.35 (s, 1H), 6.82 (br s, 2H), 5.91 (d, J=8.0, 1H), 5.38 (d, J=6.4, 1H), 4.81 (t, J=6.0, 1H), 4.68 (s, 1H), 4.51 (t, J=5.6, 1H), 3.78 (t, J=5.6, 1H), 3.48-3.53 (m, 2H), 1.21 (s, 3H); [M+H]$^+$ m/z 315. Analysis calc'd for C$_{11}$H$_{14}$N$_4$O$_5$S.0.5H$_2$O: C, 40.86; H, 4.68; N, 17.33; S, 9.92. Found: C, 40.78; H, 4.90; N, 16.94; S, 9.87.

Example 9

Preparation of 5-amino-2,3-dihydro-2-thioxo-3-β-D-ribofuranosyl-thiazolo[4,5-d]pyrimidin-7(6H)-one (33)

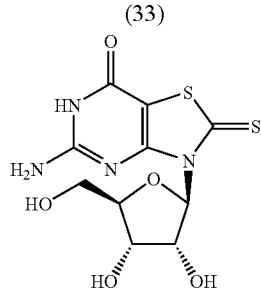

Step 1) Preparation of 5-amino-2,3-dihydro-2-thioxo-3-(2',3',5'-tri-O-acetyl-β-D-ribofuranosyl)thiazolo[4,5-d]pyrimidin-7-(6H)-one (32)

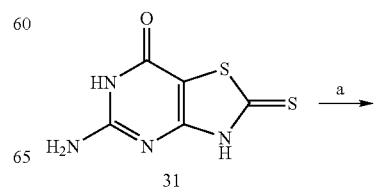

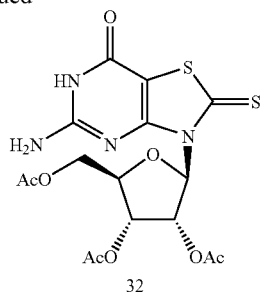

32 a. BSA, TAR, MeCN, 60° C.; TMSOTf, 60° C., 80%.

Heterocycle 31 [prepared according to the method of Robins et. al. *J. Med. Chem.* 1990, 33, 407-415] (150 mg, 0.75 mmol), TAR (214 mg, 0.675 mmol), MeCN (10 mL) and BSA (0.55 mL, 2.25 mmol) were combined and heated for 1 h at 60° C. The reaction was then charged with TMSOTf (250 mg, 1.13 mmol) and stirred for 16 h at 60° C. The mixture was concentrated via rotary evaporation, and the crude solid was dissolved in EtOAc (20 mL). This organic phase was then extracted with saturated aqueous NaHCO$_3$ (2×10 mL), and concentrated to dryness by rotary evaporation. Trituration of the residue with Et$_2$O (10 mL) yielded 200 mg (80%) of a solid material that was further purified via HPLC (MeCN—H$_2$O) to generate an analytically pure sample: $^1$H NMR (400 MHz, d$_6$-DMSO) δ 11.54 (s, 1 H), 7.04 (br s, 2H), 6.59 (m, 1H), 6.10 (m, 1H), 5.70 (t, J=7.2, 1H), 4.42 (dd, J=12.0, 3.2, 1H), 4.27 (m, 1H), 4.18 (m, 1H), 2.08 (s, 3H), 2.05 (s, 3H), 1.99 (s, 3H); [M+H]$^+$ m/z 459. Analysis calc'd for C$_{16}$H$_{18}$N$_4$O$_8$S$_2$: C, 41.92; H, 3.96; N, 12.22; S, 13.99. Found: C, 41.78; H, 3.99; N, 12.02; S, 13.72.

Step 2) Preparation of 5-amino-2,3-dihydro-2-thioxo-3-β-D-ribofuranosyl-thiazolo[4,5-d]pyrimidin-7(6H)-one (33)

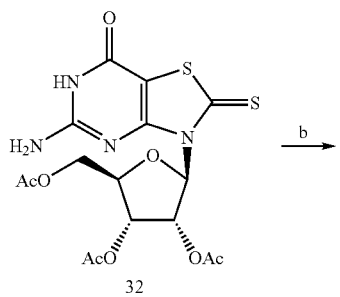

b. K$_2$CO$_3$, MeOH, rt, 66%.

Nucleoside triester 32 (100 mg, 0.21 mmol) and K$_2$CO$_3$ (42.7 mg, 0.31 mmol) were dissolved in MeOH (5 mL) and stirred for 16 h at ambient temperature. To this mixture was added HOAc (37 mg, 0.62 mmol) and the solvent was removed via rotary evaporation. The residue were then submitted to HPLC purification (MeCN—H$_2$O) yielding 47 mg (66%) of a solid: $^1$H NMR (400 MHz, d$_6$-DMSO) δ 11.66 (s, 1H), 6.91 (br s, 2H), 6.47 (s, 1H), 5.31 (d, J=5.2, 1H), 4.94 (s, 1H), 4.78 (s, 2H), 4.27 (d, J=8.0, 1H), 3.78 (m, 1H), 3.69 (m, 1H), 3.52 (m, 1H); [M+H]$^+$ m/z 333. Analysis calc'd for C$_{10}$H$_{12}$N$_4$O$_5$S$_2$·0.5TFA·0.75H$_2$O·0.25MeCN: C, 33.43; H, 3.60; N, 14.41. Found: C, 33.11; H, 3.73; N, 14.80.

Example 10

5-amino-2,3-dihydro-2-thioxo-3-(2',3',5'-tri-O-acetyl-β-D-xylofuranosyl)thiazolo[4,5-d]pyrimidin-7-(6H)-one (34)

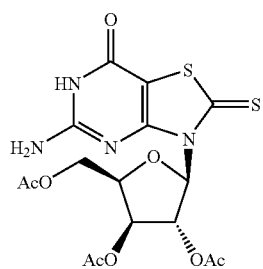

34

Preparation of 5-amino-2,3-dihydro-2-thioxo-3-(2',3',5')-tri-O-acetyl-β-D-xylofuranosyl)thiazolo[4,5-d]pyrimidin-7-(6H)-one (34)

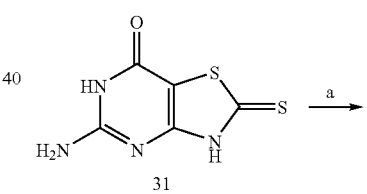

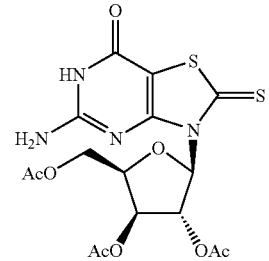

34 a. BSA, tetraacetylxylofuranose, MeCN, 60° C., 30 min; TMSOtf, 4 h, 15%.

Heterocycle 31 (265.3 mg, 1.33 mmol), tetraacetylxylofuranose (380 mg, 1.19 mmol), BSA (1.26 mL, 5.32 mmol) and MeCN (10 ml) is heated to 60° C. for 30 minutes. Then the reaction was charged with TMSOTf (0.36 mL, 2.0 mmol). After 4 h the reaction was worked up by removing the solvent by rotary vacuum and taking up the crude solid in ethyl acetate (15 mL). This organic phase was then extracted with saturated sodium bicarbonate (2×10 mL). The organic phase was concentrated and the crude solid was triturated in 1:1

EtOAc-hexanes. The solid was collected and submitted to HPLC purification (MeCN—H$_2$O) yielding 40 mg (15%): $^1$H NMR (400 MHz, d$_6$-DMSO) δ 11.45 (s, 1H), 6.90 (br s, 2H), 6.49-6.58 (m, 1H), 6.35-6.49 (m, 1H), 5.58 (d, J=5.6, 1H), 4.55 (s, 1H), 4.31 (m, 2H), 2.11 (m, 3H), 1.99 (m, 3H), 1.98 (m, 3H); [M+H]$^+$ m/z 459. Analysis calc'd for C$_{16}$H$_{18}$N$_4$O$_8$S$_2$: C, 41.92; H, 3.96; N, 12.22; S, 13.99. Found: C, 42.14; H, 3.99; N, 12.11; S, 14.01.

Example 11

5-Amino-3-β-D-ribofuranosyl-3H-thiazolo-[4,5-d]pyrimidin-2-thione (39)

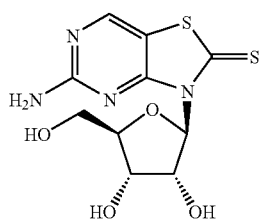

Step 1) Preparation of 5-Amino-3H-thiazolo[4,5-d]pyrimidine-2-thione (37)

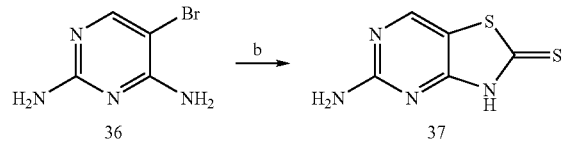

b. O-Ethylxanthic acid potassium salt, DMF, 30%.

5-Bromo-pyrimidine-2,4-diamine (2.0 g, 10.58 mmol) [prepared in a manner similar to English et. al. J. Am. Chem. Soc. 1946, 68, 453-458] and O-ethylxanthic acid potassium salt (3.39 g, 21.16 mmol) was heated in DMF (25 mL) to 140° C. After 5 h the reaction was cooled to ambient temperature and 25 mL of water was added. The pH was then adjusted to 5.0 using 1 N HCl. A red precipitate formed and was collected by filtration, yielding 900 mg (30%) of a solid: $^1$H NMR (400 MHz, d$_6$-DMSO) δ 13.85 (s, 1H), 8.33 (br s, 1H), 6.90 (s 2H).

Step 2) Preparation of 5-Amino-3-(2',3',5'-tri-O-acetyl-β-D-ribofuranosyl)-3H-thiazolo[4,5-d]pyrimidin-2-thione (38)

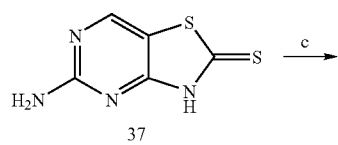

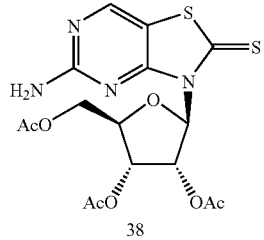

c. TAR, BSA, CH$_3$CN, TMSOTf, 57%.

5-Amino-3H-thiazolo[4,5-d]pyrimidine-2-thione (250 mg, 1.36 mmol), TAR (389 mg, 1.22 mmol) and BSA (1.0 mL, 4.08 mmol) was heated to 60° C. in acetontrile (10 mL). After 30 minutes the reaction was charged with TMSOTf (0.37 mL, 2.04 mmol) and the reaction was allowed to progress for 16 h. The solvent was then removed via rotary evaporation, and the crude product re-dissolved in EtOAc (15 mL). The organic phase was extracted with concentrated aqueous NaHCO$_3$ (2×10 mL). The organic phase was then concentrated again and submitted to flash chomatography (SiO$_2$, 5% MeOH-EtOAc) yielding 301 mg (57%) of white solid: $^1$H NMR (400 MHz, d$_6$-DMSO) δ 8.49 (s, 1H), 7.08 (br s, 2H), 6.65 (s 1H), 6.12 (m, 1H), 5.79 (t, J=8.0, 1H), 4.43 (dd, J=12.0, 3.6, 1H), 4.28-4.34 (m, 1H), 4.17 (dd, J=11.6, 6.8, 1H), 2.09 (s, 3H), 2.05 (s, 3H), 1.97 (s, 3H); [M+H]$^+$ m/z 443.

Step 3) Preparation of 5-Amino-3-O-D-ribofuranosyl-3H-thiazolo-[4,5-d]pyrimidin-2-thione (39)

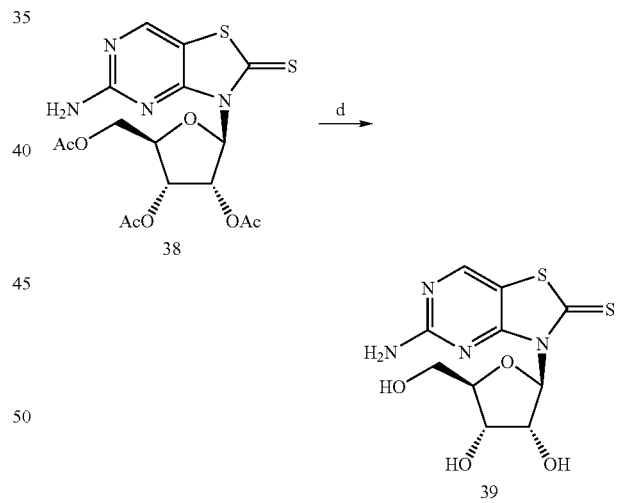

d. K$_2$CO$_3$, MeOH, 74%.

5-Amino-3-(2',3',5'-tri-O-acetyl-β-D-ribofuranosyl)-3H-thiazolo[4,5-d]pyrimidin-2-thione (202 mg, 0.46 mmol) was dissolved in MeOH (5 mL), and K$_2$CO$_3$ (18.9 mg, 0.14 mmol) was added. After 1 h acetic acid (21 mg, 0.28 mmol) was added, and the reaction was concentrated via rotary evaporation. The crude solid was then submitted to HPLC purification (MeCN—H$_2$O), yielding 108 mg (74%) of white solid: $^1$H NMR (400 MHz, d$_6$-DMSO) δ 8.45 (s, 1H), 6.96 (br s, 2H), 6.53 (d, J=4.4, 1H), 5.33 (d, J=6.0, 1H), 5.03 (m, 1H), 4.86 (d, J=6.4, 1H), 4.67 (t, J=6.0, 1H), 4.33 (m, 1H), 3.79 (m, 1H), 3.70 (m, 1H), 3.53 (m, 1H). Analysis calc'd for $C_{10}H_{12}N_4O_4S_2 \cdot 0.35H_2O$: C, 37.22; H, 3.97; N, 17.36; S, 19.87. Found: C, 37.64; H, 3.87; N, 17.02; S, 19.39.

Example 12

5-Amino-3-β-D-xylofuranosyl-3H-thiazolo-[4,5-d]pyrimidin-2-thione (41)

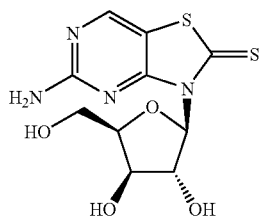

Step 1) Preparation of 5-Amino-3-(2',3',5'-tri-O-acetyl-β-D-xylofuranosyl)-3H-thiazolo[4,5-d]pyrimidin-2-thione (40)

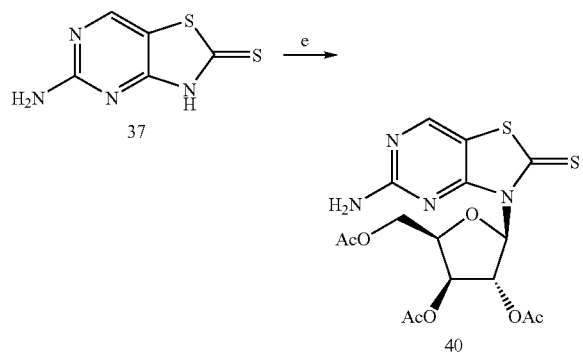

e. Tetraacetylxylofuranose, BSA, MeCN, TMSOTf, 13%.

5-Amino-3H-thiazolo[4,5-d]pyrimidine-2-thione (237 mg, 1.28 mmol), tetra-acetylxylose (370 mg, 1.16 mmol) and BSA (1.25 mL, 5.12 mmol) were heated in MeCN (10 mL) to 60° C. for 30 min. To this was added TMSOTf (347 μL, 1.92 mmol), and the reaction mixture was stirred at 60° C. for 16 h, whereupon the solvent was removed by rotary evaporation, and the crude solid was re-dissolved in EtOAc (15 mL). This organic phase was then extracted with concentrated NaHCO$_3$ (2×10 mL), and then concentrated to a solid residue that was submitted to flash chromatography (0-100% EtOAc—CHCl$_3$) yielding 67 mg (13%) of tan solid: $^1$H NMR (400 MHz, d$_6$-DMSO) δ 8.51 (s, 1H), 6.90 (br s, 2H), 6.67 (d, J=4.0, 1H), 6.49 (t, J=2.0, 1H), 5.62 (m, 1H), 5.63 (m, 1H), 4.37 (m, 1H), 4.21 (br m, 1H), 2.18 (s, 3H), 1.97 (s, 3H), 1.94 (s, 3H); [M+H]$^+$ m/z 443.

Step 2) Preparation of 5-Amino-3-β-D-xylofuranosyl-3H-thiazolo-[4,5-d]pyrimidin-2-thione (41)

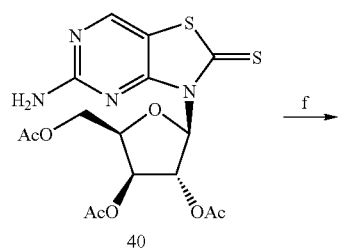

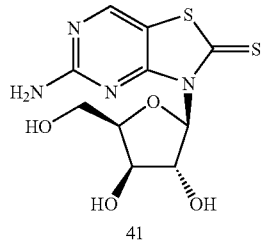

f. K$_2$CO$_3$, MeOH, 62%.

5-Amino-2,3-dihydro-2-thioxo-3-(2,3,5-tri-O-acetyl-β-D-xylofuranosyl)thiazolo[4,5-d]pyrimidin-7-thione (65 mg, 0.14 mmol) is dissolved in MeOH (5 mL). To this was added K$_2$CO$_3$ (19 mg, 0.137 mmol), and the resultant mixture was stirred for 3 h whereupon it was quenched with HOAc (140 μL, 2.4 mmol), and the solvent was removed by rotary evaporation. The crude product is submitted to HPLC purification (MeCN—H$_2$O) yielding 30 mg (62%) of white solid: $^1$H NMR (400 MHz, d$_6$-DMSO) δ 8.50 (s, 1H), 6.90 (br s, 2H), 6.45 (d, J=5.2, 1H), 5.67 (d, J=8.0, 1H), 5.49 (d, J=8.4, 1H), 5.03 (m, 1H), 4.49 (t, J=5.2, 1H), 4.02 (m, 2H), 3.72 (m, 2H). Analysis calc'd for $C_{10}H_{12}N_4O_4S_2 \cdot 0.4H_2O$: C, 37.12; H, 3.99; N, 17.32; S, 19.82. Found: C, 37.53; H, 3.80; N, 17.04; S, 19.42.

Example 13

5-Amino-7-ethoxy-3-(2',5'-di-O-acetyl-3'-deoxy-β-D-ribofuranosyl)-3H,6H-thiazolo[4,5-d]pyrimidine-2-one (43)

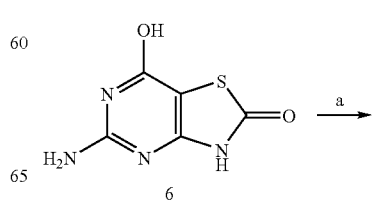

Step 1) Preparation of 5-Amino-7-hydroxy-3-(2',5'-di-O-acetyl-3'-deoxy-β-D-ribofuranosyl)-3H,6H-thiazolo[4,5-d]pyrimidine-2-one (42)

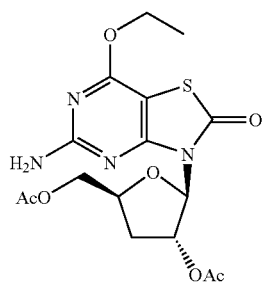

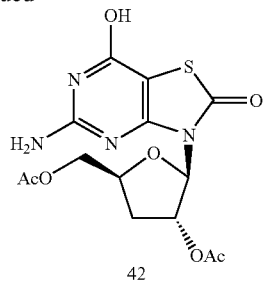

42 a. 1,2,5-tri-O-acetyl-b-D-ribofuranose, BSA, MeCN, 40° C.; TMSOTf, 80° C.

To a mixture of heterocycle 6 (4.60 g, 25.00 mmol) in anhydrous MeCN (83.0 mL) was added dropwise BSA (15.28 mL, 62.49 mmol). The reaction was then immersed in a 40° C. oil bath and stirred for 90 min, and 1,2,5-tri-O-acetyl-β-D-ribofuranose (5.42 g, 20.80 mmol) was added followed by TMSOTf (5.65 mL, 31.24 mmol). The resulting thick mixture was immersed in an 80° C. oil bath whereupon the mixture clarified to a homogenous solution after 15 min. The reaction was stirred for 2 h at 80° C., cooled to rt, and then partitioned between 1 M pH 7 phosphate buffer (50 mL) and EtOAc (100 mL). The resulting emulsion was filtered through a pad of celite yielding two distinct layers that were separated. The organic layer was dried over $Na_2SO_4$, filtered, and concentrated in vacuo to a residue. This residue was submitted to flash chromatography ($SiO_2$, 0-6% MeOH-DCM) affording 3.41 g (43%) of nucleoside 42 as a finely divided pale yellow solid: $^1$H (400 MHz, DMSO-$d_6$) δ 11.22 (s, 1H), 6.95 (br s, 2H), 5.79 (d, J=2.0, 1H), 5.59 (d, J=7.2, 1H), 4.20-4.34 (m, 1H), 4.22 (dd, J=3.2, 12.0, 1H), 3.99 (dd, J=6.4, 11.6, 1H), 2.57-2.67 (m, 1H), 2.05 (s, 3H), 1.99 (s, 3H), 1.97-2.03 (m, 1H); [M+H]$^+$ m/z 385. Analysis calc'd for $C_{14}H_{16}N_4O_7S$: C, 43.75; H, 4.20; N, 14.58; S, 8.34. Found: C, 43.64; H, 4.31; N, 14.37; S, 8.19.

Step 1) Preparation of 5-Amino-7-ethoxy-3-(2',5'-di-O-acetyl-3'-deoxy-β-D-ribofuranosyl)-3H,6H-thiazolo[4,5-d]pyrimidine-2-one (43)

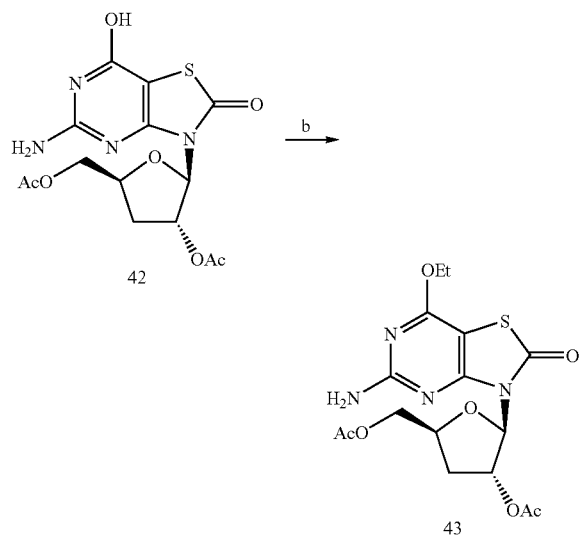

b. EtOH, S-TPP, DEAD, THF, rt, 20%.

To a solution of 42 (99 mg, 0.26 mmol) dissolved in anhydrous THF (5.5 mL) was added S-TPP PPh$_3$ resin (0.36 g, 0.77 mmol, 2.15 mmol/g). The mixture was chilled to 0° C., and EtOH (30.1 μL, 0.52 mmol) was added followed by DEAD (176.0 μL, 0.39 mmol). The reaction mixture was removed from the ice bath and warmed to rt whereupon it stirred for 16 h. The mixture was concentrated in vacuo to a residue that was subjected to several passes of flash chromatography purification ($SiO_2$, elution with 2% MeOH/0-40% EtOAc in hexanes) affording 0.22 mg of 43 (20%): $^1$H (400 MHz, DMSO-$d_6$) δ 6.95 (br s, 2H), 5.87 (d, J=2.4, 1H), 5.64 (d, J=7.2, 1H), 4.39 (q, J=6.8, 2H), 4.32-4.4 (m, 1H), 4.25 (dd, J=3.2, 11.6, 1H), 3.96-4.03 (m, 1H), 2.63-2.71 (m, 1H), 2.05 (s, 3H), 2.03-2.08 (m, 1H), 1.99 (s, 3H), 1.30 (t, J=6.8, 3H); [M+H]$^+$ m/z 413.

Example 14

5-Amino-7-ethoxy-3-(β-D-ribofuranosyl)-2,3-dihydro-2-thioxo-thiazolo[4,5-d]pyrimidin-7(6H)-one (45)

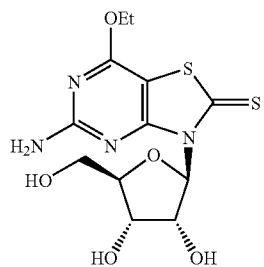

45

Step 1) Preparation of 5-Amino-7-ethoxy-3-(2',3',5'-tri-O-acetyl-β-D-ribofuranosyl)-2,3-dihydro-2-thioxo-thiazolo[4,5-d]pyrimidin-7(6H)-one (44)

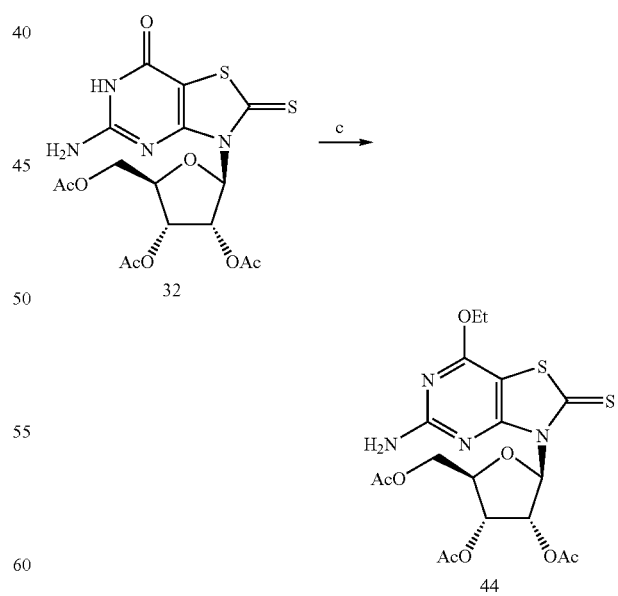

c. S-TPP, Ethanol, DEAD, THF, 65%.

5-Amino-2,3-dihydro-2-thioxo-3-(2,3,5-tri-O-acetyl-β-D-ribofuranosyl)thiazolo[4,5-d]pyrimidin-7(6H)-one (250 mg, 0.54 mmol) and S-TPP Ph$_3$P resin (753 mg, 1.62 mmol)

were suspended in THF (15 mL) and cooled to 0° C. Ethyl alcohol (50 μL, 1.08 mmol) and DEAD (148 μL, 0.82 mmol) were added sequentially. After 1 h the reaction mixture was warmed to ambient temperature and stirred for 16 h. The reaction mixture was then filtered, concentrated and submitted to flash chromatography (SiO$_2$, 15% EtOAc—CHCl$_3$), affording 200 mg (65%) of a white foam: $^1$H NMR (400 MHz, d$_6$-DMSO) δ 6.91 (s, 1H), 6.47 (br s, 2H), 6.29 (m, 1H), 6.18 (s, 1H), 4.62-4.31 (m, 5H), 1.42 (t, J=4.2. 3H), 1.38 (s, 3H), 1.35 (s, 3H), 1.32 (s, 3H); [M+H]$^+$ m/z 487.

Step 2) Preparation of 5-Amino-7-ethoxy-3-β-D-ribofuranosyl-2,3-dihydro-2-thioxo-thiazolo[4,5-d]pyrimidin-7(6H)-one (45)

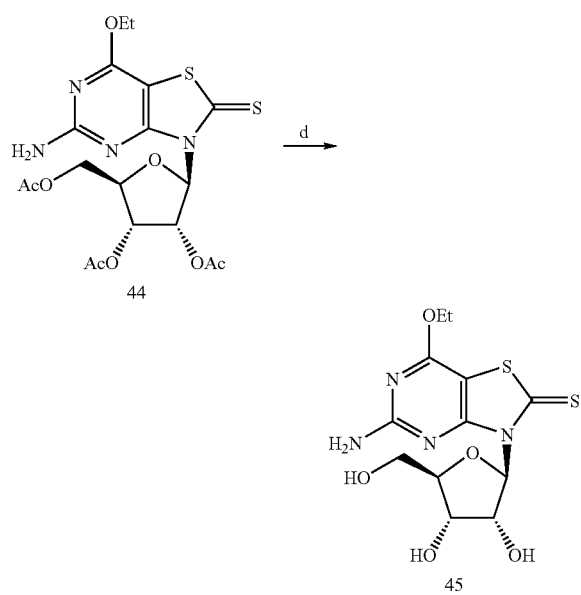

d. K$_2$CO$_3$, MeOH, 83%.

5-Amino-2,3-dihydro-2-thioxo-3-(2,3,5-tri-O-acetyl-β-D-ribofuranosyl)thiazolo-[4,5-d]pyrimidin-7(6H)-ethyl ether (180 mg, 0.37 mmol) and K$_2$CO$_3$ (12.8 mg, 0.01 mmol) were suspended in MeOH (5 mL). After 1 h acetic acid was added and the solvent removed rotary evaporation. The crude product was then submitted to HPLC purification (MeCN—H$_2$O) yielding 105 mg (83%) of a solid: $^1$H NMR (400 MHz, d$_6$-DMSO) δ 6.98 (s, 2H), 6.50 (d, J=4.8, 1H), 5.32 (d, J=5.2, 1H), 5.01 (s, 1H), 4.85 (d, J=5.6, 1H), 4.68 (t, J=5.6, 1H), 4.43 (dd, J=13.6, 6.8, 2H), 4.30 (m, 1H), 3.80 (m, 1H), 3.71 (m, 1H), 3.66 (m, 1H), 1.31 (t, J=6.8, 3H); [M+H]$^+$ m/z 361.

Preparation of 5-Amino-3H-oxazolo[4,5-d]pyrimidin-2-one (50)

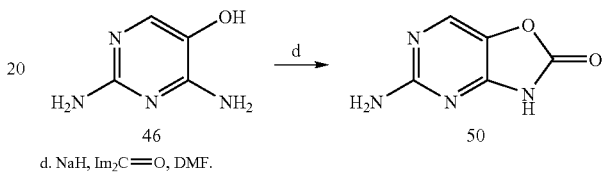

d. NaH, Im$_2$C=O, DMF.

2,4-Diamino-pyrimidin-5-ol (500 mg, 3.97 mmol) [prepared according to the method of Hull. *J. Chem. Soc.* 1956, 2033-2035] was suspended in DMF (10 mL). To this was added consecutively NaH (86.7 mg, 3.77 mmol) and CDI (707 mg, 4.36 mmol), and the reaction mixture was heated with vigorous stirring at 60° C. for 3 h. The mixture was cooled to ambient temperature, and then quenched with water (25 mL). The solvent and water were removed via rotary evaporation, and the residue was then triturated in water (5 mL). The solid was then collected by filtration and dried, affording 230 mg (38%): $^1$H NMR (400 MHz, d$_6$-DMSO) δ 11.90 (br s, 1H), 7.72 (br s, 1H), 6.72 (s, 2H); Analysis calc'd for C$_5$H$_4$N$_4$O$_2$.0.2H$_2$O: C, 38.56; H, 2.85; N, 35.98. Found: C, 39.01; H, 2.71; N, 35.58; [M+H]$^+$ m/z 153.

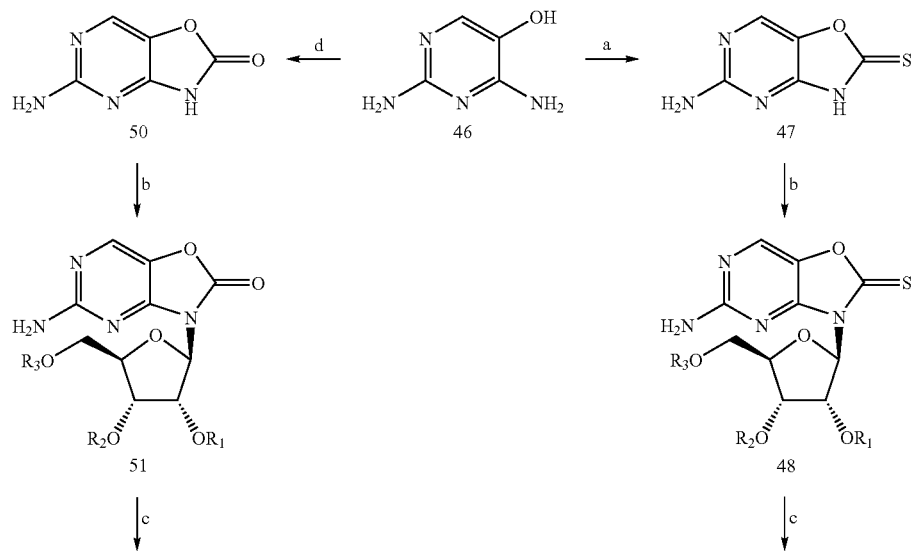

-continued

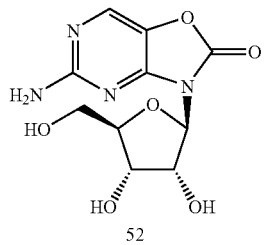

52

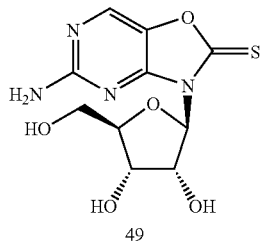

49 a. NaH, Im₂C═S, DMF. b. BSA, appropriate β-D-ribofuranose, MeCN, rt; TMSOTf, 80° C. c. K₂CO₃, MeOH, rt. d. NaH, Im₂C═O, DMF.

The diaminohydroxypyrimidine 46 was reacted with NaH and CDI in DMF to afford heterocycle 50, or with NaH and TCDI in DMF to provide heterocycle 47. Both aminopyrimidines 47 and 50 can be independently submitted to BSA-TMSOTf mediated coupling reactions with an appropriately selected β-D-ribofuranose (wherein $R_1$, $R_2$ and $R_3$ may be independently acetyl or benzoyl) to give nucleosides 48 and 51 respectively. Alkaline methanolysis of 48 and 51 should afford deprotected nucleosides 49 and 52 respectively.

Scheme 1

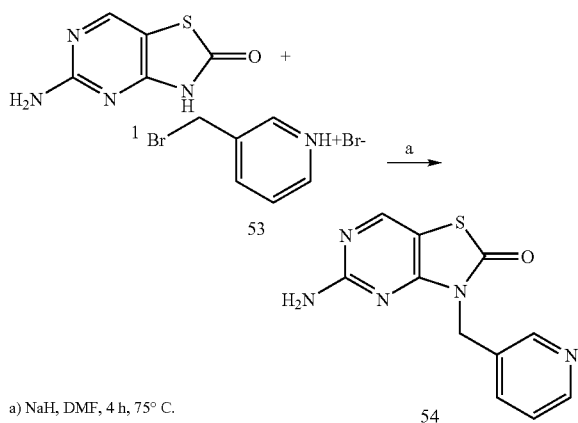

a) NaH, DMF, 4 h, 75° C.

Example 15

Preparation of 5-Amino-3-pyridin-3-ylmethyl-3H-thiazolo[4,5-d]pyrimidin-2-one (54)

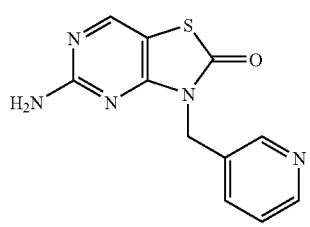

54

Step 1: Preparation of 5-Amino-3-pyridin-3-ylmethyl-3H-thiazolo[4,5-d]pyrimidin-2-one (54)

5-Amino-3H-thiazolo[4,5-d]pyrimidin-2-one (107 mg, 0.64 mmol) was dissolved in DMF (4 mL) at ambient temperature. Sodium hydride (30 mg, 1.32 mmol) was added and the mixture was heated to 30° C. Stirring was continued for 0.5 h before 3-bromomethyl-pyridine hydrobromide (179 mg, 0.71 mmol) was added. The mixture was then heated to 75° C. and allowed to stir for 4 h. Upon completion, the reaction was allowed to cool to room temperature, then concentrated. Water (12 mL) was added. The resulting mixture was diluted with H₂O (12 mL), then extracted with ethyl acetate (3×5 mL). The combined organic layers were washed with brine, dried over Na₂SO₄, filtered, and concentrated. The crude material was purified by column chromatography (SiO₂, 20-50% EtOAc—CH₂Cl₂) to generate 90 mg (54%) of 54 as a white solid: ¹H NMR (400 MHz, DMSO-d₆) δ 8.59 (s, 1H), 8.48 (d, J=3.6, 1H), 8.32 (s, 1H), 7.71 (d, J=8.4, 1H), 7.36 (m, 1H), 6.86 (s, 2H), 5.04 (s, 2H); [M+H]⁺ 260.1.

Example 16

Preparation of 5-Amino-3-(6-chloro-pyridin-3-ylmethyl)-3H-thiazolo[4,5-d]pyrimidin-2-one (55)

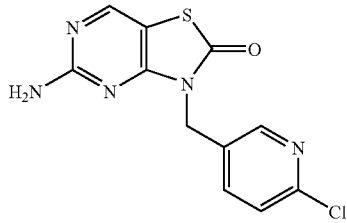

Step 1: Preparation of 5-Amino-3-(6-chloro-pyridin-3-ylmethyl)-3H-thiazolo[4,5-d]pyrimidin-2-one (55)

In a manner similar to Example 15, Step 1, 111 mg of the title compound 55 was generated in 54% yield as an orange solid: ¹H NMR (400 MHz, DMSO-d₆) δ 8.42 (s, 1H), 8.30 (s, 1H), 7.77 (d, J=8.8, 1H), 7.47 (d, J=8.0, 1H), 6.85 (s, 2H), 5.11 (s, 2H); [M+H]⁺ 294.1.

Example 17

Preparation of (Z)-5-Amino-3-(4-chloro-2-buten-1-yl)-3H-thiazolo[4,5-d]pyrimidin-2-one (56)

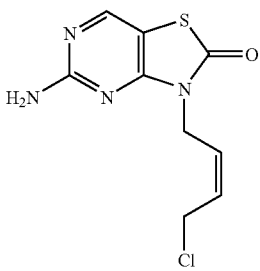

Step 1: Preparation of (Z)-5-Amino-3-(4-chloro-2-buten-1-yl)-3H-thiazolo[4,5-d]pyrimidin-2-one (56)

In a manner similar to Example 15, Step 1, 74 mg of the title compound 56 was generated in 46% yield as a yellow solid:

$^1$H NMR (400 MHz, DMSO-d$_6$) δ 8.29 (s, 1H), 6.80 (s, 2H), 5.81 (m, 1H), 5.66 (m, 1H), 4.53 (d, J=6.0, 2H), 4.27 (d, J=8.0, 2H); [M+H]$^+$ 257.2.

Example 18

Preparation of 5-Amino-3-hexyl-3H-thiazolo[4,5-d]pyrimidin-2-one (57)

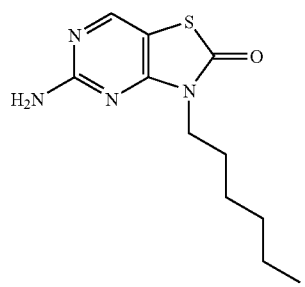

57

Step 1: Preparation of 5-Amino-3-hexyl-3H-thiazolo[4,5-d]pyrimidin-2-one (57)

In a manner similar to Example 15, Step 1, 51 mg of the title compound 57 was generated in 15% yield as an off-white solid: $^1$H NMR (400 MHz, DMSO-d$_6$) δ 8.28 (s, 1H), 6.78 (s, 1H), 3.82 (t, J=7.2, 2H), 1.64 (m, 2H), 1.27 (m, 6H), 0.85 (t, J=6.8, 3H); [M+H]$^+$] 253.1.

Example 19

Preparation of (±)-5-Amino-3-cyclopentyl-3H-thiazolo[4,5-d]pyrimidin-2-one (58)

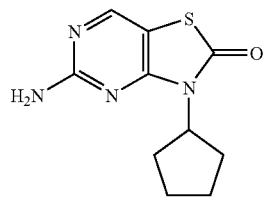

58

Step 1: Preparation of (±)-5-Amino-3-cyclopentyl-3H-thiazolo[4,5-d]pyrimidin-2-one (58)

In a manner similar to Example 15, Step 1, 21 mg the title compound 58 was generated in 5% yield as a light yellow solid: $^1$H NMR (400 MHz, CDCl$_3$) δ 8.09 (s, 1H), 5.23 (s, 2H), 2.24 (m, 1H), 2.00 (m, 4H), 1.66 (m, 4H); [M+H]$^+$ 237.0.

Example 20

Preparation of 5-Amino-3-(4-nitro-phenyl)-3H-thiazolo[4,5-d]pyrimidin-2-one (59)

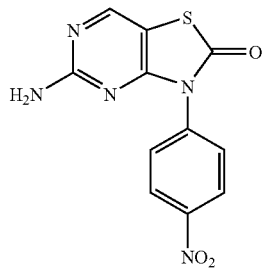

59

Step 1: Preparation of 5-Amino-3-(4-nitro-phenyl)-3H-thiazolo[4,5-d]pyrimidin-2-one (59)

In a manner similar to Example 15, Step 1, 45 mg of the title compound 59 was generated in 10% yield as an orange solid: $^1$H NMR (400 MHz, DMSO-d$_6$) δ 8.59 (s, 1H), 8.18 (d, J=9.2, 2H), 7.99 (d, J=9.2, 2H), 5.74 (s, 2H); [M+H]$^+$ 290.2.

Example 21

5-Amino-3-(2,3,5,6-tetrafluoro-pyridin-4-yl)-3H-thiazolo[4,5-d]pyrimidin-2-one (60)

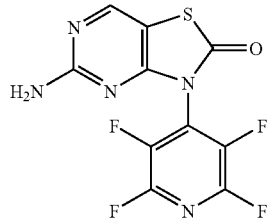

60

Step 1: Preparation of 5-Amino-3-(2,3,5,6-tetrafluoro-pyridin-4-yl)-3H-thiazolo[4,5-d]pyrimidin-2-one (60)

In a manner to Example 15, Step 1, 35 mg of the title compound 60 was generated in 5% yield as an orange solid: $^1$H NMR (400 MHz, DMSO-d$_6$) δ 8.16 (s, 1H), 4.01 (s, 2H); [M+H]$^+$ 318.4.

Scheme 2

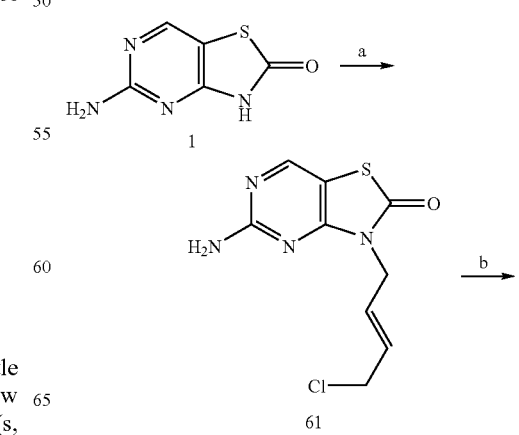

85

-continued

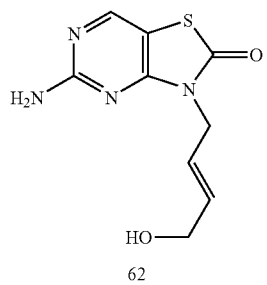

62 a) (E)-1,4-dichloro-2-butene, NaH, DMF
b) 0.1M HCl

Example 22

Preparation of (E)-5-Amino-3-(4-chloro-2-buten-1-yl)-3H-thiazolo[4,5-d]pyrimidin-2-one (62)

Step 1: Preparation of (E)-5-Amino-3-(4-chloro-2-buten-1-yl)-3H-thiazolo[4,5-d]pyrimidin-2-one (61)

The title compound 61 can be synthesized by treating 5-Amino-3H-thiazolo[4,5-d]pyrimidin-2-one (1) in DMF with sodium hydride and (E)-1,4-dichloro-2-butene under various conditions.

Step 2: Preparation of (E)-5-Amino-3-(4-hydroxy-2-buten-1-yl)-3H-thiazolo[4,5-d]pyrimidin-2-one (62)

The title compound 62 could be synthesized by treating (E)-5-Amino-3-(4-chloro-2-buten-1-yl)-3H-thiazolo[4,5-d]pyrimidin-2-one (61) with 0.1 M HCl under various conditions.

Scheme 3

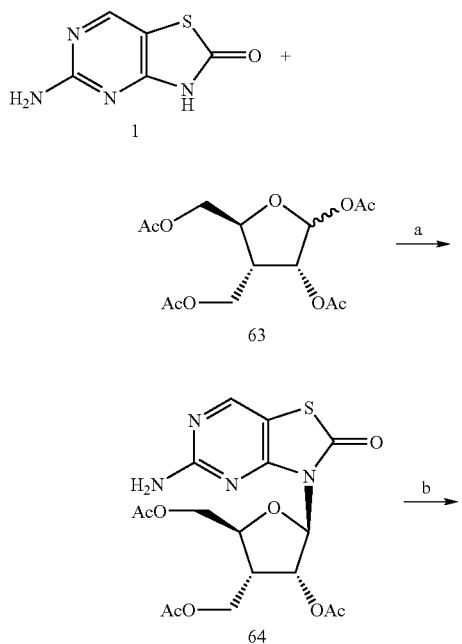

86

-continued

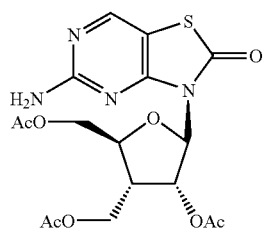

65 a) BSA, TMSOTf, CH₃CN, 80° C., 3-4 h
b) K₂CO₃, DMF, rt, overnight

Example 23

Preparation of (3'S)-5-Amino-3-(3'-deoxy-3'-hydroxymethyl-β-D-ribofuranosyl)-3H-thiazolo[4,5-d]pyrimidin-2-one (65)

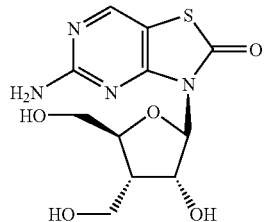

Step 1: Preparation of (3'S)-5-Amino-3-(3'-acetoxymethyl-2',5'-di-O-acetyl-3'-deoxy-β-D-ribofuranosyl)-3H-thiazolo[4,5-d]pyrimidin-2-one (64)

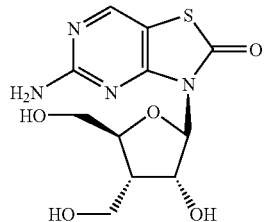

(3S)-3-O-Acetoxymethyl-1,2,5-tri-O-acetyl-3-deoxy-α,β-D-ribofuranose (63) [prepared according to the method of Cooperwood et al. *Nucleosides, Nucleotides, and Nucleic Acids* 2000, 19, 219-236 in which the enantiomer of the same compound was made] (176 mg, 0.53 mmol) was dissolved in acetonitrile (7 mL) at ambient temperature. 5-Amino-3H-thiazolo[4,5-d]pyrimidin-2-one (1) (89 mg, 0.53 mmol) was added, the mixture was then stirred for 0.5 h before it was heated to 40° C. After 5 min at 40° C., BSA (0.39 mL, 1.59 mmol) was added and the mixture was stirred for another 0.5 h. The mixture was then heated to 80° C. TMSOTf (0.14 mL, 0.80 mmol) was added and the reaction was stirred for 3-4 hours at 80° C. Upon completion, the reaction was allowed to cool to room temperature and then quenched by a pH 7.0 buffer (1.0 M K₂HPO₄ and 1.0 M NaH₂PO₄, 2 ml). The mixture was extracted with CH₂Cl₂ (3×10 mL). The combined organic layers were washed with brine, dried with Na₂SO₄, and concentrated in vacuo. The crude product was purified by column chromatography (SiO$_2$, 0-10% MeOH—CH$_2$Cl$_2$ to afford 77 mg (33%) of 64 as a powdery light yellow solid: $^1$H NMR (400 MHz, CDCl$_3$) δ 8.14 (s, 1H), 6.04 (d, J=1.6, 1H), 5.90 (dd, J=6.8, 1.6, 1H), 5.24 (s, 2H), 4.52 (dd, J=12.0, 2.8, 1H), 4.36 (m, 2H), 4.17 (m, 2H), 3.54 (m, 1H), 2.18 (s, 9H); [M+H]$^+$ 441.2; Elemental analysis for C$_{17}$H$_{20}$N$_4$O$_8$S.0.6H$_2$O: calc'd: C, 45.25; H, 4.74; N, 12.42; S, 7.11. found: C, 45.24; H, 4.66; N, 12.02; S, 7.24.

Step 2: Preparation of (3'S)-5-Amino-3-(3'-deoxy-3'-hydroxymethyl-β-D-ribofuranosyl)-3H-thiazolo[4,5-d]pyrimidin-2-one (65)

(3'S)-5-Amino-3-(3'-acetoxymethyl-2',5'-di-O-acetyl-3'-deoxy-β-D-ribofuranosyl)-3H-thiazolo[4,5-d]pyrimidin-2-one 64 (114 mg, 0.28 mmol) was dissolved in methanol (2 mL) at ambient temperature. Potassium carbonate (2 mg, cat.) was added and the mixture was stirred at room temperature overnight. Upon completion, acetic acid was added (2 μL) and the mixture was stirred another 30 minutes at room temperature. The mixture was concentrated, purified by HPLC, then triturated by EtOAc to afford 79 mg (90%) of 65 as a white solid: $^1$H NMR (400 MHz, D$_2$O) δ 8.28 (s, 1H), 6.10 (m, 1H), 5.18 (m, 1H), 4.20 (m, 1H), 3.95 (m, 2H), 3.78 (m, 2H), 3.00 (m, 1H); [M+H]$^+$ 315.2; Elemental analysis for C$_{11}$H$_{14}$N$_4$O$_5$S.0.3H$_2$O.0.15iPrOH: calc'd: C, 41.83; H, 4.84; N, 17.04; S, 9.75. found: C, 41.92; H, 4.61; N, 16.89; S, 9.78.

Example 24

Preparation of 5-Amino-3-(5'-deoxy-5'-hydroxymethyl-β-D-ribofuranosyl)-3H-thiazolo[4,5-d]pyrimidin-2-one (68)

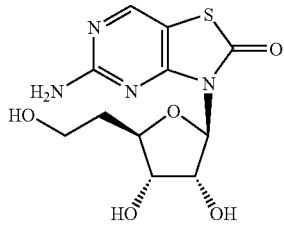

68

Step 1: Preparation of 5-Amino-3-(5'-O-acetoxymethyl-2',3'-di-O-acetyl-5'-deoxy-β-D-ribofuranosyl)-3H-thiazolo[4,5-d]pyrimidin-2-one (67)

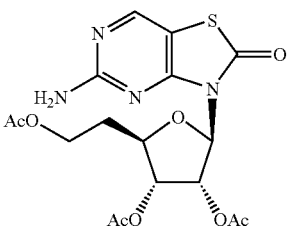

67

In a manner similar to Example 23, Step 1, 113 mg of the title compound 67 was generated from 5-O-acetoxymethyl-1,2,3-tri-O-acetyl-5-deoxy-α,β-D-ribofuranose (66) [prepared according to the method of Pakulski et al. *Polish J. Chem.* 1995, 69, 912-917] in 53% yield as a sticky yellow solid: $^1$H NMR (400 MHz, CDCl$_3$) δ 8.15 (s, 1H), 6.34 (m, 1H), 6.25 (d, J=6.0, 1H), 6.11 (d, J=4.0, 1H), 6.04 (m, 1H), 5.76 (t, J=6.0, 1H), 5.42 (s, 1H), 4.93 (m, 1H), 4.35 (m, 1H), 4.21 (q, J=5.6, 1H), 2.20 (s, 9H); [M+H]$^+$ 441.2.

Step 2: Preparation of 5-Amino-3-(5'-deoxy-5'-hydroxymethyl-β-D-ribofuranosyl)-3H-thiazolo[4,5-d]pyrimidin-2-one (68)

In a manner similar to Example 23, Step 2, 43 mg of the title compound 68 was generated in 71% yield as a white solid: $^1$H NMR (400 MHz, d$_6$-DMSO) δ 8.33 (s, 1H), 6.84 (s, 2H), 5.86 (d, J=4.4, 1H), 5.26 (d, J=5.2, 1H), 4.93 (m, 1H), 4.74 (q, J=10.0, 4.4, 2H), 4.40 (m, 1H), 3.82 (m, 2H), 1.76 (m, 3H); [M+H]$^+$ 315.2; Elemental Analysis for C$_{11}$H$_{14}$N$_4$O$_5$S.0.4H$_2$O.0.2iPrOH: calc'd: C, 41.77; H, 4.96; N, 16.80; S, 9.61. found: C, 41.61; H, 4.85; N, 16.68; S, 9.58.

Example 25

Preparation of 5-Amino-3-(3'-deoxy-3'-O-p-toluenesulfonyl-β-D-xylofuranosyl)-3H-thiazolo-[4,5-d]pyrimidine-2-one (73)

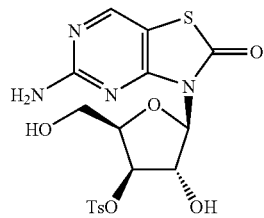

73

Scheme 4

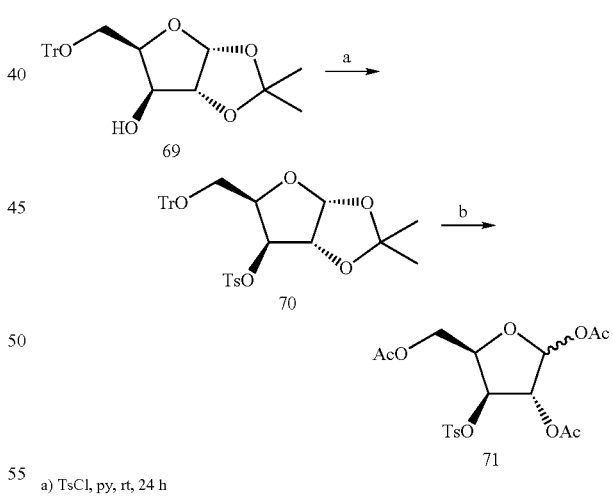

a) TsCl, py, rt, 24 h
b) Ac$_2$O, AcOH, H$_2$SO$_4$, rt, 24 h

Step 1: Preparation of 1,2-O-Isopropyliene-3-O-p-toluenesulfonyl-5-O-trityl-β-D-xylofuranose (70)

1,2-O-Isopropylidene-5-O-trityl-β-D-xylofuranose (69) [prepared according to the method of Johnston et al. *Tetrahedron Lett.* 1995, 36, 4341-4344] (4.25 g, 9.83 mmol) was dissolved in pyridine (60 mL) at ambient temperature. P-Toluenesulfonyl chloride (2.81 g, 14.74 mmol) was added to the solution. After 24 h the reaction had gone to completion, the crude mixture was concentrated. The residue was dissolved in EtOAc (50 mL), washed with saturated aqueous NH$_4$Cl (25 mL), saturated aqueous NaHCO$_3$ (25 mL) and brine (25 mL). The organic phase was dried over MgSO$_4$, filtered, then concentrated. The mixture was then purified by ISCO chromatography (SiO$_2$, 2-15% EtOAc-Hexane), affording 5.20 g (90%) of 70 as a white solid: $^1$H (400 MHz, CDCl$_3$) δ 7.61 (m, 2H), 7.32-7.34 (m, 6H), 7.23-7.32 (m, 9H), 5.92 (d, J=4.4, 1H), 4.74 (dd, J=11.2, 3.6, 2H), 4.19-4.22 (m, 1H), 3.45 (dd, J=10.4, 6.4, 1H), 3.05 (q, J=5.2, 1H), 2.40 (s, 3H), 1.49 (s, 3H), 1.31 (s, 3H).

Step 2: Preparation of 1,2,5-Tri-O-acetyl-3-O-p-toluenesulfonyl-α,β-D-xylofuranose (71)

1,2-O-isopropyliene-3-O-p-toluenesulfonyl-5-O-trityl-β-D-xylofuranose (70) (5.20 g, 8.86 mmol) was dissolved in AcOH (60 mL) at ambient temperature. Acetic anhydride (4.23 mL, 44.71 mmol) was added dropwise to the solution. The resulting mixture was cooled to 0° C., followed by slow addition of 1M H$_2$SO$_4$ (9.75 mL, 9.75 mmol). After 24 h the reaction had gone to completion, the crude mixture was concentrated, then azeotroped with toluene (2×20 mL). The residue was dissolved in CH$_2$Cl$_2$ (50 mL), washed with saturated aqueous NaHCO$_3$ (20 mL). The Organic phase was dried over MgSO$_4$, filtered, then concentrated. The mixture was then purified by ISCO chromatography (SiO$_2$, 2-40% EtOAc-Hexane), affording 3.09 g (81%) of 71 as a colorless oil: $^1$H (400 MHz, CDCl$_3$) δ (a mixture of α and β isomers) 7.80-7.85 (m), 7.37-7.39 (m), 6.36 (d, J=4.4), 6.06 (s), 5.20-5.30 (m), 4.56-4.62 (m), 4.26-4.29 (m), 2.50 (s), 2.06-2.08 (m).

Step 3: Preparation of 5-Amino-3-[2',5'-di-O-acetyl-3'-deoxy-3'-O-p-toluenesulfonyl-β-D-xylofuranosyl]-3H-thiazolo-[4,5-d]pyrimidine-2-one (72)

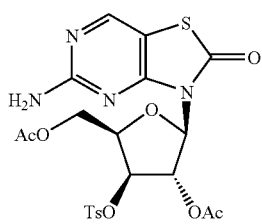

72

In a manner similar to Example 23, Step 1, 161 mg of the title compound 72 was generated in 54% yield as a fluffy yellow solid: $^1$H NMR (400 MHz, CDCl$_3$) δ 8.12 (s, 1H), 7.85 (d, J=8.8, 2H), 7.39 (d, J=8.8, 2H), 6.18 (d, J=2.8, 1H), 5.90 (br s, 2H), 5.77 (d, J=4.4, 1H), 5.01 (dd, J=6.4, 5.2, 1H), 4.34 (m, 1H), 4.27 (m, 2H), 2.48 (s, 3H), 2.04 (s, 6H); [M+H]$^+$ 539.3.

Step 4: Preparation of 5-Amino-3-[3'-deoxy-3'-O-p-toluenesulfonyl-β-D-xylofuranosyl]-3H-thiazolo-[4,5-d]pyrimidine-2-one (73)

In a manner similar to Example 23, Step 2, 68 mg of the title compound 73 was generated in 61% yield as a white solid: $^1$H NMR (400 MHz, DMSO-d$_6$) δ 8.36 (s, 1H), 7.83 (d, J=8.0, 2H), 7.48 (d, J=8.0, 2H), 6.80 (s, 2H), 5.92 (d, J=6.0, 1H), 5.71 (d, J=6.4, 1H), 5.20 (m, 1H), 4.89 (q, J=5.6, 3.6, 1H), 4.73 (s, 2H), 4.10 (m, 2H), 2.43 (s, 3H); [M+H]$^+$ 455.2; Elemental analysis for (C$_{17}$H$_{18}$N$_4$O$_7$S$_2$.0.4H$_2$O): calc'd: C, 44.22; H, 4.10; N, 12.14; S, 13.89. found: C, 44.45; H, 4.15; N, 12.07; S, 13.71.

Example 26

Preparation of 5-Amino-3-(3'-deoxy-3'-methylidene-β-D-ribofuranosyl)-3H-thiazolo[4,5-d]pyrimidin-2-one (76)

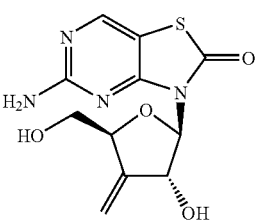

76

Step 1: Preparation of 5-Amino-3-(2'-O-acetyl-5'-O-benzoyl-3'-deoxy-3'-methylidene-β-D-ribofuranosyl)-3H-thiazolo[4,5-d]pyrimidin-2-one (75)

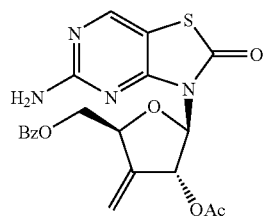

75

In a manner similar to Example 23, Step 1, 107 mg of the title compound 75 was generated from 1,2-di-O-acetyl-5-O-benzoyl-3-deoxy-3-methylidene-α,β-D-ribofuranose (74) [prepared according to the method of Girardet et al. *J. Med. Chem.* 2000, 43, 3704-3713] in 85% yield as a yellow solid: $^1$H NMR (400 NMHz, CDCl$_3$) δ 8.13 (s, 1H), 8.05 (dd, J=8.4, 1.2, 2H), 7.57 (tt, J=7.2, 1.2, 1H), 7.44 (t, J=7.2, 2H), 6.51 (m, 1H), 6.17 (d, J=4.4, 1H), 5.30 (s, 2H), 5.11 (m, 2H), 4.82 (dd, J=11.6, 4.8, 2H), 4.52 (dd, J=11.6, 6.8, 1H), 2.14 (s, 3H); [M+H]$^+$ 443.2.

Step 2: Preparation of 5-Amino-3-(3'-deoxy-3'-methylidene-β-D-ribofuranosyl)-3H-thiazolo[4,5-d]pyrimidin-2-one (76)

In a manner similar to Example 23, Step 2, 35 mg of the title compound 76 was generated in 35% yield as a gray-white solid: $^1$H NMR (400 MHz, DMSO-d$_6$) δ 8.37 (s, 1H), 5.83 (d, J=5.6, 1H), 5.74 (d, J=7.6, 1H), 5.51 (m, 2H), 5.19 (d, J=11.2, 2H), 4.72 (t, J=6.0, 1H), 4.54 (br s, 2H), 3.85 (s, 2H); [M+H]$^+$ 297.2; Elemental analysis for (C$_{11}$H$_{12}$N$_4$O$_4$S.0.2H$_2$O.0.25iPrOH): calc'd: C, 44.81; H, 4.61; N, 17.79; S, 10.18. found: C, 44.84; H, 4.33; N, 17.76; S, 10.22.

Example 27

Preparation of (3'R)-5-Amino-3-(3'-deoxy-3'-fluoro-β-D-xylofuranosyl)-3H-thiazolo[4,5-d]pyrimidin-2-one (79)

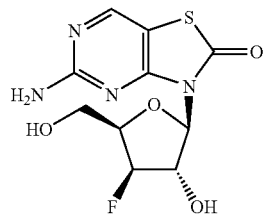

Step 1: Preparation of (3'R)-5-Amino-3-(2'-O-acetyl-5'-O-benzoyl-3'-deoxy-3'-fluoro-β-D-xylofuranosyl)-3H-thiazolo[4,5-d]pyrimidin-2-one (78)

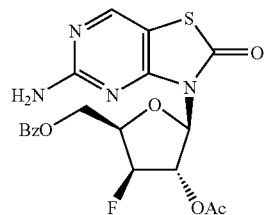

In a manner similar to Example 23, Step 1, 148 mg of the title compound 78 was generated from 1,2-Di-O-acetyl-5-O-benzoyl-3-deoxy-3-(R)-fluoro-α,β-D-xylofuranose (77) [prepared according to the method of Gosselin et al. *Carbohydrate Research* 1993, 249, 1-17] in 56% yield as a light yellow solid: $^1$H NMR (400 MHz, DMSO-d$_6$) δ 8.16 (s, 1H), 8.05 (d, J=8.8, 2H), 7.57 (t, J=7.6, 1H), 7.44 (t, J=8.0, 2H), 6.29 (ddd, J=21.2, 4.8, 1.2, 1H), 5.98 (d, J=4.8, 1H), 5.32 (ddd, J=52.0, 4.0, 1.2, 1H), 5.20 (s, 1H), 4.83 (dd, J=11.2, 4.8, 1H), 4.61 (m, 1H), 2.00 (s, 3H); [M+H]$^+$ 449.3.

Step 2: (3'R)-5-amino-3-(3'-deoxy-3'-fluoro-β-D-xylofuranosyl)-3H-thiazolo[4,5-d]pyrimidin-2-one (79)

In a manner similar to Example 23, Step 2, 43 mg of the title compound 79 was generated in 56% yield as yellow solid: $^1$H NMR (400 MHz, DMSO-d$_6$) δ 8.36 (s, 1H), 6.87 (s, 2H), 5.97 (d, J=4.8, 1H), 5.73 (d, J=5.6, 1H), 5.22 (dtd, J=24.4, 5.6, 2.0, 1H), 5.02 (ddd, J=52.8, 4.4, 1.6, 1H), 4.07 (m, 2H), 3.62 (m, 2H); [M+H]$^+$ 303.6.

Example 28

Preparation of (3'S)-5-amino-3-(2',5'-di-O-acetyl-3'-azido-3'-deoxy-β-D-ribofuranosyl)-3H-thiazolo[4,5-d]pyrimidin-2-one (83)

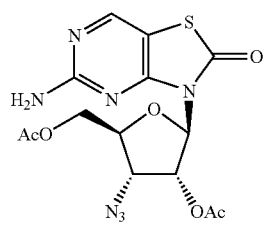

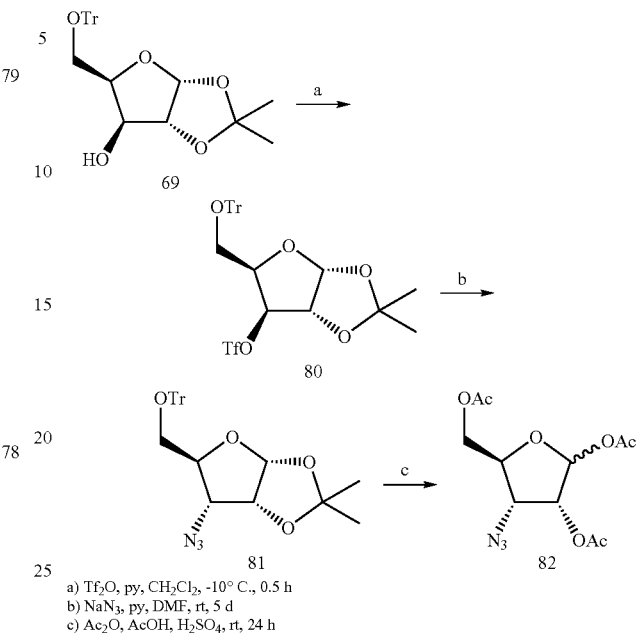

Scheme 5 a) Tf$_2$O, py, CH$_2$Cl$_2$, -10° C., 0.5 h
b) NaN$_3$, py, DMF, rt, 5 d
c) Ac$_2$O, AcOH, H$_2$SO$_4$, rt, 24 h

Step 1: Preparation of (3R)-3-Azido-3-deoxy-1,2-O-isopropyliene-5-O-trityl-β-D-ribofuranose (81)

1,2-O-Isopropylidene-5-O-trityl-β-D-xylofuranose (69) [prepared according to the method of Johnston et al. *Tetrahedron Lett.* 1995, 36, 4341-4344] (3.28 g, 7.58 mmol) was dissolved in CH$_2$Cl$_2$ (75 mL) at ambient temperature before it was cooled to -10° C. Pyridine (0.86 mL, 10.61 mmol) was added to the solution, followed by slow addition of trifluoromethanesulfonic anhydride (1.53 mL, 9.10 mmol). After stirring at -10° C. for 1 h the reaction was quenched by slow addition of 5% NaHSO$_3$ (150 mL) before it was warmed up to room temperature. The layers were then separated, and the aqueous phase was further extracted with CH$_2$Cl$_2$ (2×75 mL). The organic layers were combined, dried with MgSO$_4$, then filtered and concentrated. The residue was azeotroped with toluene (2×10 mL), then dried on high vacuum to afford triflate 80.

Triflate 80 was dissolved in DMF (100 mL) at ambient temperature. Pyridine (0.92 mL, 11.37 mmol) was added to the solution, followed by addition of sodium azide (1.97 g, 30.32 mmol). After 5 d the reaction had gone to completion, the crude mixture was concentrated. The residue was dissolved in EtOAc (60 mL), washed with saturated aqueous NH$_4$Cl (40 mL). The organic layer was dried over MgSO$_4$, filtered and concentrated. The mixture was then purified by ISCO chromatography (SiO$_2$, 2-15% EtOAc-Hexane), affording 1.80 g (52% for 2 steps) of 81 as a white solid: $^1$H (400 MHz, CDCl$_3$) δ 7.44-7.47 (m, 6H), 7.26-7.32 (m, 6H), 7.24-7.25 (m, 3H), 5.90 (d, J=3.6, 1H), 4.77 (t, J=4.4, 1H), 4.18-4.22 (m, 1H), 3.66 (q, J=6.0, 1H), 3.52 (dd, J=10.4, 3.2, 1H), 3.20 (dd, J=10.8, 4.0, 1H), 1.59 (s, 3H), 1.40 (s, 3H).

Step 2: Preparation of (3R)-1,2,5-Tri-O-acetyl-3-azido-3-deoxy-α,βD-ribofuranose (82)

(3R)-3-Azido-3-deoxy-1,2-O-isopropyliene-5-O-trityl-β-D-ribofuranose (81) (1.20 g, 2.62 mmol) was dissolved in AcOH (30 mL) at ambient temperature. Acetic anhydride (1.24 mL, 13.10 mmol) was added dropwise to the solution. The resulting mixture was cooled to 0° C., followed by slow addition of 1M $H_2SO_4$ (2.88 mL, 2.88 mmol). After 24 h the reaction had gone to completion, the crude mixture was concentrated, then azeotroped with toluene (2×10 mL). The residue was dissolved in $CH_2Cl_2$ (30 mL), washed with saturated aqueous $NaHCO_3$ (20 mL). The Organic phase was dried over $MgSO_4$, filtered, and concentrated. The mixture was then purified by ISCO chromatography ($SiO_2$, 2-40% EtOAc-Hexane), affording 0.66 g (83%) of 82 as a colorless oil: $^1H$ (400 MHz, $CDCl_3$) δ (a mixture of α and β isomers) 6.43 (d, J=4.4), 6.14 (s), 5.34 (d, J=4.8), 5.21 (dd, J=7.6), 4.20-4.37 (m), 4.04-4.10 (m), 2.10-2.20 (m).

Step 3: Preparation of (3'R)-5-amino-3-(2',5'-di-O-acetyl-3'-azido-3'-deoxy-β-D-ribofuranosyl)-3H-thiazolo[4,5-d]pyrimidin-2-one (83)

In a manner similar to Example 23, Step 1, 288 mg of the title compound 83 was generated in 85% yield as a orange solid: $^1H$ NMR (400 MHz, $CDCl_3$) δ 8.17 (s, 1H), 6.18 (d, J=2.4, 1H), 5.95 (dd, J=6.4, 2.8, 1H), 5.14 (s, 2H), 4.61 (m, 1H), 4.24 (dd, J=12.0, 5.2, 1H), 4.17 (m, 2H), 2.12 (s, 6H); $[M+H]^+$ 410.4.

Scheme 6

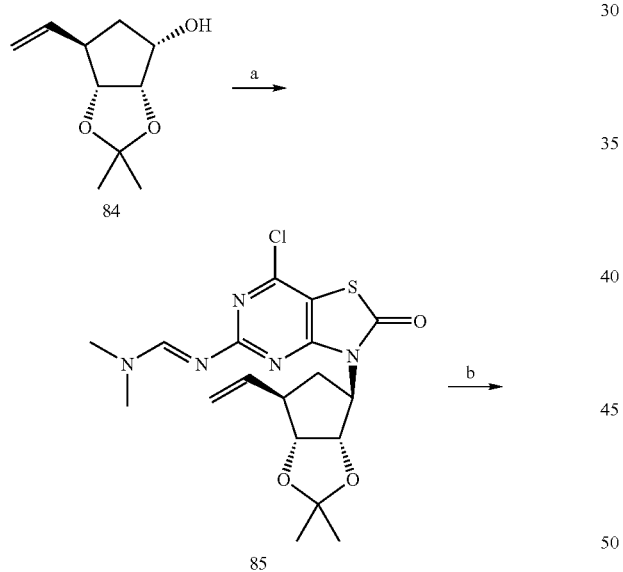

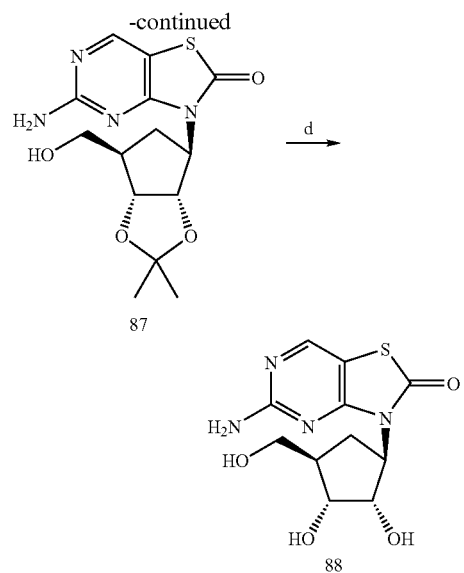

a) $Tf_2O$, py, $CH_2Cl_2$, 0° C., 0.5 h; Chloroamidine base, NaH, $CH_3CN$, rt, 50° C., 12 h
b) $NaIO_4$, $OsO_4$, $CH_3OH/H_2O$; $NaBH_4$, $CH_3OH$
c) Zn—Cu, AcOH
d) 2M HCl, $CH_3OH$ Example 29

Preparation of (1'R,2'S,3'R,4'R)—N'-[7-chloro-2-oxo-3-(2',3'-O-isopropylidene-4'-vinyl-cyclopentan-1'-yl)-2,3-dihydro-thiozolo[4,5-d]pyrimidin-5-yl]-N,N-dimethyl-formamidine (88)

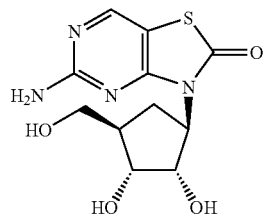

88

Step 1: Preparation of (1'R,2'S,3'R,4'R)—N'-[7-chloro-2-oxo-3-(2',3'-O-isopropylidene-4'-vinyl-cyclopentan-1-yl)-2,3-dihydro-thiozolo[4,5-d]pyrimidin-5-yl]-N,N-dimethyl-formamidine (85)

(1R,2S,3R,4R)-2,3-O-isopropylidene-4-vinyl-cyclopentan-1-ol (84) [prepared according to the method of Yang et al. *J. Org. Chem.* 2004, 69, 3993-3996] (96 mg, 0.52 mmol) was dissolved in $CH_2Cl_2$ (2 mL) and pyridine (10 mL) at ambient temperature. The solution was cooled to 0° C., followed by slow addition of trifluoromethanesulfonic anhydride (115 μL, 0.68 mmol). After 0.5 h, the reaction had gone to completion, the reaction was quenched with $H_2O$ (10 mL), then further diluted with $CH_2Cl_2$ (10 mL). After the layers were separated, the aqueous phase was further washed with $CH_2Cl_2$ (2×10 mL). The Organic fractions were combined, dried over $MgSO_4$, filtered, then concentrated. The resulting yellowish oil was used for next step directly.

The above triflate (131 mg, 0.51 mmol) was suspended in $CH_3CN$ (10 mL) at ambient temperature. Sodium hydride (15 mg, 0.62 mmol) was added to the solution, followed by the addition of a solution of N'-[7-chloro-2-oxo-2,3-dihydro-thiozolo[4,5-d]pyrimidin-5-yl)-N,N-dimethyl-formamidine (Chloroamidine base, 160 mg, 0.62 mmol) in $CH_3CN$ (8 mL). The reaction was stirred at 50° C. for 12 h before it was quenched by addition of $H_2O$ (5 mL). The resulting mixture was extracted with EtOAc (3×20 mL). The organic fractions were combined, dried over $MgSO_4$, filtered, then concentrated. The mixture was then purified by column chromatography ($SiO_2$, 2-20% EtOAc-Hexane), affording 94.8 mg (43%) of 85 as a white solid: $^1H$ (400 MHz, $CDCl_3$) δ 8.63 (s, 1H), 5.92 (m, 1H), 5.09-5.29 (m, 4H), 4.55-4.61 (m, 1H), 3.23 (s, 3H), 3.21 (s, 3H), 2.65-2.77 (m, 1H), 2.42-2.51 (m, 1H), 2.18-2.22 (m, 1H), 1.56 (s, 3H), 1.29 (s, 3H); $[M+H]^+$ 424.1.

Step 2: Preparation of (1'R,2'S,3'R,4'R)-5-Amino-7-chloro-3-(2',3'-O-isopropylidene-4'-hydroxymethyl-cyclopentan-1'-yl)-3H-thiazolo[4,5-d]pyrimidin-2-one (86)

The title compound 86 can be synthesized by first treating (1'R,2'S,3'R,4'R)—N'-[7-chloro-2-oxo-3-(2',3'-O-isopropylidene-4'-vinyl-cyclopentan-1'-yl)-2,3-dihydro-thiozolo[4,5-d]pyrimidin-5-yl]-N,N-dimethyl-formamidine (85) in $CH_3OH$ and $H_2O$ with sodium periodate and Osmium tetroxide. The crude product can then be treated with sodium borohydride in $CH_3OH$ to afford 86.

Step 3: Preparation of (1'R,2'S,3'R,4'R)-5-Amino-3-(2',3'-O-isopropylidene-4'-hydroxymethyl-cyclopentan-1'-yl)-3H-thiazolo[4,5-d]pyrimidin-2-one (87)

The title compound 87 can be synthesized by treating (1'R, 2'S,3'R,4'R)-5-Amino-7-chloro-3-(2',3'-O-isopropylidene-4'-hydroxymethyl-cyclopentan-1'-yl)-3H-thiazolo[4,5-d]pyrimidin-2-one (86) in AcOH with Zinc copper couple under various conditions.

Step 4: Preparation of (1'R,2'S,3'R,4'R)-5-Amino-3-(2',3'-dioxy-4'-hydroxymethyl-cyclopentan-1'-yl)-3H-thiazolo[4,5-d]pyrimidin-2-one (88)

The title compound 88 can be synthesized by treating (1'R, 2'S,3'R,4'R)-5-Amino-3-(2',3'-O-isopropylidene-4'-hydroxymethyl-cyclopentan-1'-yl)-3H-thiazolo[4,5-d]pyrimidin-2-one (87) in $CH_3OH$ with 2M HCl under various conditions.

Example 30

Preparation of 5-Amino-3-(3'-(R)-methoxy-β-D-xylofuranosyl)-3H-thiazolo[4,5-d]pyrimidin-2-one (89)

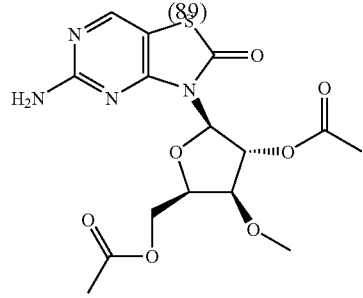

The required sugar, acetic acid 1,2,5-tri-O-acetyl-3)-methoxy-D-xylofuranose α and β mixture (91) was prepared as follows:

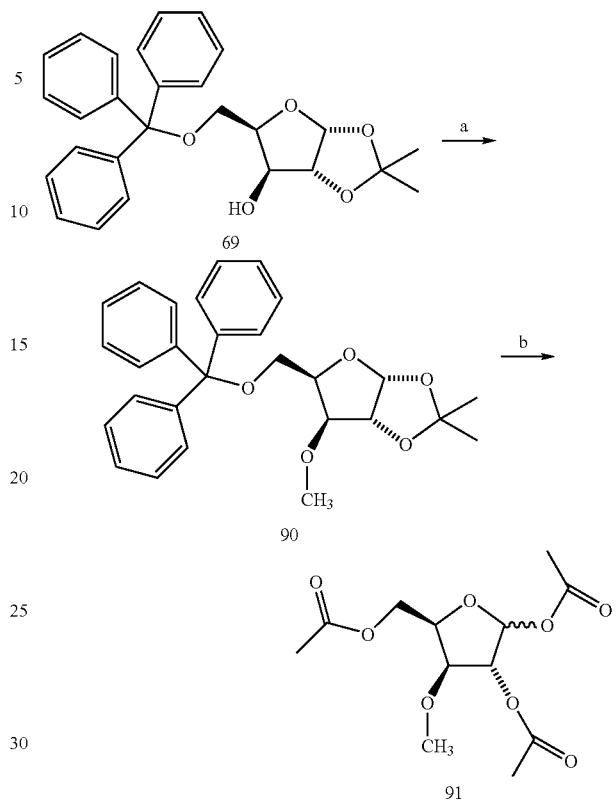

a. NaH, THF, $CH_3I$  b. $H_2SO_4$, AcOH — $Ac_2O$

Step 1: Preparation of 1,2-O-isopropylidene-3-methoxy-5-O-trityl-D-xylofuranose (90)

Trityl alcohol 69 (5 g, 11.57 mmol) was mixed with methyl iodide (2.5 ml, 34.7 mmol) in THF (40 ml). Tetrabutylammonium iodide (427 mg) was added and the mixture cooled in an ice bath. Under a slow stream of nitrogen solid sodium hydride-oil mixture (1.33 g, 60% NaH, 34.7 mmol) was added in small portions. The reaction was stirred overnight while warming slowly to ambient temperature. The reaction was carefully poured into a mixture of saturated ammonium chloride and ice and extracted three times with ethyl ether. The ether portions were combined, washed with brine, dried ($MgSO_4$), filtered and the solvent evaporated to yield 90 as a cloudy oil. $^1H$ NMR (400 MHz, $CDCl_3$) δ 7.42 7.42 (m, 6H), 7.26 (m, 9H), 5.85 (d, J=3.6 Hz, 1H), 4.54 (d, J=3.6 Hz, 1H), 4.38 (m, 1H), 3.785 (d, J=3.2 Hz, 1H), 3.42 (m, 1H), 3.35 (m, 4H), 1.53 (s, 3H), 1.336 (s, 3H)

Step 2: 1,2,5-tri-O-acetyl-3-methoxy-D-xylofuranose α and β Mixture (91)

The trityl compound 90 (6.1 g, 11.57 mmol) was dissolved in a mixture of acetic acid (20 ml) and acetic anhydride (10 ml) and cooled in a cool water bath. A mixture of sulfuric acid in acetic anhydride and acetic acid was added (0.5 ml sulfuric acid, 2.5 ml acetic acid, 2.5 ml acetic anhydride, pre-cooled in an ice bath before addition) and the mixture stirred at ambient temperature over night. The reaction was poured onto 400 g of ice water and extracted three times with ethyl acetate. The organic portions were combined, washed with saturated sodium bicarbonate, dried (MgSO$_4$), filtered and evaporated to yield a semisolid. This was purified using flash chromatography on a 120 g silica gel column eluting with a gradient of ethyl acetate in hexane (10-100%) to give 91 (1.26 g, 4.34 mmol, 38%) as an oily mixture of anomers. $^1$H NMR (400 MHz, CDCl$_3$) δ 6.39 (d, J=4.4 Hz), 6.17 (s), 4.4-4.52 (m), 4.3-4.39 (m), 4.1-4.24 (m), 3.86 (d, J=5.6 Hz), 3.45 (s), 3.41 (s), 2.07-2.16 (m).

Step 3: Preparation of 5-Amino-3-(3'-methoxy-β-D-xylofuranosyl)-3H-thiazolo[4,5-d]pyrimidin-2-one (89)

In a manner similar to Example 23, step 1, using 1,2,5-tri-O-acetyl-3-methoxy-D-xylofuranose α and β mixture (91), afforded 43 mg (6%) of 89 as a white solid: $^1$H NMR (DMSO-d$_6$) δ 2.01 (d, J=9.2 Hz, 6H), 3.36 (s, 3H), 4.17-4.24 (m, 2H), 4.31-4.37 (m, 2H), 5.86 (d, J=6 Hz, 1H), 6.14 (dd, J=4.4, 1.6 Hz, 1H), 6.85 (br s, 2H), 8.35 (s, 1H); MS (ESI) [(M+H)$^+$] 399.96, Elemental analysis for (C$_{15}$H$_{18}$N$_4$O$_7$S.0.5H$_2$O): calc'd: C, 44.22; H, 4.70; N, 13.75. Found C, 44.27; H, 4.54; N, 13.60.

Example 31

Preparation of 5-Amino-3-(3'-octyloxy-β-D-xylofuranosyl)-3H-thiazolo[4,5-d]pyrimidin-2-one (92)

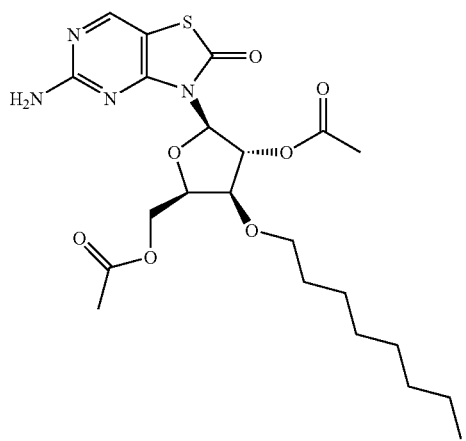

The required sugar acetic acid 1,2,5-tri-O-acetyl-3(S)-octyloxy-D-xylofuranose α and β mixture (94) was prepared as follows:

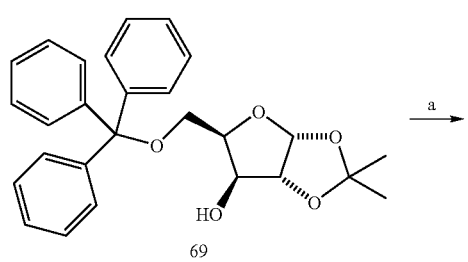

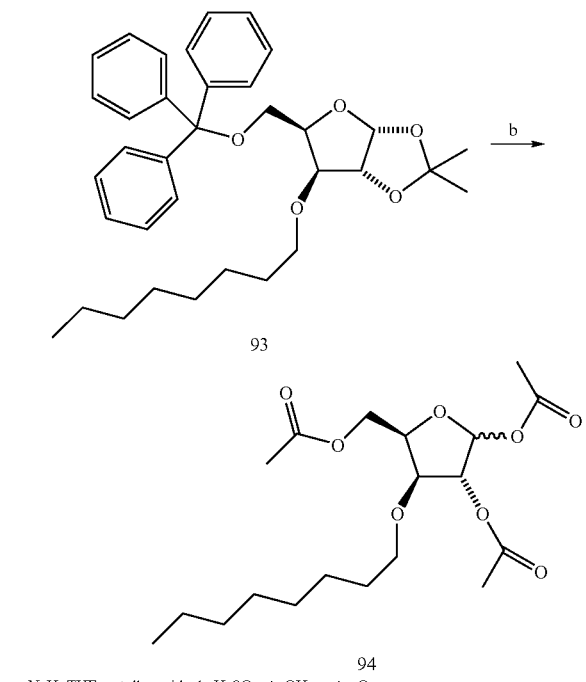

a. NaH, THF, octylbromide  b. H$_2$SO$_4$, AcOH—Ac$_2$O

Step 1: Preparation of 1,2-O-isopropylidene-3-octyloxy-5-O-trityl-D-xylofuranose (5)

Trityl alcohol 69 (5 g, 11.57 mmol) was mixed with octylbromide (3.99 ml, 23.14 mmol) in THF (40 ml). Tetrabutylammonium iodide (427 mg) was added and the mixture cooled in an ice bath. Under a slow stream of nitrogen solid sodium hydride-oil mixture (1.33 g, 60% NaH, 34.7 mmol) was added in small portions. The reaction mixture was stirred overnight while warming slowly to ambient temperature. The reaction was carefully poured into a mixture of saturated ammonium chloride and ice and extracted three times with ethyl ether. The ether portions were combined, washed with brine, dried (MgSO$_4$), filtered and the solvent evaporated to yield a cloudy oil. The oil was purified by flash chromatography on a 120-gram silica gel column using a gradient of ethyl acetate in hexane (1-30%) to give 93 as a clear oil (2.37 g, 4.72 mmol, 41%). $^1$H NMR (400 MHz, CDCl$_3$) δ 7.42 7.42 (m, 6H), 7.26 (m, 9H), 5.85 (d, J=3.6 Hz, 1H), 4.50 (d, J=3.6 Hz, 1H), 4.343 (m, 1H), 3.86 (d, J=3.6 Hz, 1H), 3.45 (m, 2H), 3.32 (m, 2H), 1.54 (m, 3H), 1.41 (m 2H), 1.33 (s, 3H), 1.22 (m, 10H), 0.889 (t, J=6.8 Hz, 3H)

Step 2: Acetic Acid 1,2,5-tri-O-acetyl-3-octyloxy-D-xylofuranose α and β Mixture (94)

The trityl compound 93 (4.12 g, 7.57 mmol) was dissolved in a mixture of acetic acid (35 ml) and acetic anhydride (15 ml) and cooled in a cool water bath. A mixture of sulfuric acid in acetic anhydride and acetic acid was added (0.5 ml sulfuric acid, 2 ml acetic acid, 2 ml acetic anhydride, pre-cooled in an ice bath before addition) and the mixture stirred at ambient temperature over night. The reaction was poured onto 400 g of ice water and extracted three times with ethyl acetate. The organic portions were combined, washed with saturated sodium bicarbonate, dried (MgSO$_4$), filtered and evaporated to yield a semisolid. This was purified using flash chromatography on a 120 g silica gel column eluting with a gradient of ethyl acetate in hexane (5-60%) to give 94 (1.12 grams, 2.88 mmol, 38%) as an oily mixture of anomers. $^1$H NMR (400 MHz, CDCl$_3$) δ 6.39 (d, J=3.6 Hz), 6.1 (s), 5.19 (m) 4.46-4.52 (m), 4.31-4.43 (m), 4.11-4.25 (m), 3.93 (m), 3.45-3.68 (m), 3.4-3.46 (m), 2.07-2.1 (m), 1.540 (m), 1.27 (m), 0.882 (t, J=6.8 Hz)

Step 3: Preparation of 5-Amino-3-(3'-octyloxy-β-D-xylofuranosyl)-3H-thiazolo[4,5-d]pyrimidin-2-one (92)

In a manner similar to Example 23, step 1, using Acetic acid 1,2,5-tri-O-acetyl-3-octyloxy-D-xylofuranose α and β mixture (94), afforded 80 mg (11%) of 92 as a fluffy white solid: $^1$H NMR (400 MHz DMSO-d$_6$) δ 0.84-0.88 (m, 3H), 1.23-1.30 (m, 10H), 1.49-1.52 (m, 2H), 2.00 (s, 3H), 2.02 (s, 3H), 3.41-3.44 (m, 1H), 3.57-3.59 (m, 1H), 4.16-4.21 (m, 1H), 4.30-4.37 (m, 3H), 5.87 (d, J=5.6, 1H), 6.12 (dd, J=4.4, 1.2 Hz, 1H), 6.85 (br s, 2H), 8.35 (s, 1H); MS (ESI) [(M+H)$^+$] found 497.40. Elemental analysis for (C$_{22}$H$_{32}$N$_4$O$_7$S): C, 53.21; H, 6.50; N, 11.28. Found C, 53.52; H, 6.49; N, 11.21.

Example 32

Preparation of 5-Amino-3-(3'-(R)-(2-methoxy-ethoxy), 2',5'-di-O-acetyl-β-D-xylofuranosyl)-3H-thiazolo[4,5-d]pyrimidin-2-one (95)

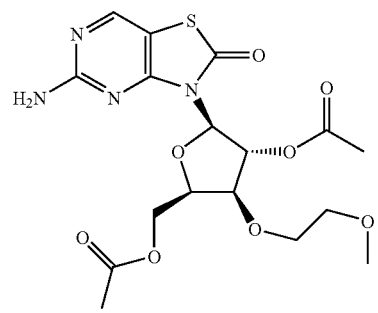

The required sugar, acetic acid 1,2,5-tri-O-acetyl-3-(2-methoxy-ethoxy)-D-xylofuranose α and β mixture (98) as follows:

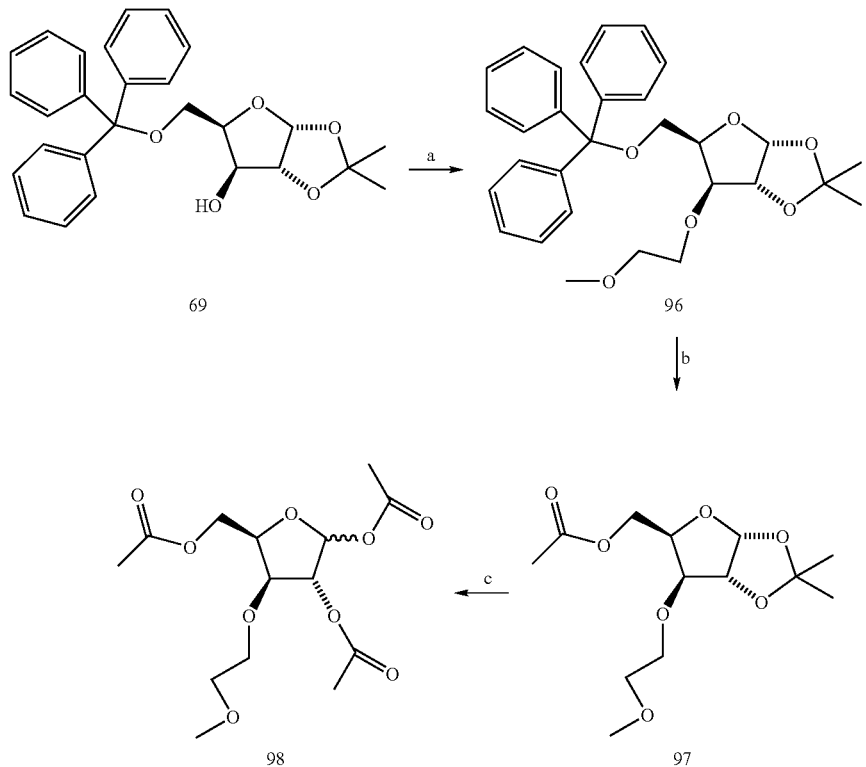

a. NaH, THF, 2-bromoethylmethyl ether   b. Acetylbromide, Ac2O,   c. H$_2$SO$_4$, AcOH — Ac$_2$O

Step 1: 1,2-O-isopropylidene-3-(2-methoxy-ethoxy)-5-O-trityl-D-xylofuranose (96)

Trityl alcohol 69 (5 grams, 11.57 mmol) was mixed with 2-bromoethylmethyl ether (2.17 ml, 23.14 mmol) in THF (40 ml). Tetrabutylammonium iodide (427 mg) was added and the mixture cooled in an ice bath. Under a slow stream of nitrogen solid sodium hydride-oil mixture (1.33 g, 60% NaH, 34.7 mmol) was added in small portions. The reaction was stirred overnight while warming slowly to ambient temperature. The reaction was carefully poured into a mixture of saturated ammonium chloride and ice and extracted three times with ethyl ether. The ether portions were combined, washed with brine, dried (MgSO$_4$), filtered and the solvent evaporated to yield a cloudy oil. The oil was purified by flash chromatography on a 120 g silica gel column using a gradient of ethyl acetate in hexane (3-30%). The ether product 96 was isolated as a thick oil (4.54 g, 9.26 mmol, 80%). $^1$H NMR (400 MHz, CDCl$_3$) δ 7.42 (m, 6H), 7.26 (m, 9H), 5.86 (d, J=3.6 Hz, 1H), 4.54 (d, J=4 Hz, 1H), 4.37 (m, 1H), 4.35 (m, 1H), 3.95 (d, J=2.8 Hz, 1H), 3.64-3.68 (m, 1H), 3.47-3.52 (m, 2H) 3.29-3.33 (m, 2H), 3.24 (s, 3H) 1.53 (s, 3H), 1.326 (s, 3H)

Step 2: 1,2-O-isopropylidene-3-(2-methoxy-ethoxy)-5-O-acetyl-D-xylofuranose (97)

The trityl ether 96 (5.5 g, 11.22 mmol) was dissolved in acetic anhydride (30 ml) and acetyl bromide (2.0 ml, 22.4 mmol) was added. After one hour the reaction was filtered and the filtrate evaporated to dryness. The residue was purified using flash chromatography on a 120 g silica gel column using a gradient of ethyl acetate in hexane (10-100%) to yield 1.54 g (5.31 mmol, 47%) of acetate 97. $^1$H NMR (400 MHz, CDCl$_3$) δ 5.925 (d, J=3.6 Hz, 1H), 4.58 (d, J=3.6 Hz, 1H), 4.38 (m, 2H), 4.23 (m, 1H), 3.92 (d, J=3.6 Hz, 1H), 3.72 (m, 1H), 3.60 (m, 1H), 3.50 (m, 2H), 3.35 (s, 3H), 2.08 (s, 3H), 1.49 (s, 3H), 1.32 (s, 3H).

Step 3: Acetic Acid 1,2,5-tri-O-acetyl-3-(2-methoxy-ethoxy)-D-xylofuranose α and β Mixture (98)

The acetate 97 (1.71 grams, 5.89 mmol) was dissolved in a mixture of acetic anhydride and acetic acid (1:4, 30 ml) and cooled in an ice bath. A solution of sulfuric acid in acetic acid (125 uL H$_2$SO$_4$ in 1.0 ml acetic anhydride) was added and the mixture maintained at −10 degrees overnight. The cold solution was poured onto 80 g of ice, let stand for 20 minutes and then extracted three times with ethyl acetate. The organic portions were combined, washed with brine, dried (MgSO$_4$), filtered and the solvent removed to get 1.94 g of crude product. The crude product was purified using flash chromatography on a 120 g silica gel column eluting with a gradient of ethyl acetate in hexane (10-75%) to yield 760 mg (2.27 mmol, 38%) of 98 as a mixture of anomers. $^1$H NMR (400 MHz, CDCl$_3$) δ 6.40 (d, J=4.4 Hz), 6.10 (s), 5.21 (m), 4.47-4.54 (m), 4.33-4.45 (m), 4.16-4.27 (m), 4.03 (m), 3.72-3.85 (m), 3.6-3.7 (m), 3.48-3.54 (m), 3.35-3.48 (m), 2.06-2.11 (m)

Step 4: Preparation of 5-Amino-3-(3'-(2-methoxy-ethoxy), 2',5'-di-O-acetyl-β-D-xylofuranosyl)-3H-thiazolo[4,5-d]pyrimidin-2-one (95)

In a manner similar to Example 23, step 1, using Acetic acid 1,2,5-tri-O-acetyl-3-(2-methoxy-ethoxy)-D-xylofuranose α and β mixture (98), afforded 220 mg (42%) of 95 as a fluffy white solid: $^1$H NMR (400 MHz DMSO-d$_6$) δ 2.04 (d, J=8.4 Hz, 6H), 3.29 (s, 3H), 3.49-3.52 (m, 2H), 3.58-3.63 (m, 1H), 3.76-3.81 (m, 1H), 4.19-4.24 (m, 1H), 4.36-4.43 (m, 3H), 5.88 (d, J=6 Hz, 1H), 6.18 (dd, J=3.6, 2 Hz, 1H), 6.87 (br s, 2H), 8.38 (s, 1H); MS (ESI) [(M+H)$^+$] found 443.31. Elemental analysis for (C$_{17}$H$_{22}$N$_4$O$_8$S.0.1H$_2$O.0.2EtOAc): C, 46.29; H, 5.19; N, 12.13. Found C, 46.09; H, 5.25; N, 11.72.

Example 33

Preparation of 5-Amino-3-(3'-Butoxy-α-D-xylofuranosyl)-3H-thiazolo[4,5-d]pyrimidin-2-one (99)

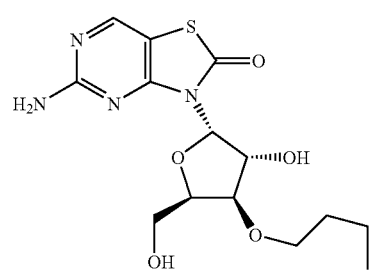

99

The required sugar acetic acid 1,2,5-tri-O-acetyl-3-butoxy-D-xylofuranose α and β mixture (101) was prepared as follows:

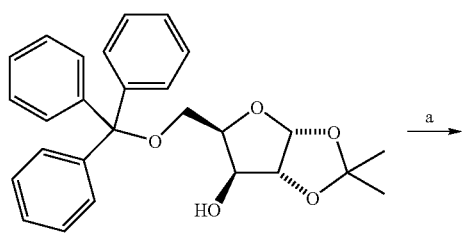

69

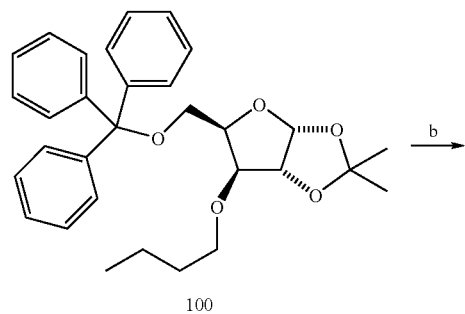

100

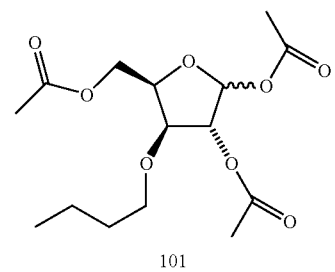

101 a. NaH, THF, nbutyliodide  b. H$_2$SO$_4$, AcOH — Ac$_2$O

Step 1: Preparation of 1,2-O-isopropylidene-3-butoxy-5-O-acetyl-D-xylofuranose (100)

Trityl alcohol 69 (5 grams, 11.57 mmol) was mixed with n-butyliodide (2.6 ml, 23.14 mmol) in THF (40 ml). Tetrabutylammonium iodide (427 mg) was added and the mixture cooled in an ice bath. Under a slow stream of nitrogen solid sodium hydride-oil mixture (1.33 g, 60% NaH, 34.7 mmol) was added in small portions. The reaction was stirred overnight while warming slowly to ambient temperature. The reaction was carefully poured into a mixture of saturated ammonium chloride and ice and extracted three times with ethyl ether. The ether portions were combined, washed with brine, dried (MgSO$_4$), filtered and the solvent evaporated to yield a cloudy oil. The oil was purified by flash chromatography on a 120 g silica gel column using a gradient of ethyl acetate in hexane (1-30%) to give 100 as a clear oil (2.32 g, 4.75 mmol, 41%). $^1$H NMR (400 MHz, CDCl$_3$) δ 7.42 (m, 6H), 7.26 (m, 9H), 5.86 (d, J=3.6 Hz, 1H), 4.51 (d, J=3.6 Hz, 1H), 4.35 (m, 1H), 3.86 (d, J=3.6 Hz, 1H), 3.46 (m, 2H), 3.29 (m, 2H), 1.54 (m, 3H), 1.38 (m, 2H), 1.33 (s, 3H), 1.23 (m, 2H), 0.83 (t, J=7.6 Hz, 3H)

Step 2: Preparation Acetic Acid 1,2,5-tri-O-acetyl-3-butoxy-D-xylofuranose α and β Mixture (101)

The trityl compound 100 (2.32 g, 4.75 mmol) was dissolved in 5% acetic anhydride in acetic acid (50 ml), cooled in a cool water bath and 0.02 ml of sulfuric acid was added and the mixture stirred overnight at ambient temperature. The reaction mixture was poured onto 150 grams of ice and extracted three times with methylene chloride. The organic portions were dried (MgSO$_4$), filtered and taken to dryness with toluene to give 3.19 g of a semi-solid. This was purified using flash chromatography on a 50 g silica gel column eluting with a gradient of ethyl acetate in hexane (5-75%) to give 101 (0.760 g, 2.29 mmol, 48%) as an oily mixture of anomers. $^1$H NMR (400 MHz, CDCl$_3$) δ 6.38 (d, J=3.6 Hz), 6.11 (s), 5.2 (m), 4.50 (m), 4.31-4.42 (m), 4.13-4.25 (m), 3.93 (d, J=3.6 Hz), 3.5-3.7 (m), 3.4-3.47 (m), 2.06-2.15 (m), 1.51-1.55 (m), 1.3-1.4 (m), 0.89-0.94 (m)

Step 3: Preparation of 5-Amino-3-(3')-Butoxy-2',5'-di-O-acetyl-α-D-xylofuranosyl)-3H-thiazolo[4,5-d]pyrimidin-2-one (102)

In a manner similar to Example 23, step 1, using Acetic acid 1,2,5-tri-O-acetyl-3-butoxy-D-xylofuranose α and β mixture (101), afforded 40 mg (8%) of 102 as a white solid. Taken crude on to step 2.

Step 2: Preparation of 5-Amino-3-(3'-Butoxy-α-D-xylofuranosyl)-3H-thiazolo[4,5-d]pyrimidin-2-one (99)

In a manner similar to Example 23, step 2, 102 afforded 5 mg (15%) of 99 as a white solid: $^1$H NMR (400 MHz, (CDCl$_3$) δ 0.84 (t, J=7.2 Hz, 3H), 1.27-1.32 (m, 2H), 1.51-1.54 (m, 2H), 3.20 (t, J=9.2 Hz, 1H), 3.35 (t, J=10.8 Hz, 1H), 3.72-3.84 (m, 3H), 3.97-4.01 (m, 1H), 4.74 (t, J=9.2 Hz, 1H), 5.17 (br s, 2H), 5.38 (d, J=9.2 Hz, 1H), 7.96 (s, 1H); MS (ESI) [(M+H)$^+$] found 356.80.

Example 34

Preparation of 5-Amino-3-(3'-methyl, 2',3',5'-tri-O-acetyl-β-D-xylofuranosyl)-3H-thiazolo[4,5-d]pyrimidin-2-one (103)

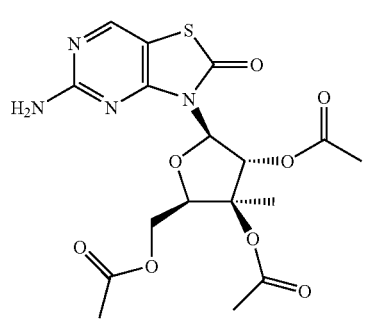

103

The preparation of the required sugar, 1,2,3,5 tetra-O-acetyl-3(S)-methyl D-xylofuranose α and β mixture (105), was prepared as follows:

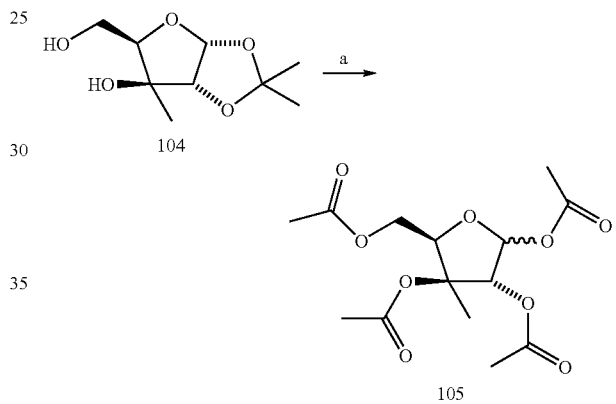

a. i. Ac$_2$O, pyridine, ii. H$_2$SO$_4$, Ac$_2$O — AcOH

Step 1: 1,2,3,5 tetra-O-acetyl-3-methyl D-xylofuranose α and β Mixture (105)

The diol 104 [prepared as described by Lu and Just; *Tetrahedron Letters* 41 (2000) 9223-9227] (1.69 g, 8.28 mmol), was dissolved in methylene chloride (25 ml) and pyridine (4.7 ml) was added. Acetic anhydride (3.9 ml, 41 mmol) was added along with DMAP (50 mg) and this mixture was stirred overnight at ambient temperature. The reaction was diluted with methylene chloride and washed with saturated ammonium chloride. The aqueous phase was extracted twice more with methylene chloride, the organic portions combined, dried (MgSO$_4$), filtered and evaporated to give a colorless oil. The oil was dissolved in 5% acetic anhydride in acetic acid (68 ml) and sulfuric acid (0.02 ml) was added and this was stirred overnight at ambient temperature. The reaction was poured onto 150 g of ice, extracted three times with methylene chloride, the organic phases combined, washed twice with saturated sodium bicarbonate, dried (MgSO$_4$), filtered and evaporated to get 2.84 g of an oil. The residue was purified using flash chromatography on a 120 g silica gel column using a gradient of ethyl acetate in hexane (5-75%) to yield 1.2 g (3.61 mmol, 44%) of 105 as a clear oil whose spectra are consistent with a mixture of anomers. $^1$H NMR (400 MHz, CDCl$_3$) δ 6.41 (d, J=4.8 Hz), 6.03 (d, J=1.2 Hz), 5.75 (d, J=0.8 Hz), 5.49 (d, J=5.2 Hz), 4.37-4.45 (m), 4.2-4.29 (m), 2.03-2.135 (m), 1.637 S), 1.624 (s)

Step 2: Preparation of 5-Amino-3-(3'-methyl, 2',3',5'-tri-O-acetyl-β-D-xylofuranosyl)-3H-thiazolo[4,5-d]pyrimidin-2-one (103)

In a manner similar to Example 23, step 1, using 1,2,3,5 tetra-O-acetyl-3-methyl D-xylofuranose α and β mixture (105), afforded 170 mg (28%) of 103 as a white solid: $^1$H NMR (400 MHz DMSO-d$_6$) δ 1.57 (s, 3H), 2.03 (s, 6H), 2.07 (s, 3H), 4.04 (dd, J=8.0, 2.8 Hz, 1H), 4.24 (m, 1H), 4.41 (dd, J=12.0, 2.8 Hz, 1H), 5.73 (d, J=4.8 Hz, 1H), 6.24 (d, J=4.4 Hz, 1H), 6.89 (br s, 2H), 8.36 (s, 1H); MS (ESI) [(M+H)$^+$] found 441.08. Elemental analysis for (C$_{17}$H$_{20}$N$_4$O$_8$S.0.3H$_2$O): C, 45.80; H, 4.66; N, 12.57. Found C, 45.84; H, 4.50; N, 12.47.

Example 35

Preparation of 5-Amino-3-(5'-(1,2-diacetoxy-ethyl), 2',3'-di-O-acetyl-β-D-glucofuranosyl)-3H-thiazolo[4,5-d]pyrimidin-2-one (106)

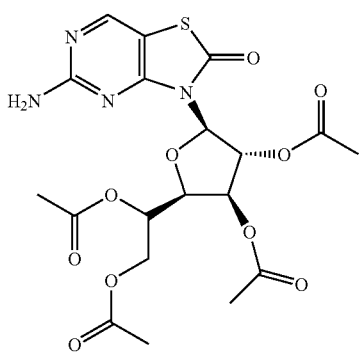
106

The required sugar, penta-O-acetylglucofuranose (108) was prepared as described below.

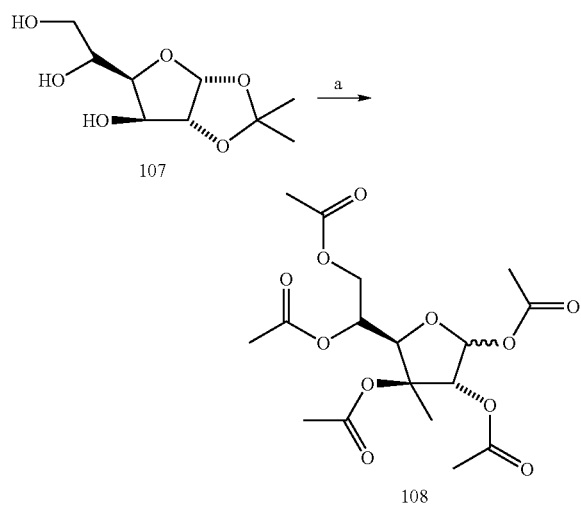
107
108
a. H$_2$SO$_4$, Ac$_2$O — AcOH

Step 1: Penta-O-acetylglucofuranose (108)

1,2-O-Isopropylidine-α-D-glucofranose (107) (5 g, 22.7 mmol) was dissolved in acetic acid (180 ml) and acetic anhydride (21.5 ml), cooled in a cool water bath and sulfuric acid (0.02 ml, 98%) was added and the mixture stirred 24 hours at ambient temperature. The mixture was poured onto 500 g of ice, water was added and this was extracted four times with methylene chloride. The organic portions were combined, washed twice with saturated sodium bicarbonate, dried (MgSO$_4$), and filtered to yield an oily residue. This was purified on a 120 g silica gel column using a gradient of ethyl acetate in hexane (20-100%) to give 5.33 g (13.66 mmol, 60%) of 18 as an oil whose spectra are consistent with a mixture of anomers. $^1$H NMR (400 MHz, CDCl$_3$) δ 6.41 (d, J=3.6 Hz), 6.12 (s), 5.58 (m), 5.41 (d, J=3.6 Hz), 5.20-5.37 (m), 4.56-4.62 (m), 4.02-4.18 (m), 2.00-2.13 (m).

Step 2: Preparation of 5-Amino-3-(5'-(1,2-diacetoxy-ethyl), 2',3'-di-O-acetyl-β-D-glucofuranosyl)-3H-thiazolo[4,5-d]pyrimidin-2-one (106)

In a manner similar to Example 23, step 1, using penta-O-acetylglucofuranose (108), afforded 80 mg (9%) of 106 as a white solid: $^1$H NMR (400 MHz CDCl$_3$) δ 2.07 (s, 6H), 2.09 (s, 3H), 2.14 (s, 3H), 4.03-4.07 (m, 1H), 4.47 (dd, J=6.4, 2 Hz, 1H), 4.67 (dd, J=12.4, 2.0 Hz, 1H), 5.31 (br s, 2H), 5.58-5.6 (m, 1H), 5.68 (m 1H), 5.97 (d, J=5.6 Hz, 1H), 6.10 (dd, J=3.6, 2 Hz, 1H), 8.16 (s, 1H); MS (ESI [(M+H)$^+$] found 499.40. Elemental analysis for (C$_{19}$H$_{22}$N$_4$O$_{10}$S.0.1 IPA): C, 45.95; H, 4.56; N, 11.11. Found C, 45.92; H, 4.76; N, 10.80.

Example 36

Preparation of 5-Amino-3-(3'-acetoxymethyl-2',3',5'-tri-O-acetyl-β-D-xylofuranosyl)-3H-thiazolo[4,5-d]pyrimidin-2-one (109)

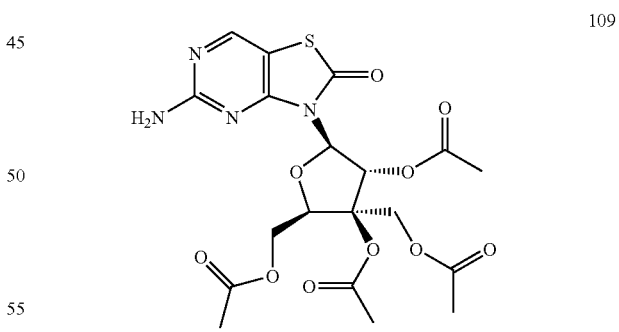
109

The required sugar, tetra-O-acetyl-3-acetoxymethyl-D-xylofuranos α and β mixture (113) was prepared as follows:

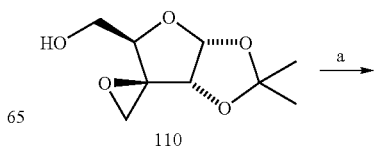
110

-continued

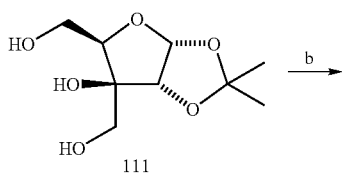

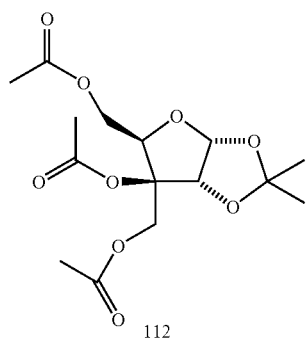

a. NaOH, dioxane  b. Acetic Anhydride, Pyridine, c. H₂SO₄, Ac₂O — AcOH

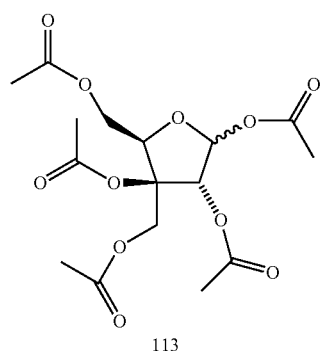

Step 1: 1,2-O-isopropylidfene-3(S)-(hydroxy-hydroxymethyl)-D-xylofuranose (111)

The epoxide 110 [prepared as described by Lu and Just; *Tetrahedron Letters* 41 (2000) 9223-9227] (1.68 g, 8.3 mmol) was dissolved in dioxane (9 ml) and 1.0M NaOH was added (16.6 ml, 16.6 mmol) and the reaction heated to 50 degrees for 30 minutes. The reaction was cooled to ambient temperature, 16.6 ml of 1.0 M HCl and 100 ml of absolute ethanol were added, stirred 5 minutes and the mixture evaporated under vacuum to give a solid. The solid was suspended in 200 ml of $CH_2Cl_2$ and sonicated to give a very fine suspension of solid. This was dried ($MgSO_4$), filtered through Celite and evaporated to give 111 as a thick oil (1.81 grams, 8.22 mmol, 99%). $^1H$ NMR (400 MHz, CDCl3) δ 5.94 (d, J=3.6 Hz, 1H), 4.4 (d, J=4 Hz, 2H), 4.03 (m, 2H), 3.83 (d, J=11.6, 1H), 3.78 (d, J=12 Hz, 1H), 2.66 (bs, 2H, OH), 1.7 (bs, 1H, OH), 1.52 (s, 3H), 1.33 (s, 3H)

Step 2: 1,2-O-isopropylidene-3-(acetoxy-methylacetoxy)-5-O-acetyl-D-xylofuranose (112)

The triol 111 (1.81 g, 8.22 mmol) was dissolved in pyridine (30 ml), acetic anhydride (7.75 ml, 82 mmol) was added followed by DMAP (50 mg) and the mixture stirred for 72 hours. The volatiles were evaporated under vacuum and the residue partioned between methylene chloride and saturated ammonium chloride. The aqueous phase was extracted twice methylene chloride and the organic portions combined, dried ($MgSO_4$), filtered and the solvent evaporated to get 2.83 g of an oil. The residue was purified using flash chromatography on a 120 g silica gel column using a gradient of ethyl acetate in hexane (10-80%) to yield 1.82 g (5.26 mmol, 64%) of 112 as a clear oil. %). $^1H$ NMR (400 MHz, $CDCl_3$) δ 5.92 (d, J=3.6 Hz, 1H), 5.02 (m, 2H), 4.51-4.58 (m, 2H), 4.35 (dd, J=8.4 Hz, J=2.8 Hz, 1H), 4.16-4.22 (m, 1H), 2.10 (s, 3H), 2.09 (s, 3H), 2.08 (s, 3H), 1.53 (s, 3H), 1.32 (s, 3H)

Step 3: Tetra-O-acetyl-3-(acetoxymethyl)-D-xylofuranose, α and β Mixture (113)

The triacetate 112 (1.74 g, 5.01 mmol) was dissolved in acetic acid (45 ml), acetic anhydride was added (2.37 ml, 25 mmol) followed by sulfuric acid in acetic acid (0.5 ml of a 1.0M solution, 0.5 mmol) and this mixture was stirred overnight at ambient temperature. The reaction was diluted with methylene chloride (70 ml) and washed with water. The water layer was extracted twice with methylene chloride. The organic portions were combined, transferred to a large beaker and saturated sodium bicarbonate was added. To this was added solid sodium bicarbonate until no more bubbling is observed. Separate the organic phase, extract the aqueous phase with methylene chloride, combine the organic phases and dry ($MgSO_4$), filter and evaporate to get an oil that was further taken to dryness with toluene to yield 113 as a clear oil (1.91 g, 3.89 mmol, 97%) whose NMR is consistent with a mixture of anomers. $^1H$ NMR (400 MHz, $CDCl_3$) δ 6.42 (d, J=4.4 Hz), 6.05 (d, J=1.6 Hz), 5.79 (d, J=1.6 Hz), 5.5 (d, J=4.4 Hz), 4.89-4.93 (m), 4.12-4.58 (m), 2.04-2.2 (many singlets).

Step 4: Preparation of 5-Amino-3-(3'-acetoxymethyl-2',3',5'-tri-O-acetyl-β-D-xylofuranosyl)-3H-thiazolo[4,5-d]pyrimidin-2-one (109)

In a manner similar to Example 23, step 1, using tetra-O-acetyl-3-acetoxymethyl-D-xylofuranos α and β mixture (113) afforded 272 mg (37%) of 109 as a white solid: $^1H$ NMR (400 MHz (DMSO-$d_6$) δ 2.03 (s, 3H), 2.05 (s, 3H), 2.07 (s, 3H), 2.09 (s, 3H), 4.20 (m, 1H), 4.44-4.57 (m, 3H), 4.79 (d, J=12.4 Hz, 1H), 5.84 (d, J=5.6 Hz, 1H), 6.38 (d, J=6 Hz, 1H), 6.87 (br s, 2H), 8.37 (s, 1H); MS (ESI) [(M+H)$^+$] found 499.12. Elemental analysis for ($C_{19}H_{22}N_4O_{10}S.0.1H_2O$): C, 45.61; H, 4.47; N, 11.20. Found C, 45.93; H, 4.44; N, 10.83.

Example 37

Preparation of 5-Amino-3-(2',3',5'-tri-O-acetyl-β-D-xylofuranosyl)-3H-thiazolo[4,5-d]pyrimidin-2-one (114)

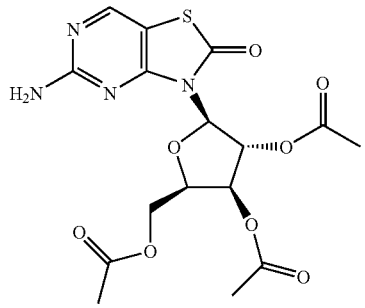

114

Step 1: Preparation of 5-Amino-3-(2',3',5'-tri-O-acetyl-β-D-xylofuranosyl)-3H-thiazolo[4,5-d]pyrimidin-2-one (114)

In a manner similar to Example 23, step 1, using commercially available tetra-O-acetylxylofuranose, afforded 110 mg (14%) of 114 as a white solid: $^1$H NMR (400 MHz (CDCl$_3$) δ 2.08 (s, 3H), 2.10 (s, 3H), 2.18 (s, 3H), 4.42-4.45 (m, 2H), 4.52-4.56 (m, 1H), 5.13 (br s, 2H), 5.49 (dd, J=3.6, 2.4 Hz, 1H), 6.00 (d, J=5.2 Hz, 1H), 6.22 (dd, J=4, 1.6 Hz, 1H), 8.15 (s, 1H); MS (ESI) [(M+H)$^+$] found 426.93. Elemental analysis for (C$_{16}$H$_{18}$N$_4$O$_8$S): C, 45.07; H, 4.25; N, 13.14. Found C, 44.86; H, 4.17; N, 13.05.

Example 38

5-Amino-3-(3'-C-methyl-β-D-ribofuranosyl)thiazolo[4,5-d]pyrimidine-2,7(3H,6H)-dione (117)

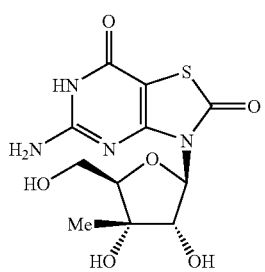

117

Step 1) Preparation of 5-Amino-3-(3'-O-acetyl-2',5'-di-O-benzoyl-3'-C-methyl-β-D-ribofuranosyl)thiazolo[4,5-d]pyrmidine-2,7(3H,6H)-dione (116)

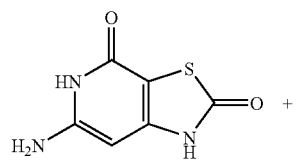

4

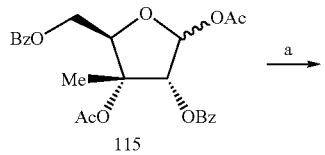

115

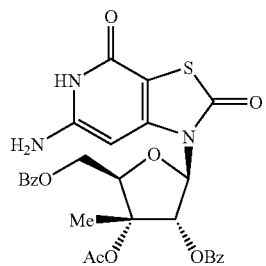

116 a. BSA, MeCN, rt, 1 h; + sugar, TMSOTf, 60° C., 1 h, 45%.

5-Amino-3H,6H-thiazolo[4,5-d]pyrimidine (116 mg, 0.631 mmol), 3'-C-methyl-ribfuranose 11 (272 mg, 0.598 mmol) [prepared according to the method of Giradet, et. al. *J. Med. Chem.* 2000, 43, 3704-3713], BSA (0.462 ml, 1.89 mmol) and acetonitrile (5 mL) were mixed vigorously at ambient temperature for 40 min. Once a homogeneous solution was obtained, the reaction was charged with TMSOTf (0.171 mL, 210 mg). Then the reaction was heated to 60° C. After 1 h the solvent was removed by rotary evaporation. The resultant solid was dissolved in ethyl acetate (10 mL) and extracted with saturated sodium bicarbonate (2×5 mL). The aqueous phase was then back extracted with ethyl acetate (5 mL) and the organic layers were combined. A solid impurity promptly precipitated out of the organic phase, this was filtered off and discarded. The organic phase was concentrated and the resultant solid then triturated in ether (5 mL) yielding 167 mg (45%) of tan solid: $^1$H NMR (400 MHz, d$_6$-DMSO) δ 12.2 (br s, 1H), 8.01 (m, 4H), 7.83 (m, 2H), 7.53 (m, 4H), 7.28 (br s, 2H), 6.4 (m, 1H), 6.02 (m, 1H), 4.82-4.67 (m, 2H), 3.38 (s, 1H), 2.01 (s, 3H), 1.98 (s, 3H); [M+H]$^+$ m/z 581.

Step 2) Preparation of 5-Amino-3-(3'-C-methyl-β-D-ribofuranosyl)thiazolo[4,5-d]pyrimidine-2,7(3H,6H)-dione (117)

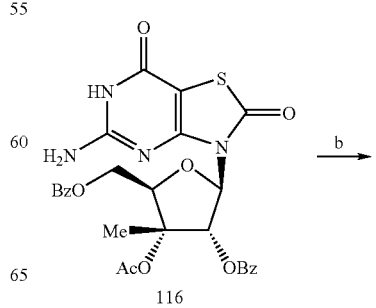

116

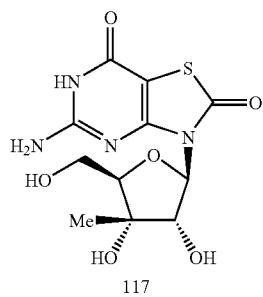

117 b. K₂CO₃, MeOH, rt, 74%.

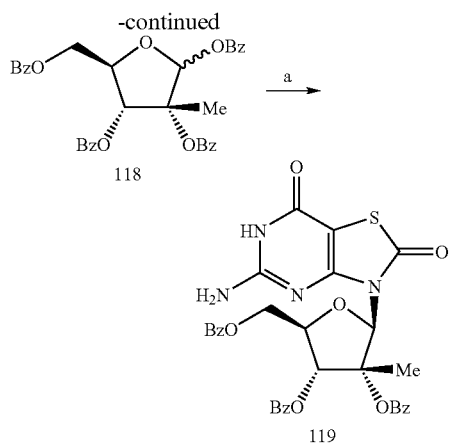

119 a. BSA, MeCN, 80° C., 2.5 h; + sugar, SnCl₄, 80° C., 1.5 h, 42%.

Nucleoside triester 116 (100 mg, 0.172 mmol) was dissolved in methanol (5 mL) and K₂CO₃ (28.6 mg, 0.207 mmol) was added. The reaction progressed for 16 h. The reaction was neutralized with acetic acid (24.8 mg, 0.412 mmol). Then the solvent removed by rotary vacuum and the solid submitted to HPLC purification (MeCN—H₂O) yielding 42 mg (74%) of white solid: $^1$H NMR (400 Mz, d$_6$-DMSO) δ 11.20 (s, 1H), 6.89 (br s, 2H), 5.80 (d, J=8.0, 1H), 5.36 (d, J=6.0, 1H), 4.77 (t, J=8.0, 1H), 4.62 (s, 1H), 4.48 (m, 1H), 3.75 (m, 1H), 3.58-3.44 (m, 2H), 1.19 (s, 3H); Analysis calc'd for C$_{14}$H$_{14}$N$_4$O$_6$S.0.125H$_2$O.0.125HCO$_2$H: C, 39.33; H, 4.34; N, 16.43; S, 9.40. Found: C, 39.77; H, 4.81; N, 15.02; S, 9.69; [M+H]$^+$ m/z 331.

To a suspension of heterocycle 4 (268 mg, 1.44 mmol) in anhydrous MeCN (8 mL) at rt was added BSA (971 uL, 3.93 mmol). The resultant mixture was heated to 80° C. for 2.5 h whereupon 2-C-methyl-β-D-ribofuranose 118 [prepared according to Wolfe et al. *J. Org. Chem.* 1997, 62, 1754-1759] (760 mg, 1.31 mmol) was added as a solution in MeCN (6 mL). To this mixture was added SnCl₄ (276 uL, 2.35 mmol), and stirring at 80° C. was continued for an additional 1.5 h. TLC analysis with 10% MeOH—CHCl₃ indicated that the reaction was complete. The mixture was cooled to rt, diluted with EtOAc (150 mL), and partitioned with a 1:1 mixture (100 mL) of brine-NaHCO₃. The aqueous phase was further extracted with EtOAc (50 mL), and the combined organic phases were dried over Na₂SO₄, filtered and concentrated. The residue was submitted to HPLC (SiO₂, 0-4% MeOH-DCM) to afford 353 mg (42%) of a white solid: $^1$H (400 MHz, DMSO-d$_6$) δ 11.3 (br s, 1H), 7.93-8.08 (br m, 3H), 7.85-7.87 (m, 2H), 7.33-7.66 (m, 10H), 6.97 (br s, 2H), 6.64 (s, 1H), 6.16-6.26 (br m, 1H), 4.56-4.79 (br m, 3H), 1.79 (s, 3H); M$^+$ m/z 642.

Example 39

5-Amino-3-(2'-C-methyl-β-D-ribofuranosyl)-3H,6H-thiazolo[4,5-d]pyrimidine-2,7-dione (120)

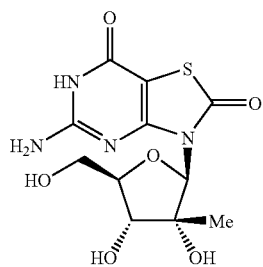

120

Step 1) Preparation of 5-Amino-3-(2',3',5'-tri-O-benzoyl-2'-C-methyl-β-D-ribofuranosyl)-3H,6H-thiazolo[4,5-d]pyrimidine-2,7-dione (119)

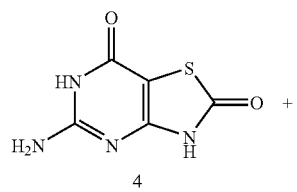

4

Step 2) Preparation of 5-Amino-3-(2'-C-methyl-β-D-ribofuranosyl)-3H,6H-thiazolo[4,5-d]pyrimidine-2, 7-dione (120)

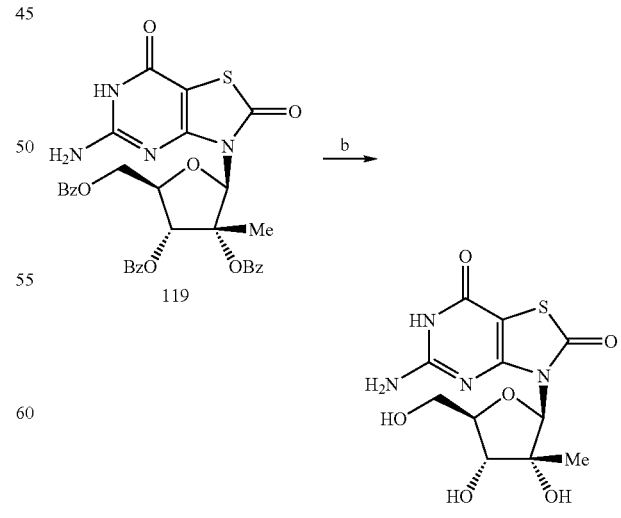

b. NH₃ (g), MeOH, rt, 34%.

A mixture of nucleoside triester 119 (209 mg, 0.325 mmol) and MeOH (10 mL) saturated with NH₃ (g) at −30° C. was DMSO-d$_6$) δ 11.18 (s, 1H), 6.92 (br s, 2H), 5.95 (s, 1H), 5.18-5.28 (br m, 1H), 4.75 (br s, 1H), 4.53 (dd, J=11.3, 5.46, 1H), 3.95 (br s, 1H), 3.73-3.78 (m, 1H), 3.29 (br s, 2H), 1.04 (s, 3H); [M+H]$^+$ m/z 331.

Example 40

5-Amino-3-(3'-deoxy-β-D-ribofuranosyl)-3H,6H-thiazolo[4,5-d]pyrimidine-2,7-dione (122)

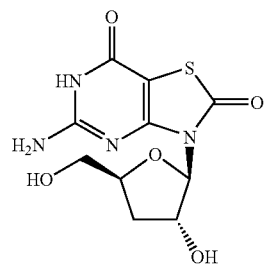

122

Step 1) Preparation of 5-Amino-3-(2',5'-di-O-acetyl-3'-deoxy-β-D-ribofuranosyl)-3H,6H-thiazolo[4,5-d]pyrimidine-2,7-dione (121)

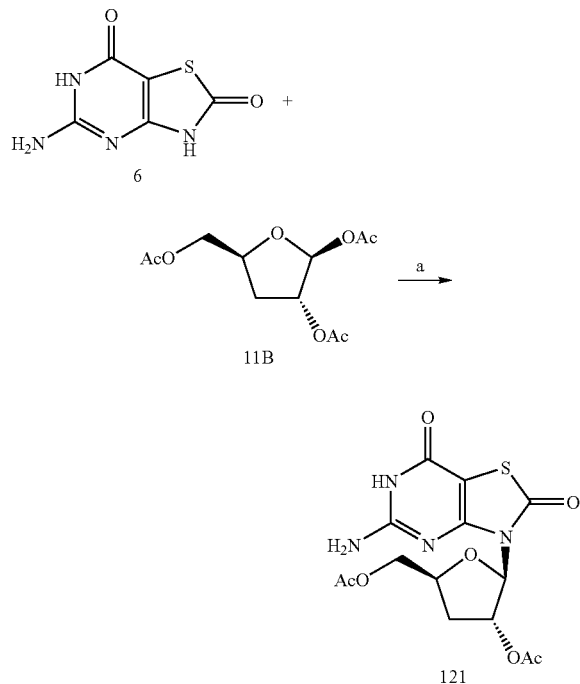

a. BSA, MeCN, rt, 1 h; + sugar, TMSOTf, 60° C., 1 h, 45%.

To a suspension of heterocycle 6 (4.60 g, 25.0 mmol) and deoxyribofuranose 11B (5.42 g, 20.8 mmol) in MeCN (83 mL) at rt was added BSA (15.3 mL, 62.5 mmol). The resultant mixture was immersed into a 40° C. oil bath for 1.5 h, and TMSOTf (5.65 mL, 31.2 mmol) was added dropwise. The thick reaction mixture was immersed into an 80° C. oil bath and stirred for 2.5 h whereupon it was concentrated via rotary evaporation to a residue that was partitioned between EtOAc (300 mL) and pH 7 buffer (100 mL). The organic phase was dried over Na$_2$SO$_4$ and concentrated to a residue that was triturated with EtOAc and then filtered to yield 2.31 g (29%) of fine white solid. The filtrate was concentrated to a residue that was submitted to flash chromatography (SiO$_2$, 0-6% MeOH-DCM) to afford 1.12 g (14%) of very fine pale yellow solid. Altogether, there was a 43% combined yield of nucleoside 121: $^1$H (400 MHz, DMSO-d$_6$) δ 11.23 (s, 1H), 6.95 (br s, 2H), 5.79 (d, J=2.0, 1H), 5.59 (d, J=7.2, 1H), 4.28-4.34 (m, 1H), 4.22 (dd, J=3.2, 12.0, 1H), 3.99 (dd, J=6.4, 11.6, 1H), 2.56-2.65 (m, 1H), 2.04 (s, 3H), 1.98 (s, 3H), 1.97-2.04 (m, 1H); [M+H]$^+$ m/z 384.8. Analysis cal'd for: C$_{14}$H$_{16}$N$_4$O$_7$S.0.5H$_2$O: C, 42.74; H, 4.36; N, 14.24; S, 8.15. Found: C, 42.72; H, 4.22; N, 14.15; S, 8.19.

Step 2) Preparation of 5-Amino-3-(3'-deoxy-β-D-ribofuranosyl)-3H,6H-thiazolo[4,5-d]pyrimidine-2,7-dione (122)

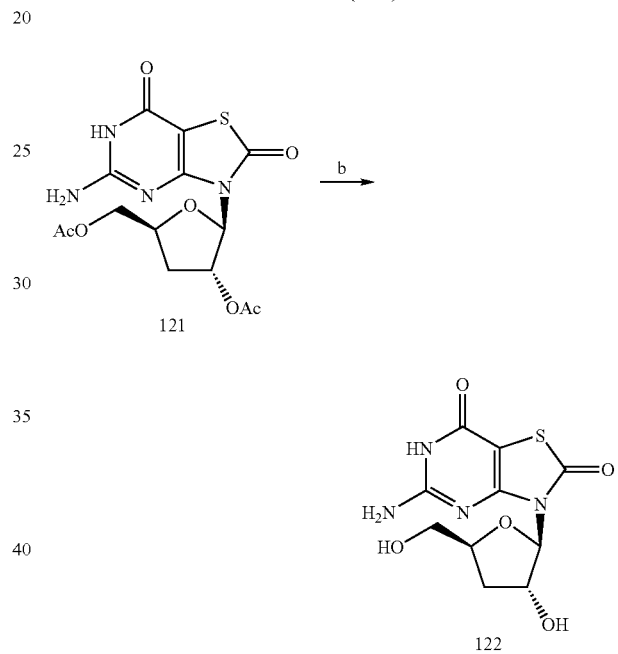

b. K$_2$CO$_3$, MeOH, rt, 74%.

To a suspension of nucleoside diester 121 (1.91 g, 4.97 mmol) in MeOH (50 mL) at rt was added K$_2$CO$_3$ (820 mg, 5.97 mmol). The reaction mixture was stirred for 18 h, then quenched with HOAc (0.68 mL, 12 mmol), stirred 30 min, and finally concentrated via rotary evaporation. The residue was azeotroped with toluene (3×50 mL), and then triturated with water (250 mL). The solid material was filtered, washed with water (2×250 mL), air dried, triturated with ether (250 mL), and filtered to provide 1.17 g (62%) of nucleoside 122 as an off-white solid: $^1$H (400 MHz, DMSO-d$_6$) δ 11.26 (br s, 1H), 6.93 (br s, 1H) 7.14 (d, J=2.4, 1H), 5.39 (d, J=4.4, 1H), 4.74-4.79 (m, 1H), 4.65 (t, J=5.6, 1H), 4.09-4.16 (m, 1H), 3.41-3.43 (m, 2H), 2.23-2.30 (m, 1H), 1.78 (ddd, J=2.4, 6.4, 8.4, 1H) 1.76-1.81 (m, 1H); [M+H]$^+$ (m/z 301.5. Analysis cal'd for: C$_{10}$H$_{12}$N$_4$O$_5$S.1.25H$_2$O: C, 37.20; H, 4.53; N, 17.36; S, 9.93. Found: C, 37.06; H, 4.27; N, 17.14; S, 9.84.

Example 41

5-Amino-3-(2'-deoxy-β-D-ribofuranosyl)-3H,6H-thiazolo[4,5-d]pyrimidine-2,7-dione (130)

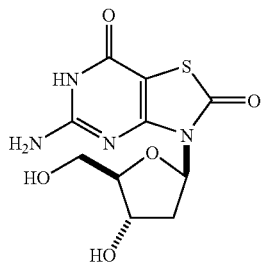
130

Step 1) Preparation of 5-N-Acetyl-amino-3-(β-D-ribofuranosyl)-3H,6H-thiazolo[4,5-d]pyrimidine-2,7-dione

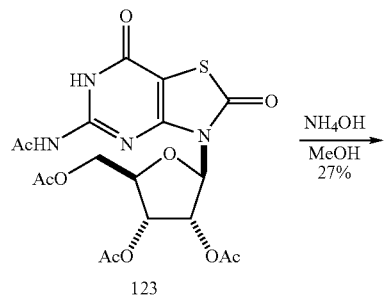

To a suspension of isatoribine tetraacetate 123 [CAS #533897-42-6, prepared according to Webber et. al. U.S. Pat. No. 6,924,271] (12.3 g, 25.4 mmol) in MeOH (180 mL) was added concentrated NH₄OH (180 mL). The resultant mixture was stirred 1 h whereupon it was concentrated and submitted to flash chromatography (SiO₂, 15-30% IPA-CHCl₃) to afford 2.50 g (27%) of acetamide 124 as a white solid: [M+H]⁺ m/z 359.

Step 2) Preparation of 5-N-Acetyl-amino-3-(5'-O-tert-butyldimethylsilyl-β-D-ribofuranosyl)-3H,6H-thiazolo[4,5-d]pyrimidine-2,7-dione

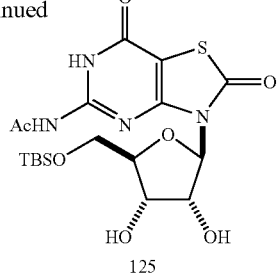
125

To a solution of triol 124 (2.48 g, 6.93 mmol) in DMF (15 mL) was added sequentially imidazole (943 mg, 13.9 mmol) and TBSCl (1.04 g, 6.93 mmol) at rt. The resultant mixture was stirred 1 h, then diluted with EtOAc (300 mL) and extracted with water (2×100 mL) then brine (100 mL). The organic phase was dried over Na₂SO₄, concentrated and triturated with ether to afford 2.18 g (67%) of siloxane 125 as an off-white solid: ¹H (400 MHz, DMSO-d₆) δ 12.16 (br s, 1H), 11.81 (br s, 1H), 5.81 (d, J=4.77, 1H), 5.34 (d, J=5.13, 1H), 5.03 (d, J=5.50, 1H), 4.79 (dd, J=10.3, 5.13, 1H), 4.13 (dd, J=10.6, 5.5, 1H), 3.71-3.78 (m, 2H), 3.40-3.64 (m, 1H), 2.18 (s, 3H), 0.84 (s, 9H), 0.00 (s, 6H); [M+H]⁺ m/z473.

Step 3) Preparation of 5-N-Acetyl-amino-3-(5'-O-tert-butyldimethylsilyl-2',3'-thioxo-β-D-ribofuranosyl)-3H,6H-thiazolo[4,5-d]pyrimidine-2,7-dione

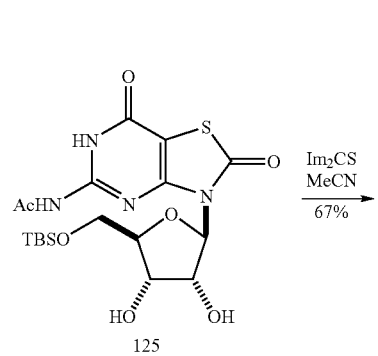

To a solution of diol 125 (1.00 g, 2.12 mmol) in MeCN (50 mL) was added TCDI (754 mg, 4.23 mmol) at rt. The resultant mixture was stirred for 18 h whereupon it was concentrated, submitted to flash chromatography (SiO₂, 40% EtOAc—CHCl₃), and triturated with ether to afford 730 mg (67%) of a white solid: ¹H (400 MHz, DMSO-d₆) δ 12.18 (br s, 1H), 11.75 (br s, 1H), 6.21-6.24 (m, 2H), 5.79 (br s, 1H), 4.35 (br s, 1H), 3.72 (br d, J=6.6, 2H), 2.21 (s, 3H), 0.84 (s, 9H), 0.01 (s, 6H); [M+H]⁺ m/z 515.

Step 4) Preparation of 5-N-Acetyl-amino-3-(5'-O-tert-butyldimethylsilyl-2'-deoxy-β-D-ribofuranosyl)-3H,6H-thiazolo[4,5-d]pyrimidine-2,7-dione

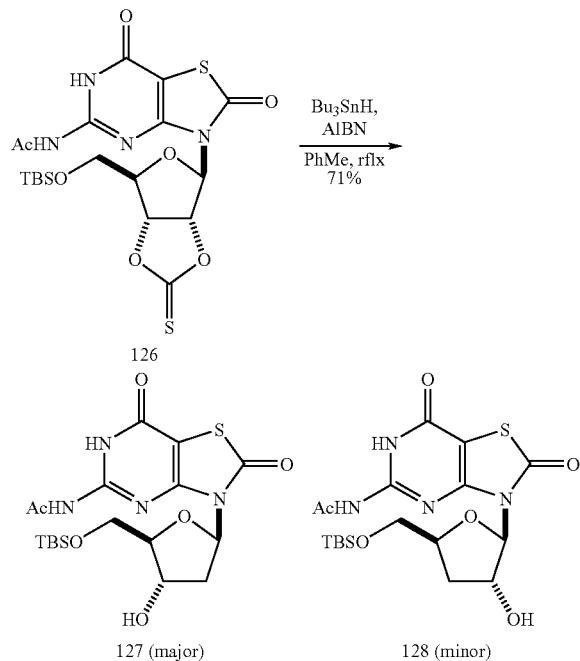

126

127 (major)    128 (minor)

To a suspension of thiocarbonate 126 (712 mg, 1.38 mmol) and Bu$_3$SnH (2.66 mL, 10.0 mmol) in anhydrous toluene (140 mL) was added AIBN (30 mg, 0.18 mmol) at rt. The mixture was immersed into a 130° C. oil bath for 15 min then removed, cooled, concentrated and submitted to flash chromatography (SiO$_2$, 80-100% EtOAc—CHCl$_3$) to afford 450 mg (71%) of a mixture (2:1) of 2'-deoxy and 3'-deoxy regioisomers (major isomer reported): $^1$H (400 MHz, DMSO-d$_6$) δ 12.12 (br s, 1H), 11.82 (br s, 1H), 6.26 (t, J=7.0, 1H), 5.22 (d, J=4.0, 1H), 4.31-4.34 (m, 1H), 3.69-3.75 (m, 2H), 3.57-3.62 (m, 1H), 2.93-2.99 (m, 1H), 2.18 (s, 3H), 2.00-2.18 (m, 1H), 0.84 (s, 9H), 0.00 (s, 6H); [M+H]$^+$ m/z 457.

Step 5) Preparation of 5-N-Acetyl-amino-3-(2'-deoxy-β-D-ribofuranosyl)-3H,6H-thiazolo[4,5-d]pyrimidine-2,7-dione

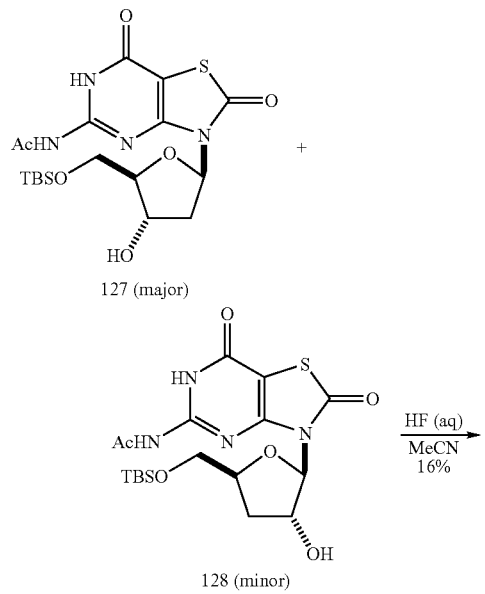

127 (major)

128 (minor)

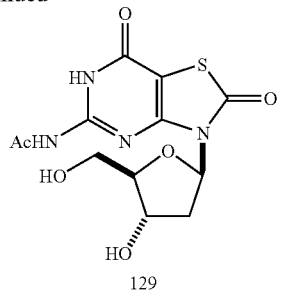

129

To a suspension of the regioisomers (744 mg, 1.60 mmol) from Step 4 (above) in MeCN (30 mL) at rt was added 48% aqueous HF (1.67 mL). The reaction mixture was stirred 1 h whereupon it was concentrated to a purple residue that was submitted to flash chromatography (SiO$_2$, 1.5-15% MeOH-DCM), affording 503 mg (92%) of a mixture of regioisomers that was further purified via HPLC (MeCN—H$_2$O) to provide 169 mg (31%) of nucleoside 129 as a white solid after lyophilization: $^1$H (400 MHz, DMSO-d$_6$) δ 12.14 (s, 1H), 11.85 (s, 1H), 6.26 (t, J=7.0, 1H), 4.30-4.32 (m, 1H), 3.69-3.71 (m, 1H), 3.38-3.53 (m, 4H), 2.92-2.98 (m, 1H), 2.19 (s, 3H), 1.97-2.03 (s, 1H); [M+H]$^+$ m/z 343.

Step 6) Preparation of 5-Amino-3-(2'-deoxy-β-D-ribofuranosyl)-3H,6H-thiazolo[4,5-d]pyrimidine-2,7-dione

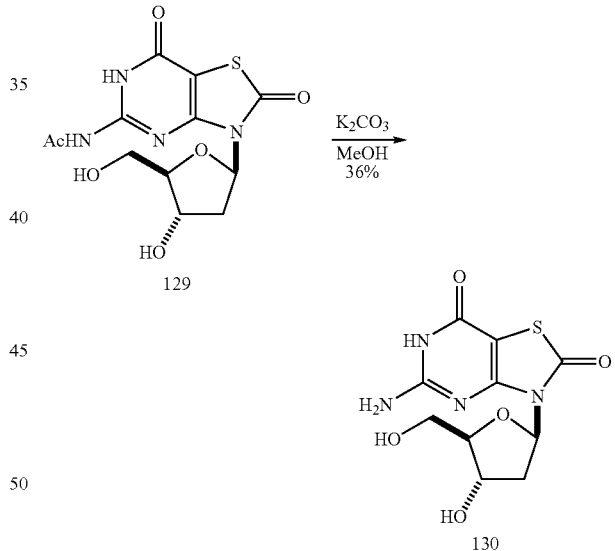

To a solution of acetamide 129 (169 mg, 0.494 mmol) in MeOH (10 mL) was added K$_2$CO$_3$ (158 mg, 1.14 mmol) at rt. The resulting mixture was stirred for 8 h whereupon it was quenched with HOAc (137 uL, 2.40 mmol), concentrated and submitted to HPLC (MeCN—H$_2$O) to afford 125 mg (84%) of the title compound 130 as a white solid after lyophilization: $^1$H (400 MHz, DMSO-d$_6$) δ 11.16 (s, 1H), 6.90 (br s, 2H), 6.22 (t, J=7.0, 1H), 4.27-4.31 (m, 1H), 3.67-3.71 (m, 1H), 3.52 (dd, J=11.3, 5.5, 1H), 3.40 (dd, J=11.7, 6.2, 1H), 2.86-2.93 (m, 1H), 1.97 (ddd, J=12.9, 7.0, 3.5, 1H); [M+H]$^+$ m/z 301. Analysis calc'd for C$_{10}$H$_{12}$N$_4$O$_5$S.H$_2$O: C, 37.73; H, 4.43; N, 17.60; S, 10.07. Found: C, 38.13; H, 4.27; N, 17.40; S, 9.89.

119

Scheme 7

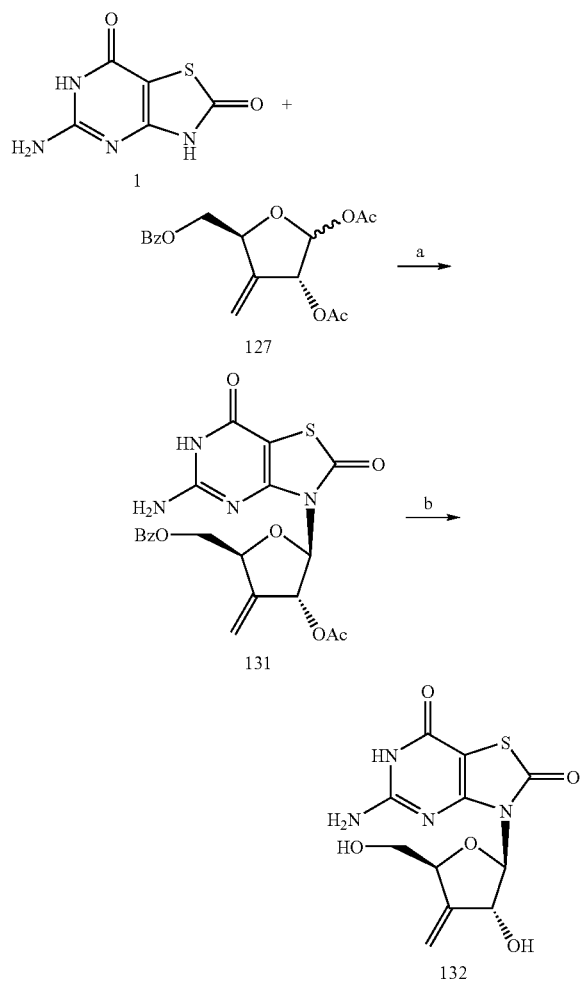

a) BSA, TMSOTf, CH3CN, 80° C., 3-4 h
b) K2CO3, DMF, rt, overnight

Example 42

Preparation of 5-Amino-3-(3'-deoxy-3'-methylidene-β-D-ribofuranosyl)-3H,6H-thiazolo[4,5-d]pyrimidine-2,7-dione (132)

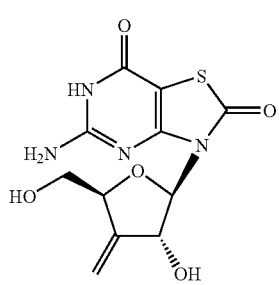

120

Step 1: Preparation of 5-Amino-3-(2'-O-acetyl-5'-O-benzoyl-3'-deoxy-3'-methylidene-β-D-ribofuranosyl)-3H,6H-thiazolo[4,5-d]pyrimidine-2,7-dione (131)

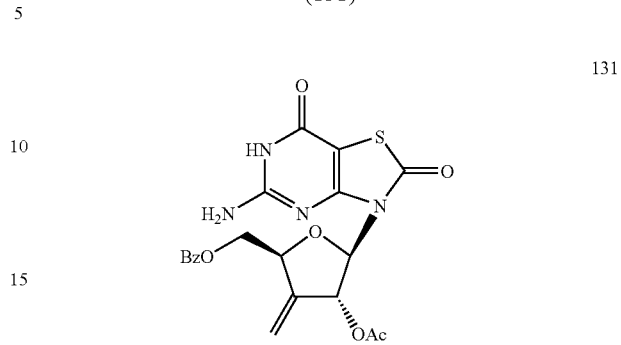

1,2-di-O-acetyl-5-O-benzoyl-3-deoxy-3-methylidene-α,β-D-ribofuranose (127) (132 mg, 0.39 mmol) [prepared according to the method of Girardet et al. *J. Med. Chem.* 2000, 43, 3704-3713] was dissolved in acetonitrile (5 mL) at ambient temperature. 5-Amino-3H,6H-thiazolo[4,5-d]pyrimidine-2,7-dione (1) (73 mg, 0.39 mmol) was added, the mixture was then stirred for 0.5 h before it was heated to 40° C. After 5 min at 40° C., BSA (0.29 mL, 1.18 mmol) was added and the mixture was stirred for another 0.5 h. The mixture was then heated to 80° C. TMSOTf (0.107 mL, 0.59 mmol) was added and the reaction was stirred for 3-4 hours at 80° C. Upon completion, the reaction was allowed to cool to room temperature and then quenched by a pH 7.0 buffer (1.0 M $K_2HPO_4$ and 1.0 M $NaH_2PO_4$, 2 ml). The mixture was extracted with $CH_2Cl_2$ (3×10 mL). The combined organic layers were washed with brine, dried with $Na_2SO_4$, and concentrated in vacuo. The crude product was purified by column chromatography ($SiO_2$, 0-10% MeOH—$CH_2Cl_2$ to afford 23 mg (13%) of 131 as a light yellow solid: $^1$H NMR (400 MHz, CDCl$_3$) δ 9.85 (s, 1H), 8.03 (d, J=8, 2H), 7.54 (m, 1H), 7.417 (t, J=8, 2H), 6.50 (s, 2H), 6.07 (d, J=4.8, 1H), 5.73 (m, 1H), 5.37 (d, J=32, 2H), 4.83 (m, 2H), 4.46 (m, 1H), 2.00 (s, 3H); [M+H]$^+$ 459.3; Elemental analysis for $C_{20}H_{18}N_4O_7S \cdot 0.7EtOAc$: calc'd: C, 52.65; H, 4.57; N, 10.77; S, 6.16. found: C, 53.59; H, 4.57; N, 10.83; S, 6.17.

Step 2: Preparation of (3'S)-5-Amino-3-(3'-deoxy-3'-methylidene-β-D-ribofuranosyl)-3H,6H-thiazolo[4,5-d]pyrimidin-2,7-dione (132)

(3'S)-5-Amino-3-(3'-acetoxymethyl-2',5'-di-O-acetyl-3'-deoxy-β-D-ribofuranosyl)-3H-thiazolo[4,5-d]pyrimidin-2-one 131 (113 mg, 0.25 mmol) was dissolved in methanol (5 mL) at ambient temperature. Potassium carbonate (38 mg, 0.27 mmol) was added and the mixture was stirred at room temperature overnight. Upon completion, acetic acid was added (34 μL) and the mixture was stirred another 30 minutes at room temperature. The mixture was concentrated, purified by HPLC, then triturated by EtOAc to afford 49 mg (64%) of 132 as a white solid: $^1$H NMR (400 MHz, DMSO-d$_6$) δ 11.563 (s, 1H), 6.82 (s, 2H), 5.80 (m, 1H), 5.62 (m, 1H), 5.16 (d, J=14.4, 2H), 4.51 (m, 1H), 3.53 (m, 2H), 1.89 (s, 2H); [M+H]$^+$ 313.07.

Example 43

Preparation of 5-Amino-3-(2',3',5'-tri-hydroxy-β-D-xylofuranosyl)-3H,6H-thiazolo[4,5-d]pyrimidin-2-one (134)

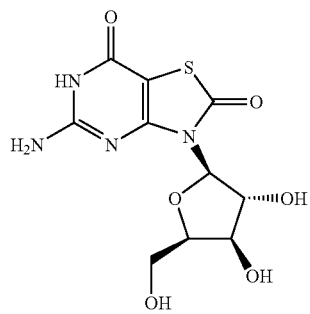

134

Step 1: Preparation of 5-Amino-3-(2',3',5'-tri-O-acetyl-β-D-xylofuranosyl)-3H,6H-thiazolo[4,5-d]pyrimidin-2-one (133)

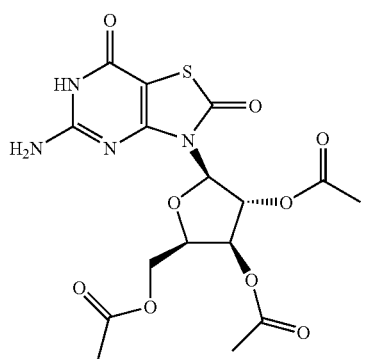

133

In a manner similar to Example 42, Step 1, using commercially available tetra-O-acetylxylofuranose, 740 mg of the title compound 133 was generated in 20% yield as a white solid: $^1$H NMR (400 MHz, $d_6$-DMSO) δ 11.32 (s, 1H), 6.98 (br s, 2H), 6.09 (dd, J=8.6, 2.3 Hz, 1H), 5.76 (d, J=5.5 Hz, 1H), 5.38 (dd, J=8.6, 2.3 Hz, 1H), 4.14 (m, 1H), 4.26 (m, 1H), 4.16 (m, 1H), 2.08 (s, 3H), 2.04 (s, 3H), 2.00 (s, 3H); [M+H]$^+$ 442.8; Elemental Analysis for $C_{16}H_{18}N_4O_9S \cdot 1.0H_2O$: calc'd: C, 41.74; H, 4.38; N, 12.17. found: C, 41.92; H, 4.23; N, 11.71.

Step 2: Preparation of 5-Amino-3-(2',3',5'-tri-hydroxy-β-xylofuranosyl)-3H,6H-thiazolo[4,5-d]pyrimidin-2-one (134)

In a manner similar to Example 42, Step 2, 43 mg of the title compound 134 was generated in 67% yield as a white solid: $^1$H NMR (400 MHz, $d_6$-DMSO) δ 11.24 (br s, 1H), 6.86 (br s, 2H), 5.60 (d, J=4.68 Hz, 1H), 5.57 (d, J=4.68 Hz, 1H), 5.04 (d, J=7.8 Hz, 1H), 4.64 (m, 1H), 4.41 (m, 1H), 3.87 (m, 2H), 3.54 (m, 2H); [M+H]$^+$ 316.9; Elemental Analysis for $C_{11}H_{14}N_4O_5S \cdot 1.3H_2O$: calc'd: C, 35.35; H, 4.33; N, 16.49. found: C, 35.73; H, 4.21; N, 16.15.

Example 44

Preparation of 5-Amino-3-(3'-(R)-octyloxy-β-D-xylofuranosyl)-3H,6H-thiazolo[4,5-d]pyrimidin-2-one (135)

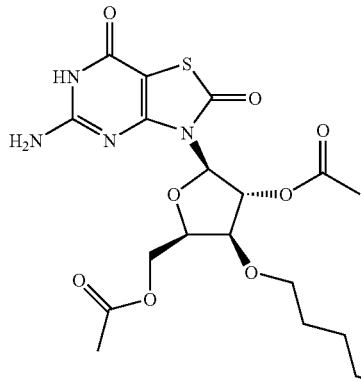

135

The required sugar acetic acid 1,2,5-tri-O-acetyl-3(S)-octyloxy-D-xylofuranose α and β mixture (94) was prepared as reported in Example 31.

Step 1: Preparation of 5-Amino-3-(3'-(R)-octyloxy-β-D-xylofuranosyl)-3H,6H-thiazolo[4,5-d]pyrimidin-2-one (135)

In a manner similar to Example 42, Step 1, 18.8 mg of the title compound 135 was generated from acetic acid 1,2,5-tri-O-acetyl-3(S)-octyloxy-D-xylofuranose α and β mixture (94) in 2% yield as a white solid: $^1$H NMR (400 MHz, $d_6$-DMSO) δ 11.21 (s, 1H), 6.94 (br s, 2H), 6.12 (m, 1H), 5.74 (d, J=6.2 Hz, 1H), 4.30 (m, 3H), 4.16 (m, 1H), 3.57 (m, 1H), 3.41 (m, 1H), 2.02 (d, J=8.6 Hz, 6H), 1.50 (m, 2H), 1.26 (m, 10H), 0.86 (m, 3H); [M+H]$^+$ 512.9; Elemental Analysis for $C_{22}H_{32}N_4O_8S$: calc'd: C, 51.55; H, 6.29; N, 10.93. found: C, 51.47; H, 6.37; N, 10.77.

Example 45

Preparation of 5-Amino-3-(3'-(R)-Methoxy-β-D-xylofuranosyl)-3H,6H-thiazolo[4,5-d]pyrimidin-2-one (137)

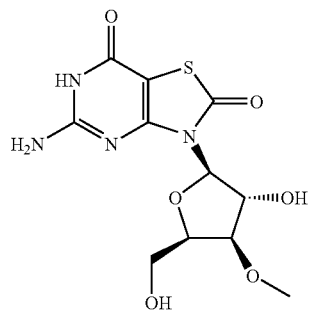

137

The required sugar, acetic acid 1,2,5-tri-O-acetyl-3)-methoxy-D-xylofuranose α and β mixture (91) was prepared as reported in Example 30.

123

Step 1: Preparation of 5-Amino-3-(3'-(R)-Methoxy-β-D-xylofuranosyl)-3H,6H-thiazolo[4,5-d]pyrimidin-2-one (136)

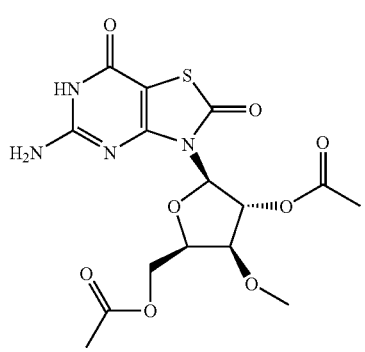

136

In a manner similar to Example 42, Step 1, 230 mg of the title compound 136 was generated from acetic acid 1,2,5-tri-O-acetyl-3)-methoxy-D-xylofuranose α and β mixture (91) in 31% yield as a white solid: $^1$H NMR (400 MHz, $d_6$-DMSO) δ 11.21 (s, 1H), 6.94 (br s, 2H), 6.14 (m, 1H), 5.74 (d, J=6.2 Hz, 1H), 4.33 (m, 2H), 4.18 (m, 2H), 3.35 (s, 3H), 3.30 (s, 3H), 2.04 (s, 3H), 2.01 (s, 3H); [M+H]$^+$ 414.8; Elemental Analysis for $C_{15}H_{18}N_4O_8S$: calc'd: C, 43.48; H, 4.38; N, 13.52. found: C, 43.12; H, 4.36; N, 13.17.

Step 2: Preparation of 5-Amino-3-(3'-(R)-Methoxy-β-D-xylofuranosyl)-3H,6H-thiazolo[4,5-d]pyrimidin-2-one (137)

In a manner similar to Example 42, Step 2, 43 mg of the title compound 137 was generated in 29% yield as a white solid: $^1$H NMR (400 MHz, $d_6$-DMSO) δ 11.50 (br s, 1H), 6.98 (br s, 2H), 5.68 (d, J=5.5 Hz, 1H), 5.60 (d, J=7.8 Hz, 1H), 5.10 (m, 1H), 4.48 (m, 1H), 4.08 (m, 1H), 3.84 (m, 1H), 3.57 (m, 2H), 3.35 (s, 3H); [M+H]$^+$ 330.9; Elemental Analysis for $C_{11}H_{14}N_4O_6S.0.7H_2O.0.1$ iPrOH: calc'd: C, 38.89; H, 4.68; N, 16.06. found: C, 38.78; H, 4.30; N, 15.84.

Example 46

Preparation of 5-Amino-3-(3'-(R)-(2-methoxy-ethoxy), 2',5'-di-hydroxy-β-D-xylofuranosyl)-3H,6H-thiazolo[4,5-d]pyrimidin-2-one (139)

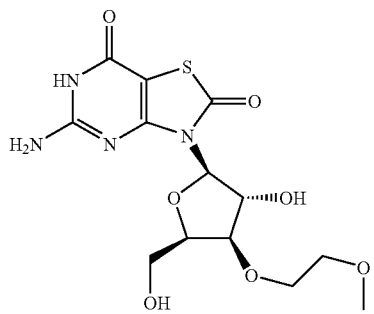

139

The required sugar, acetic acid 1,2,5-tri-O-acetyl-3-(2-methoxy-ethoxy)-D-xylofuranose α and β mixture (98) was prepared as reported in Example 32.

124

Step 1: Preparation of 5-Amino-3-(3'-(R)-(2-methoxy-ethoxy), 2',5'-di-O-acetyl-β-D-xylofuranosyl)-3H,6H-thiazolo[4,5-d]pyrimidin-2-one (138)

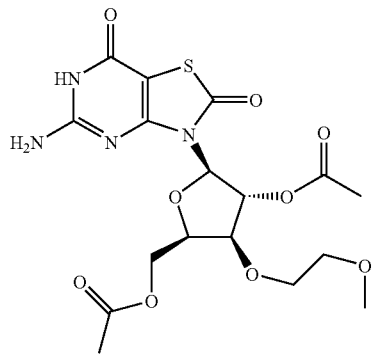

138

In a manner similar to Example 42, Step 1, 118 mg of the title compound 138 was generated from Acetic acid 1,2,5-tri-O-acetyl-3-(2-methoxy-ethoxy)-D-xylofuranose α and β mixture (98) in 21% yield as a white solid: $^1$H NMR (400 MHz, $d_6$-DMSO) δ 11.23 (s, 1H), 6.90 (br s, 2H), 6.13 (m, 1H), 5.74 (d, J=6.24 Hz, 1H), 4.33 (m, 3H), 4.17 (m, 1H), 3.73 (m, 1H), 3.57 (m, 1H), 3.46 (m, 2H), 3.25 (s, 3H), 2.03 (s, 3H), 2.01 (s, 3H); [M+H]$^+$ 459.3; Elemental Analysis for $C_{17}H_{22}N_4O_9S.0.3H_2O0.5EtOAc$: calc'd: C, 44.93; H, 5.28; N, 11.03. found: C, 44.93; H, 5.01; N, 11.14.

Step 2: Preparation of 5-Amino-3-(3'-(R)-(2-methoxy-ethoxy), 2',5'-di-hydroxy-β-D-xylofuranosyl)-3H,6H-thiazolo[4,5-d]pyrimidin-2-one (139)

In a manner similar to Example 42, Step 2, 43 mg of the title compound 139 was generated in 36% yield as a white solid: $^1$H NMR (400 MHz, $d_6$-DMSO) δ 11.44 (br s, 1H), 6.97 (br s, 2H), 5.67 (d, J=5.46 Hz, 1H), 5.60 (d, J=7.8 Hz, 1H), 5.10 (m, 1H), 4.39 (m, 1H), 4.08 (m, 1H), 3.98 (m, 1H), 3.71 (m, 1H), 3.59 (m, 3H), 3.45 (m, 2H), 3.27 (s, 3H); [M+H]$^+$ 374.9; Elemental Analysis for $C_{13}H_{18}N_4O_7S.1.0H_2O.0.25EtOAc$: calc'd: C, 40.57; H, 5.35; N, 13.52. found: C, 40.81; H, 4.96; N, 13.40.

Example 47

Preparation of 5-Amino-3-(3'-(S)-methyl, 2',3',5'-tri-hydroxy-β-D-xylofuranosyl)-3H,6H-thiazolo[4,5-d]pyrimidin-2-one (141)

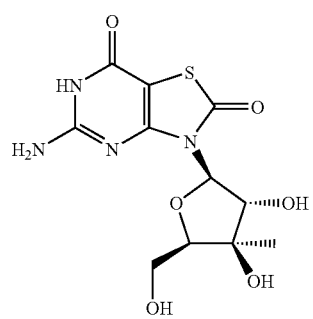

141

The preparation of the required sugar, 1,2,3,5 tetra-O-acetyl-3(S)-methyl D-xylofuranose α and β mixture (105), was prepared as reported in Example 34.

Step 1: Preparation of 5-Amino-3-(3'-(S)-methyl, 2',3',5'-tri-O-acetyl-β-D-xylofuranosyl)-3H,6H-thiazolo[4,5-d]pyrimidin-2-one (140)

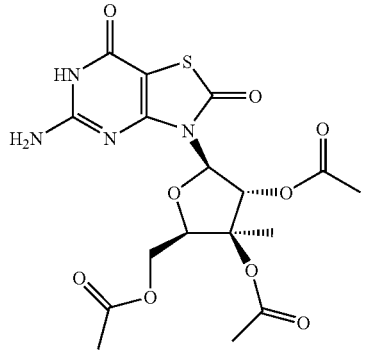

140

In a manner similar to Example 42, Step 1, 110 mg of the title compound 140 was generated from 1,2,3,5 tetra-O-acetyl-3(S)-methyl D-xylofuranose α and β mixture (105) in 15% yield as a white solid: $^1$H NMR (400 MHz, d$_6$-DMSO δ 11.27 (br s, 1H), 6.98 (br s, 2H), 6.25 (d, J=4.68 Hz, 1H), 5.77 (d, J=4.68 Hz, 1H), 4.40 (dd, J=9.4, 3.1 Hz, 1H), 4.22 (m, 1H), 3.68 (dd, J=4.7, 3.1 Hz, 1H), 2.08 (s, 3H), 2.04 (s, 3H), 2.02 (s, 3H), 1.56 (s, 3H); [M+H]$^+$ 456.8; Elemental Analysis for C$_{17}$H$_{20}$N$_4$O$_9$S.0.5H$_2$O0.2iPrOH: calc'd: C, 44.27; H, 4.77; N, 11.73. found: C, 44.45; H, 4.55; N, 11.62.

Step 2: Preparation of 5-Amino-3-(3'-(S)-methyl, 2',3',5'-tri-hydroxy-β-D-xylofuranosyl)-3H,6H-thiazolo[4,5-d]pyrimidin-2-one (141)

In a manner similar to Example 42, Step 2, 31 mg of the title compound 141 was generated in 54% yield as a white solid: $^1$H NMR (400 MHz, d$_6$-DMSO) δ 11.36 (br s, 1H), 6.94 (br s, 2H), 5.70 (d, J=5.46 Hz, 1H), 5.58 (d, J=4.7 Hz, 1H), 5.09 (br s, 1H), 4.48 (m, 2H), 3.59 (m, 3H), 1.17 (s, 3H); [M+H]$^+$ 330.9; Elemental Analysis for C$_{11}$H$_{14}$N$_4$O$_6$S.1.1H$_2$O: calc'd: C, 37.73; H, 4.66; N, 16.00. found: C, 37.66; H, 4.22; N, 15.60.

Example 48

Preparation of 5-Amino-3-(5'-(1,2-diacetoxy-ethyl), 2',3'-di-hydroxy-β-D-glucofuranosyl)-3H,6H-thiazolo[4,5-d]pyrimidin-2-one (143)

143

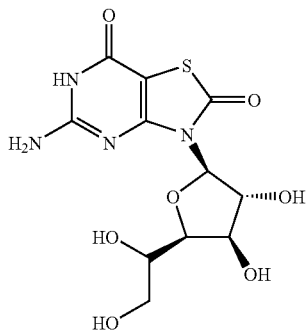

The required sugar, penta-O-acetylglucofuranose (108), was prepared as described in Example 35.

Step 1: Preparation of 5-Amino-3-(5'-(1,2-diacetoxy-ethyl), 2',3'-di-O-acetyl-β-D-glucofuranosyl)-3H,6H-thiazolo[4,5-d]pyrimidin-2-one (142)

142

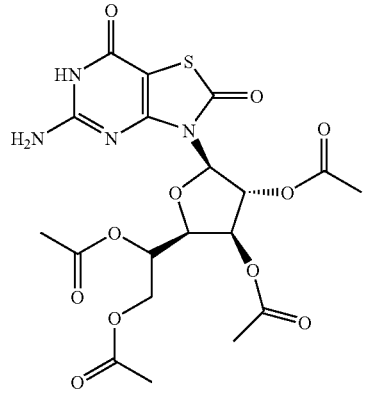

In a manner similar to Example 42, Step 1, 100 mg of the title compound 142 was generated from penta-O-acetylglucofuranose (108) in 10% yield as a white solid: $^1$H NMR (400 MHz, CDCl$_3$) δ 5.91 (m, 1H), 5.81 (br s, 2H), 5.73 (d, J=6.2 Hz, 1H), 5.51 (m, 1H), 5.41 (m, 1H), 4.55 (dd, J=12.5, 2.3 Hz, 1H), 4.29 (t, J=7.02 Hz, 1H), 3.90 (m, 1H), 1.96 (s, 3H), 1.93 (s, 3H), 1.90 (s, 3H), 1.55 (br s, 1H); [M+H]$^+$ 515.3; Elemental Analysis for C$_{19}$H$_{22}$N$_4$O$_{11}$S.0.15MeOH: calc'd: C, 44.29; H, 4.39; N, 10.79. found: C, 44.69; H, 4.44; N, 10.41.

Step 2: Preparation of 5-Amino-3-(5'-(1,2-diacetoxy-ethyl), 2',3'-di-hydroxy-β-D-glucofuranosyl)-3H,6H-thiazolo[4,5-d]pyrimidin-2-one (143)

In a manner similar to Example 42, Step 2, 45 mg of the title compound 143 was generated in 83% yield as a white solid: $^1$H NMR (400 MHz, d$_6$-DMSO) δ 11.34 (br s, 1H), 6.96 (br s, 2H), 5.72 (d, J=4.7 Hz, 1H), 5.63 (d, J=3.12 Hz, 1H), 5.11 (d, J=9.4 Hz, 1H), 4.56 (m, 2H), 4.39 (t, J=5.46 Hz, 1H), 3.96 (m, 1H), 3.74 (m, 2H), 3.51 (m, 1H), 3.36 (m, 1H); [M+H]$^+$ 346.9; Elemental Analysis for C$_{11}$H$_{14}$N$_4$O$_7$S.1.0H$_2$O: calc'd: C, 36.26; H, 4.43; N, 15.38. found: C, 36.20; H, 4.37; N, 15.01.

Example 49

Preparation of 5-Amino-3-(3'-(S)-acetoxymethyl-2', 3',5'-tri-O-acetyl-β-D-xylofuranosyl)-3H,6H-thiazolo[4,5-d]pyrimidin-2-one (144)

144

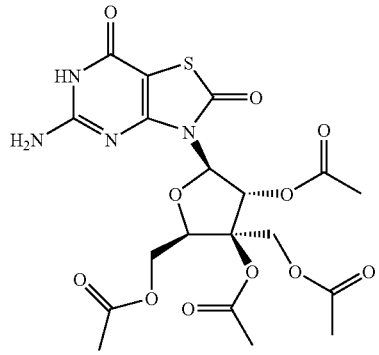

The required sugar, tetra-O-acetyl-3-acetoxymethyl-D-xylofuranos α and β mixture (113) was prepared as reported in Example 36.

Step 1: Preparation of 5-Amino-3-(3'-(S)-acetoxymethyl-2',3',5'-tri-O-acetyl-β-D-xylofuranosyl)-3H, 6H-thiazolo[4,5-d]pyrimidin-2-one (144)

In a manner similar to Example 42, Step 1, 80 mg of the title compound 144 was generated from tetra-O-acetyl-3-acetoxymethyl-D-xylofuranos α and β mixture (113) in 13% yield as a white solid: ¹H NMR (400 MHz, d₆-DMSO) δ 11.23 (s, 1H), 6.93 (br s, 2H), 6.37 (d, J=5.46 Hz, 1H), 5.69 (d, J=5.46 Hz, 1H), 4.77 (d, J=11.7 Hz, 1H), 4.52 (m, 3H), 4.39 (dd, J=7.8, 1.6 Hz, 1H), 4.17 (dd J=7.8, 3.9 Hz, 1H), 2.08 (s, 3H), 2.06 (s, 3H), 2.05 (s, 3H), 2.03 (s, 3H); [M+H]⁺ 514.8; Elemental Analysis for $C_{19}H_{22}N_4O_{11}S$: calc'd: C, 44.36; H, 4.31; N, 10.89. found: C, 44.16; H, 4.37; N, 10.69.

Example 50

Preparation of 5-Amino-3-(3'-(R)-Butoxy-β-D-xylofuranosyl)-3H,6H-thiazolo[4,5-d]pyrimidin-2-one (146)

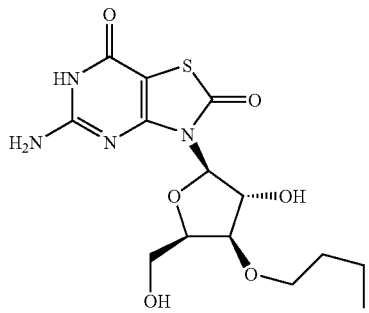

146

The required sugar acetic acid 1,2,5-tri-O-acetyl-3-butoxy-D-xylofuranose α and β mixture (101) was prepared as reported in Example 33.

Step 1: Preparation of 5-Amino-3-(3'-(R)-Butox-2', 5'-di-O-acetyl-β-D-xylofuranosyl)-3H,6H-thiazolo[4,5-d]pyrimidin-2-one (145)

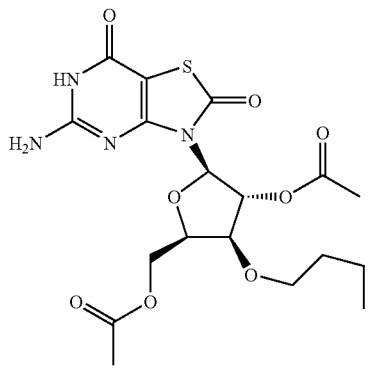

145

In a manner similar to Example 42, Step 1, the title compound 145 was generated from acetic acid 1,2,5-tri-O-acetyl-3-butoxy-D-xylofuranose α and β mixture (101) and carried on crude to Step 2.

Step 2: Preparation of 5-Amino-3-(3'-(R)-Butoxy-β-D-xylofuranosyl)-3H,6H-thiazolo[4,5-d]pyrimidin2-one (146)

In a manner similar to Example 42, Step 2, 5.3 mg of the title compound 146 was generated in 16% yield as a white solid: ¹H NMR (400 MHz, d₆-DMSO) δ 11.22 (br s, 1H), 6.92 (br s, 2H), 5.64 (d, J=5.46 Hz, 1H), 5.60 (d, J=7.8 Hz, 1H), 5.08 (m, 1H), 4.39 (t, J=6.24 Hz, 1H), 4.07 (m, 1H), 3.92 (t, J=7.02 Hz, 1H), 3.57 (m, 3H), 3.42 (m, 1H), 1.48 (m, 2H), 1.33 (m, 2H), 0.88 (t, J=7.02 Hz, 3H); [M+H]⁺ 372.9; Elemental Analysis for $C_{14}H_{20}N_4O_6S \cdot 1.0H_2O \cdot 0.4MeOH$: calc'd: C, 42.89; H, 5.90; N, 13.89. found: C, 43.18; H, 5.68; N, 13.65.

Example 51

Preparation of (3'S)-5-Amino-3-(3'-deoxy-3'-hydroxymethyl-β-D-ribofuranosyl)-3H,6H-thiazolo[4, 5-d]pyrimidin-2,7-dione (148)

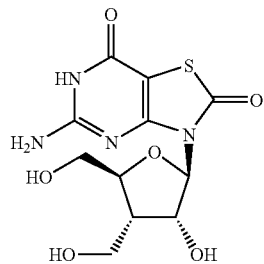

148

Step 1: Preparation of (3'S)-5-Amino-3-(3'-acetoxymethyl-2',5'-di-O-acetyl-3'-deoxy-β-D-ribofuranosyl)-3H,6H-thiazolo[4,5-d]pyrimidin-2,7-dione (147)

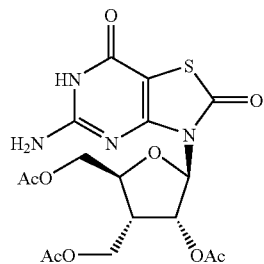

147

In a manner similar to Example 42, Step 1, 224 mg of the title compound 147 was generated from (3'S)-3-O-Acetoxymethyl-1,2,5-tri-O-acetyl-3-deoxy-α,β-D-ribofuranose [prepared according to the method of Cooperwood et al. *Nucleosides, Nucleotides, and Nucleic Acids* 2000, 19, 219-236 in which the enantiomer of the same compound was made] in 49% yield as an off-white solid: ¹H NMR (400 MHz, DMSO-d₆) δ 11.27 (s, 1H), 7.00 (s, 2H), 5.77 (m, 1H), 4.35 (dd, J=11.7, 2.3, 1H), 4.26 (m, 1H), 4.15 (m, 2H), 4.07 (m, 3H), 2.013 (s, 9H); [M+H]⁺ 457.3.

Step 2: Preparation of (3'S)-5-Amino-3-(3'-deoxy-3'-hydroxymethyl-β-D-ribofuranosyl)-3H,6H-thiazolo[4,5-d]pyrimidin-2,7-dione (148)

In a manner similar to Example 42, Step 2, 34 mg of the title compound 148 was generated in 58% yield as an off-white solid: $^1$H NMR (400 MHz, D$_2$O) δ 5.99 (m, 1H), 5.13 (m, 1H), 4.17 (m, 1H), 3.90 (m, 2H), 3.76 (m, 2H), 2.93 (m, 1H); [M+H]$^+$ 331.2; Elemental Analysis for C$_{11}$H$_{14}$N$_4$O$_6$S: calc'd: C, 35.20; H, 5.10; N, 14.93; S, 8.54. found: C, 35.17; H, 4.35; N, 14.73; S, 8.46.

Example 52

Preparation of 5-Amino-3-(5'-deoxy-5'-hydroxymethyl-β-D-ribofuranosyl)-3H,6H-thiazolo[4,5-d]pyrimidin-2,7-dione (150)

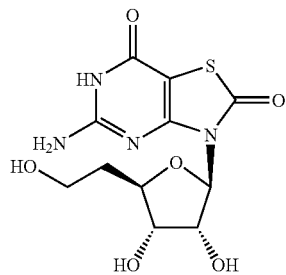

150

Step 1: Preparation of 5-Amino-3-(5'-O-acetoxymethyl-2',3'-di-O-acetyl-5'-deoxy-β-D-ribofuranosyl)-3H,6H-thiazolo[4,5-d]pyrimidin-2,7-dione (149)

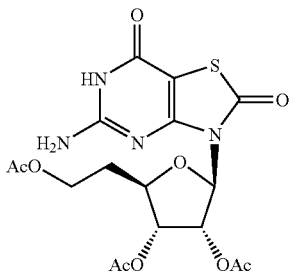

149

In a manner similar to Example 42, Step 1, 96 mg of the title compound 149 was generated from 5-O-acetoxymethyl-1,2,3-tri-O-acetyl-5-deoxy-α,β-D-ribofuranose [prepared according to the method of Pakulski et al. *Polish J. Chem.* 1995, 69, 912-917] in 34% yield as a white solid: $^1$H NMR (400 MHz, CDCl$_3$) δ 11.92 (s, 1H), 6.15 (d, J=6.4, 1H), 5.94 (s, 2H), 5.71 (m, 1H), 4.91 (m, 1H), 4.40 (m 1H), 4.16 (m, 2H), 2.09 (s, 9H), 2.00 (m, 2H); [M+H]$^+$ 457.0; Elemental Analysis for (C$_{17}$H$_{20}$N$_4$O$_9$S.0.25H$_2$O): calc'd: C, 44.30; H, 4.48; N, 12.16; S, 6.96. found: C, 44.79; H, 4.62; N, 11.55; S, 6.59.

Step 2: Preparation of 5-Amino-3-(5'-deoxy-5'-hydroxymethyl-β-D-ribofuranosyl)-3H,6H-thiazolo[4,5-d]pyrimidin-2,7-dione (150)

In a manner similar to Example 42, Step 2, 28 mg of the title compound 150 was generated in 56% yield as a white solid: $^1$H NMR (400 MHz, d$_6$-DMSO) δ 11.23 (s, 1H), 6.94 (s, 2H), 5.74 (m, 1H), 5.22 (m, 1H), 4.87 (m, 1H), 4.40 (m, 1H), 4.00 (m, 2H), 3.44 (s, 3H), 1.72 (m, 2H); [M+H]$^+$ 330.9.

Example 53

Preparation of 5-Amino-3-[3'-deoxy-3'-O-p-toluenesulfonyl-β-D-xylofuranosyl]-3H,6H-thiazolo-[4,5-d]pyrimidine-2,7-dione (151)

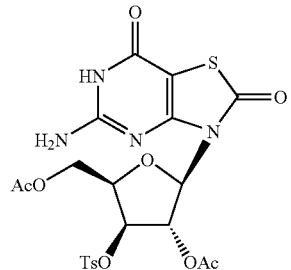

151

Step 1: Preparation of 5-Amino-3-[2'5'-di-O-acetyl-3'-deoxy-3'-O-p-toluenesulfonyl-β-D-xylofuranosyl]-3H,6H-thiazolo-[4,5-d]pyrimidine-2,7-dione (151)

In a manner similar to Example 42, Step 1, 24.6 mg of the title compound 151 was generated in 12% yield as an off-white solid: $^1$H NMR (400 MHz, CDCl$_3$) δ 11.89 (s, 1H), 7.84 (d, J=8.4, 2H), 7.40 (d, J=8.4, 2H), 6.22 (d, J=4.4, 1H), 5.92 (br s, 2H), 5.75 (d, J=4.8, 1H), 4.95 (d, J=4.8, 1H), 4.30 (m, 1H), 4.25 (d, J=6, 2H), 2.48 (s, 3H), 2.05 (s, 6H); [M+H]$^+$ 555.3.

Example 54

Preparation of (3'R)-5-Amino-3-(3'-deoxy-3'-fluoro-β-D-xylofuranosyl)-3H,6H-thiazolo[4,5-d]pyrimidin-2,7-dione (153)

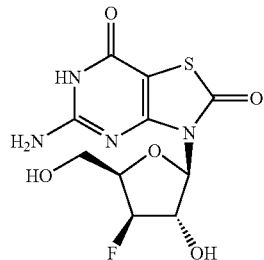

153

Step 1: Preparation of (3'R)-5-Amino-3-(2'-O-acetyl-5'-O-benzoyl-3'-deoxy-3'-fluoro-β-D-xylofuranosyl)-3H,6H-thiazolo[4,5-d]pyrimidin-2,7-dione (152)

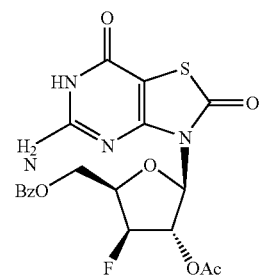

152

In a manner similar to Example 42, Step 1, 149 mg of the title compound 152 was generated from 1,2-Di-O-acetyl-5-

O-benzoyl-3-deoxy-3-(R)-fluoro-α,β-D-xylofuranose [prepared according to the method of Gosselin et al. *Carbohydrate Research* 1993, 249, 1-17] in 24% yield as a yellow solid: $^1$H NMR (400 MHz, CDCl$_3$) δ 11.57 (s, 1H), 8.04 (d, J=6.8, 2H), 7.56 (t, J=7.6, 1H), 7.43 (t, J=7.6, 2H), 6.35 (dd, J=22.4, 4.8, 1H), 5.92 (s, 2H), 5.32 (dd, J=51.6, 4.8, 1H), 5.20 (s, 1H), 4.79 (dd, J=11.2, 4, 1H), 4.59 (m, 2H), 4.5 (m, 1H), 2.06 (s, 3H); [M+H]$^+$ 465.3.

Step 2: (3'R)-5-amino-3-(3'-deoxy-3'-fluoro-β-D-xylofuranosyl)-3H,6H-thiazolo[4,5-d]pyrimidin-2,7-dione (153)

In a manner similar to Example 42, Step 2, 14.3 mg of the title compound 153 was generated in 45% yield as white solid: $^1$H NMR (400 MHz, DMSO-d$_6$) δ 11.41 (s, 1H), 6.97 (s, 2H), 5.77 (m, 1H), 5.19 (m, 1H), 4.98 (m, 1H), 4.01 (m, 1H), 3.60 (m, 2H), 2.09 (s, 2H); [M+H]$^+$ 318.9; Elemental analysis for (C$_{10}$H$_{11}$FN$_4$O$_5$S.0.4EA.2H$_2$O): calc'd: C, 35.76; H, 4.71; N, 14.3. found: C, 35.71; H, 3.68; N, 14.15.

Example 55

Preparation of 3-Allyl-5-amino-3H,6H-thiazolo[4,5-d]pyrimidine-2,7-dione (154)

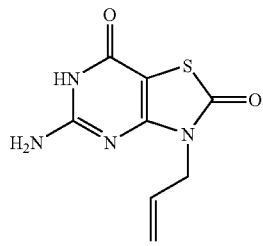

154

Step 1: Preparation of 3-Allyl-5-amino-3H,6H-thiazolo[4,5-d]pyrimidine-2,7-dione (154)

In a manner similar to Example 15, Step 1, scheme1, 178 mg of the title compound 154 was generated in 35% yield as a pale yellow solid: $^1$H NMR (400 MHz, DMSO-d$_6$) δ 10.26 (s, 1H), 6.09 (s, 2H), 5.06-5.01 (m, 1H), 4.32 (dd, J=10.3, 1.5, 1H), 4.196 (dd, J=16.9, 1.5, 1H), 3.55 (d, J=4.4, 2H); [M+H]$^+$ 225.1.

Example 56

Preparation of 5-Amino-3-pyridin-3-ylmethyl-3H, 6H-thiazolo[4,5-d]pyrimidine-2,7-dione (155)

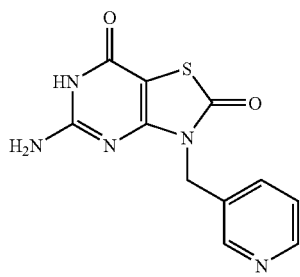

155

Step 1: Preparation of 5-Amino-3-pyridin-3-ylmethyl-3H,6H-thiazolo[4,5-d]pyrimidine-2,7-dione (155)

In a manner similar to Example 15, Step 1, 143 mg of the title compound 155 was generated in 24% yield as a white solid: $^1$H NMR (400 MHz, DMSO-d$_6$) δ 10.33 (s, 1H), 7.76 (d, J=2.2, 1H), 7.68 (dd, J=2.2, 1.5, 1H), 6.88 (m, 1H), 6.55 (s, 2H), 6.15 (s, 2H), 4.17 (s, 2H); [M+H]$^+$ 276.1.

Example 57

Preparation of 5-Amino-3-(4-chloro-but-2-enyl)-3H, 6H-thiazolo[4,5-d]pyrimidine-2,7-dione (156)

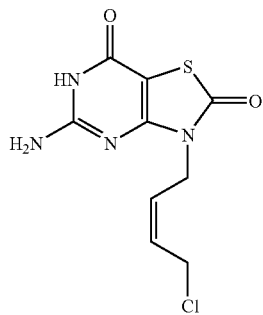

156

Step 1: Preparation of 5-Amino-3-(4-chloro-but-2-enyl)-3H,6H-thiazolo[4,5-d]pyrimidine-2,7-dione (156)

In a manner similar to Example 15, Step 1, 440 mg of the title compound 156 was generated in a 63% yield as a light yellow solid: $^1$H NMR (400 MHz, DMSO-d$_6$) δ 10.33 (s, 1H), 6.90 (s, 2H), 5.82-5.74 (m, 1H), 5.65-5.59 (m, 1H), 4.45 (d, J=7.0, 2H), 4.39 (d, J=7.8, 2H); [M+H]$^+$ 273.1.

Example 58

Preparation of 5-Amino-3-hexyl-3H-thiazolo[4, 5-d]pyrimidine-2,7-dione (157)

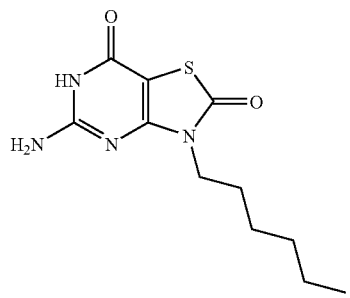

157

Step 1: Preparation of 5-Amino-3-hexyl-3H,6H-thiazolo[4,5-d]pyrimidine-2,7-dione (157)

In a manner similar to Example 15, Step 1, 154 mg of the title compound 157 was generated in a 35% yield as an off-white solid: $^1$H NMR (400 MHz, DMSO-d$_6$) δ 11.03 (s, 1H), 6.88 (s, 2H), 3.74 (t, J=6.8, 2H), 1.61 (m, 4H), 1.26 (m, 4H), 0.85 (t, J=6.8, 3H); [M+H]$^+$269.31.

Scheme X

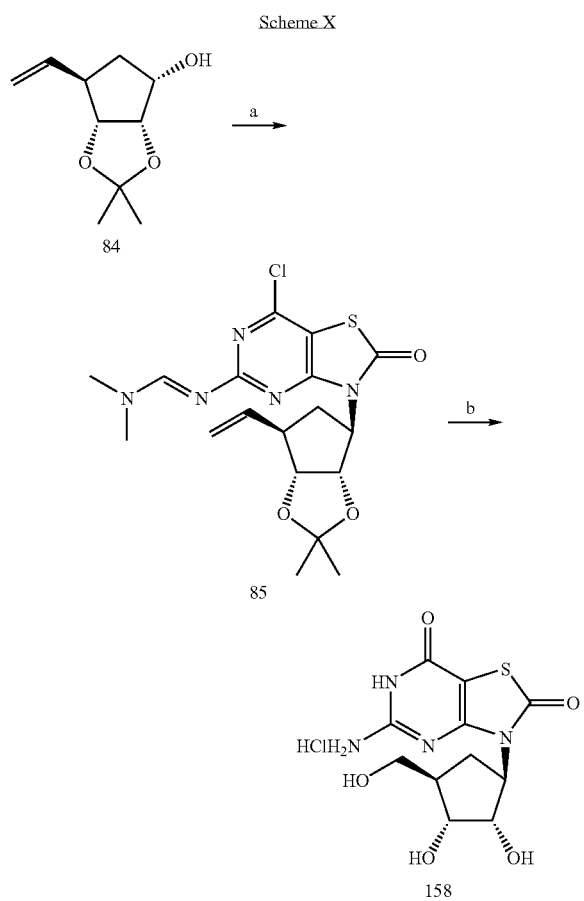

a) Tf₂O, py, CH₂Cl₂, 0° C., Chloroamidine base, NaH, CH₃CN, rt, 50° C., 12 h
b) NaIO₄, OsO₄, CH₃OH/H₂O, 0° C., 1 h-rt, 2 h; NaBH₄, CH₃OH, rt, 1 h; 2M HCl, CH₃OH, reflux, 5 h

Example 59

Preparation of (1'R,2'S,3'R,4'R)-5-Amino-3-(2',3'-dioxy-4'-hydroxymethyl-cyclopentan-1'-yl)-3H,6H-thiazolo[4,5-d]pyrimidine-2,7-dione (158)

(1'R,2'S,3'R,4'R)—N'-[7-chloro-2-oxo-3-(2',3'-O-isopropylidene-4'-vinyl-cyclopentan-1'-yl)-2,3-dihydro-thiozolo[4,5-d]pyrimidin-5-yl]-N,N-dimethyl-formamidine (85) (85 mg, 0.20 mmol) was dissolved in CH₃OH (3.0 mL) and H₂O (1.5 mL) at ambient temperature. The solution was cooled to 0° C. Sodium periodate (90 mg, 0.42 mmol) and Osmium tetroxide (2 mg, catalytic) were then added to the solution. The reaction was stirred at 0° C. for 1 h and room temperature for 2 h before it was filtered and concentrated. The resulting mixture was dissolved in CH₂Cl₂ (10 mL), then washed with H₂O (2×10 mL). The organic layer was dried over MgSO₄, filtered, then concentrated.

The above product was dissolved in CH₃OH (3 mL) at ambient temperature. Sodium borohydride (12 mg, 0.32 mmol) was then added to the solution. The reaction was stirred for 1 h, then concentrated. The resulting mixture was dissolved in CH₂Cl₂, and washed with H₂O (2×10 mL). The organic layer was dried over MgSO₄, filtered, then concentrated.

The above product was dissolved CH₃OH (1 mL) and 2 M HCl (5 mL) at ambient temperature. The reaction was stirred at reflux for 5 h, then concentrated. The resulting mixture was purified by reverse phase HPLC affording 9.1 mg (13%) of 158 as a white solid: ¹H (400 MHz, CD₃OD) δ 4.95 (m, 1H), 4.69 (dd, J=7.2, 5.6, 1H), 4.03 (t, J=5.2, 1H), 3.71 (dd, J=11.2, 6.4, 1H), 3.60 (dd, J=11.2, 6.4, 1H), 3.35 (s, 1H), 1.93-2.14 (m, 3H).

Example 60

5-Amino-3-(2'-O-acetyl-3'-deoxy-β-D-ribofuranosyl)-3H,6H-thiazolo[4,5-d]pyrimidine-2,7-dione (160)

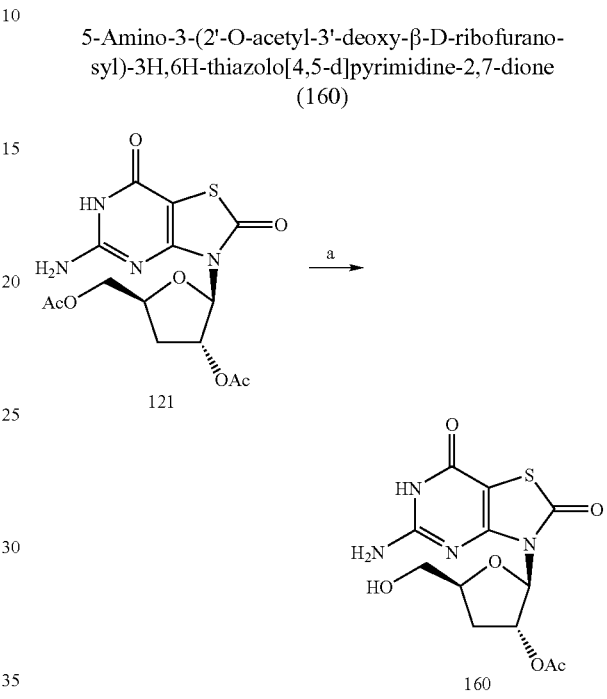

a. Candida Arctica, acetone, pH 7 phosphate buffer, 97%.

Preparation of 5-Amino-3-(2'-O-acetyl-3'-deoxy-β-D-ribofuranosyl)-3H,6H-thiazolo[4,5-d]pyrimidine-2,7-dione (160)

To a suspension of nucleoside diacetate 121 (200.0 mg, 0.52 mmol) in acetone (5.0 mL), pH 7 phosphate buffer (2.5 mL), and H₂O (22.5 mL) was added *Candida Arctica* immobilized acrylic resin (0.10 g). The mixture decolorized within min after enzyme addition. The reaction was stirred at room temperature for 16 h. Celite (1.0 g) was added and, after stirring for 10 min, the mixture was filtered through a pad of celite. The filter cake was rinsed with acetone (3×10 mL), and the acetone was reduced in vacuo. The remaining aqeous layer was then heavily salted with solid NaCl. Ethyl acetate was added the biphasic mixture was vigorously stirred for 30 min before separating. The organic layer was dried over Na₂SO₄, decanted, concentrated, and purified via flash chromatography (SiO₂, 50-100% EtOAc-hexanes+2% MeOH). This afforded 155.0 mg of monoacetate 160 (97%): ¹H (400 MHz, DMSO-d₆) δ 11.20 (s, 1H), 6.94 (br s, 2H), 5.79 (d, J=2.4, 1H), 5.63 (d, J=8.0, 1H), 4.76 (t, J=6.0, 1H), 4.11 (dt, J=5.2, 10.4, 1H), 3.43-3.52 (m, 2H), 2.44-2.5 (m, 1H), 2.05 (s, 3H), 1.95 (dd, J=6.0, 13.6, 1H); [M+H]⁺ m/z 342. Analysis cal'd for: C₁₂H₁₄N₄O₆S.0.5H₂O: C, 42.10; H, 4.12; N, 16.37; S, 9.37. Found: C, 42.30; H, 4.26; N, 16.37; S, 9.23.

Example 61

5-Amino-3-(2',3'-dideoxy-β-D-ribofuranosyl)-3H,6H-thiazolo[4,5-d]pyrimidine-2,7-dione (165)

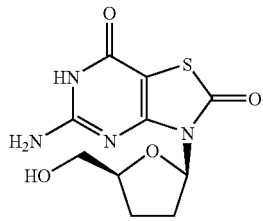

Step 1) Preparation of 5-N-Acetylamino-3-(5'-tert-butyldimethylsily-2'-deoxy-2'-O-thiocarbonylimidazole-β-D-ribofuranosyl)-3H,6H-thiazolo[4,5-d]pyrimidine-2,7-dione (161)

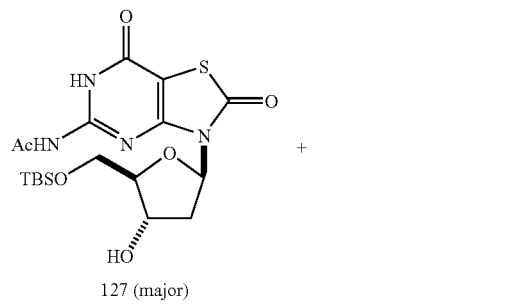

127 (major)

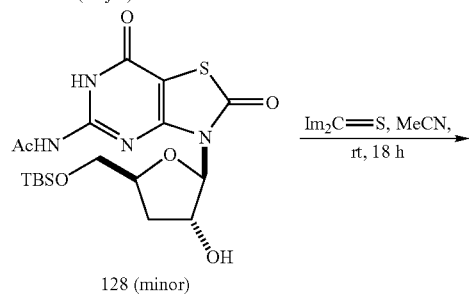

128 (minor)

Im₂C=S, MeCN, rt, 18 h →

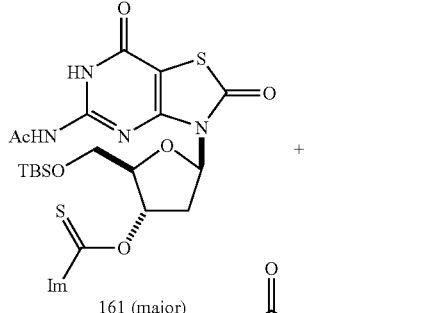

161 (major)

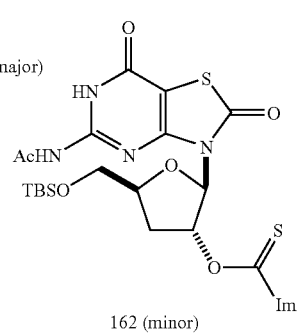

162 (minor)

To a mixture of alcohols 127 and 128 (247 mg, 0.541 mmol) in MeCN (8 mL) at rt was added TCDI (193 mg, 1.08 mmol). The reaction mixture was stirred 18 h whereupon it was concentrated and submitted to flash chromatography (SiO₂, EtOAc), affording 150 mg (49%) of a mixture of thiocarbamates 161 and 162 as a solid material: ¹H NMR (400 MHz, d₆-DMSO) δ 12.18 (br s, 1H), 11.72 (br s, 1H), 8.54 (s, 1H), 7.86 (s, 1H), 7.10 (s, 1H), 6.36 (m, 1H), 6.04 (s, 1H), 4.38-4.43 (m, 1H), 3.68-3.80 (m, 2H), 2.63-2.69 (br m, 1H), 2.36-2.41 (m, 1H), 2.17 (s, 3H), 0.84 (s, 9H), 0.00 (s, 6H); [M+H]⁺ m/z 567.

Step 2) Preparation of 5-N-Acetylamino-3-(5'-tert-butyldimethylsily-2',3'-dideoxy-β-D-ribofuranosyl)-3H,6H-thiazolo[4,5-d]pyrimidine-2,7-dione (163)

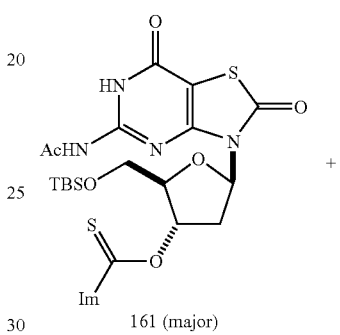

161 (major)

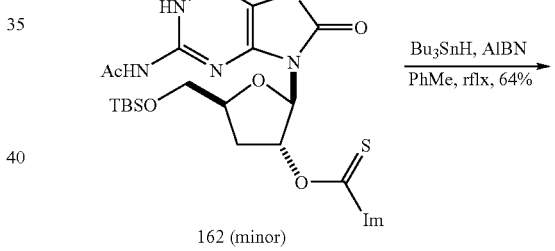

162 (minor)

Bu₃SnH, AIBN
―――――――→
PhMe, rflx, 64%

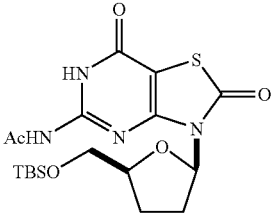

163

To a mixture of thiocarbamates 161 and 162 (57 mg, 0.10 mmol) and Bu₃SnH (187 uL, 0.705 mmol) in PhMe (10 mL) at rt was added AIBN (1.6 mg, 0.010 mmol). The reaction mixture was immersed into a 130° C. oil bath, stirred 20 min, concentrated and then submitted to flash chromatography (SiO₂, 60-80% EtOAc—CHCl₃), affording 28 mg (64%) of compound 163 as a white solid: ¹H NMR (400 MHz, d₆-DMSO) δ 12.13 (br s, 1H), 11.80 (br s, 1H), 6.11 (dd, J=8.4, 3.7, 1H), 3.95-4.02 (m, 1H), 3.64 (d, J=5.1, 2H), 2.54-2.59 (m, 1H), 2.23-2.33 (m, 1H), 2.19 (s, 3H), 2.04-2.13 (m, 1H), 1.94-1.97 (m, 1H), 0.82 (s, 9H), −0.01 (6H); [M+H]⁺ m/z 441.

Step 3) Preparation of 5-N-Acetylamino-3-(2',3'-dideoxy-β-D-ribofuranosyl)-3H,6H-thiazolo[4,5-d]pyrimidine-2,7-dione (164)

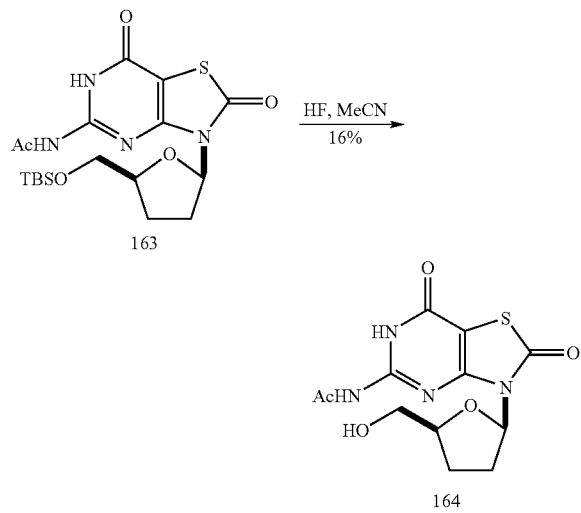

A solution of siloxane 163 (84 mg, 0.19 mmol) in 2 M HF—MeCN (20 mL) was stirred for 10 min, then concentrated and submitted to flash chromatography (SiO$_2$, 5-10% MeOH—CHCl$_3$) to afford 10 mg (16%) of alcohol 164 as a white solid: $^1$H NMR (400 MHz, d$_6$-DMSO) δ 12.15 (br s, 1H), 11.78 (br s, 1H), 6.10 (dd, J=8.4, 4.0, 1H), 4.66 (t, J=5.9, 1H), 3.91-3.97 (m, 1H), 3.46 (t, J=5.9, 2H), 2.51-2.58 (m, 1H), 2.21-2.32 (m, 1H), 2.19 (s, 3H), 2.01-2.18 (m, 1H), 1.89-1.97 (m, 1H); [M+H]$^+$ m/z 327.

Step 4) Preparation of 5-Amino-3-(2',3'-dideoxy-β-D-ribofuranosyl)-3H,6H-thiazolo[4,5-d]pyrimidine-2,7-dione (165)

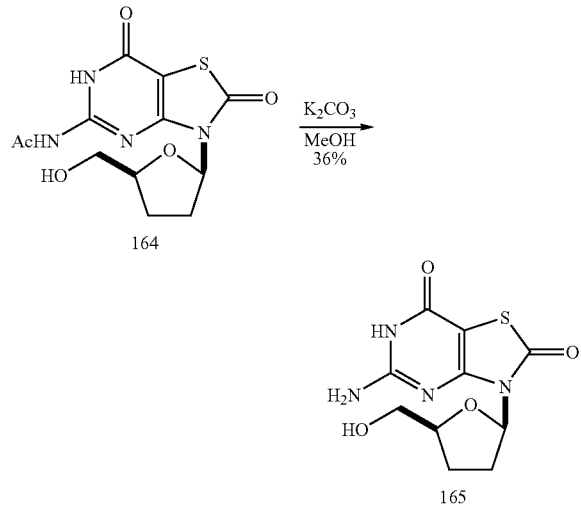

To a solution of acetamide 164 (19 mg, 0.058 mmol) in MeOH (3 mL) at rt was added K$_2$CO$_3$ (64 mg, 0.46 mmol). The reaction mixture was stirred 18 h whereupon it was quenched with HOAc (53 uL), concentrated and triturated with MeOH—H$_2$O to afford 6 mg (36%) of the title compound 165 as a white solid: $^1$H NMR (400 MHz, d$_6$-DMSO) δ 11.15 (s, 1H), 6.85 (br s, 2H), 6.07 (dd, J=8.4, 4.4, 1H), 4.63 (t, J=5.9, 1H), 3.89-3.95 (m, 1H), 3.46 (t, J=5.5, 2H), 2.44-2.48 (m, 1H), 2.17-2.27 (m, 1H), 2.01-2.11 (m, 1H), 1.86-1.93 (m, 1H); [M+H]$^+$ m/z 285.

Anti-Viral Activity of Compounds

A number of assays may be employed in accordance with the present invention in order to determine the degree of anti-viral activity of a compound of the invention such as cell culture, animal models, and administration to human subjects. The assays described herein may be used to assay viral growth over time to determine the growth characteristics of a virus in the presence of a compound of the invention.

In another embodiment, a virus and a compound of the invention are administered to animal subjects susceptible to infection with the virus. The incidence, severity, length, virus load, mortality rate of infection, etc. can be compared to the incidence, severity, length, virus load, mortality rate of infection, etc. observed when subjects are administered the virus alone (in the absence of a compound of the invention). Anti-virus activity of the compound of the invention is demonstrated by a decrease in incidence, severity, length, virus load, mortality rate of infection, etc. in the presence of the compound of the invention. In a specific embodiment, the virus and the compound of the invention are administered to the animal subject at the same time. In another specific embodiment, the virus is administered to the animal subject before the compound of the invention. In another specific embodiment, the compound of the invention is administered to the animal subject before the virus.

In another embodiment, the growth rate of the virus can be tested by sampling biological fluids/clinical samples (e.g., nasal aspirate, throat swab, sputum, broncho-alveolar lavage, urine, saliva, blood, or serum) from human or animal subjects at multiple time points post-infection either in the presence or absence of a compound of the invention and measuring levels of virus. In specific embodiments, the growth rate of a virus is assayed by assessing the presence of virus in a sample after growth in cell culture, growth on a permissible growth medium, or growth in subject using any method well-known in the art, for example, but not limited to, immunoassay (e.g., ELISA; for discussion regarding ELISAs see, e.g., Ausubel et al., eds, 1994, Current Protocols in Molecular Biology, Vol. I, John Wiley & Sons, Inc., New York at 11.2.1), immunofluorescent staining, or immunoblot analysis using an antibody which immunospecifically recognizes the virus to be assayed or detection of a virus-specific nucleic acid (e.g., by Southern blot or RT-PCR analysis, etc.).

In a specific embodiment, viral titers can be determined by obtaining biological fluids/clinical samples from infected cells or an infected subject, preparing a serial dilution of the sample and infecting a monolayer of cells that are susceptible to infection with the virus (e.g. primary cells, transformed cell lines, patient tissue samples, etc) at a dilution of the virus that allows for the emergence of single plaques. The plaques can then be counted and the viral titer expressed as plaque forming units per milliliter of sample.

In one specific embodiment, the growth rate of a virus in a subject can be estimated by the titer of antibodies against the virus in the subject. Antibody serum titer can be determined by any method well-known in the art, for example, but not limited to, the amount of antibody or antibody fragment in serum samples can be quantitated by, e.g., ELISA. Additionally, in vivo activity of a Formula I compound can be determined by directly administering the compound to a test animal, collecting biological fluids (e.g., nasal aspirate, throat swab, sputum, broncho-alveolar lavage, urine, saliva, blood, or serum) and testing the fluid for anti-virus activity.

In embodiments where samples to be assayed for virus levels are biological fluids/clinical samples (e.g., nasal aspirate, throat swab, sputum, broncho-alveolar lavage, urine, saliva, blood, or serum), the samples may or may not contain in tact cells. Samples from subjects containing intact cells can be directly processed, whereas isolates without intact cells may or may not be first cultured on a permissive cell line (e.g. primary cells, transformed cell lines, patient tissue samples, etc) or growth medium (e.g., LB broth/agar, YT broth/agar, blood agar, etc.). Cell suspensions can be cleared by centrifugation at, e.g., 300×g for 5 minutes at room temperature, followed by a PBS, pH 7.4 ($Ca^{++}$ and $Mg^{++}$ free) wash under the same conditions. Cell pellets can be resuspended in a small volume of PBS for analysis. Primary clinical isolates containing intact cells can be mixed with PBS and centrifuged at 300×g for 5 minutes at room temperature. Mucus is removed from the interface with a sterile pipette tip and cell pellets can be washed once more with PBS under the same conditions. Pellets can then be resuspended in a small volume of PBS for analysis.

In another embodiment, a compound of the invention is administered to a human subject infected with a virus. The incidence, severity, length, viral load, mortality rate of infection, etc. can be compared to the incidence, severity, length, viral load, mortality rate of infection, etc. observed in human subjects infected with a virus in the absence of a compound of the invention or in the presence of a placebo. Anti-viral activity of the compound of the invention is demonstrated by a decrease in incidence, severity, length, viral load, mortality rate of infection, etc. in the presence of the compound of the invention. Any method known in the art can be used to determine anti-viral activity in a subject such as those described previously.

Additionally, in vivo activity of a Formula I prodrug can be determined by directly administering the compound to an animal or human subject, collecting biological fluids/clinical samples (e.g., nasal aspirate, throat swab, sputum, broncho-alveolar lavage, urine, saliva, blood, or serum) and testing the biological fluids/clinical samples for anti-viral activity (e.g., by addition to cells in culture in the presence of the virus).

Metabolism of Formula I Prodrugs

The Formula I prodrugs of the present invention must be metabolized to Formula II compounds and other compounds of the invention in the body if they are to serve as effective prodrugs. Hepatocyes often are used to assess the degree to which a compound may be transformed in the body of an animal, and it is known that such transformations may vary with hepatocytes from different species in a way that reflects metabolism in the whole animal. See Seddon T. et al., *Biochem Pharmacol.*, 38(10), 1657-65 (1989).

A study was undertaken to evaluate the metabolic stability of Formula I compounds 14, 15, 13, 114, 30, 103, 67, 65, and 76 in the presence of fresh cynomolgus monkey hepatocytes and monitor the formation of 6-oxy metabolites, i.e., Formula II compounds and other compounds of the invention. For comparison, the metabolic stability of famciclovir was also assessed.

Preparation of Fresh Hepatocyte Suspension

Fresh cynomolgus monkey hepatocyte suspension (Lot #: Cy141) was purchased from CellzDirect (Tucson, Ariz.). Hepatocyte Incubation Medium (serum-free, sterile) was purchased from In Vitro Technologies (Baltimore, Md.).

The cynomolgus monkey hepatocyte suspension was prepared from fresh cynomolgus monkey hepatocytes in hepatocyte incubation medium at the concentration of 1.25 million cells/mL. The final incubation concentration (after test article addition) was 1.0 million cells/mL.

Preparation of Stock Solutions

Existing 100 mM stock solutions in DMSO were used. The concentrations of the test articles were checked using UV-vis microplate reader. Correction coefficients were determined using the absorbance of a freshly prepared DMSO stock of 122.

Incubations

Reaction suspensions were prepared in removable 96-well tubes, each containing 320 µL of fresh cynomolgus monkey hepatocyte suspension at the density of 1.25 million cells per mL and 40 µL of hepatocyte incubation medium. The above mixtures were pre-incubated open at 37° C., 95% humidity and 5% $CO_2$ for 30 minutes. Reactions were initiated by the addition of 40 µL of test article at 10× concentration to each tube to achieve the final concentrations of 50 µM for the test article(s) and 1 million/mL cell density. The reaction suspension in each tube was mixed by inverting the tube several times. Aliquots of 50 µL from each reaction suspension were distributed into six additional removable 96-well tubes (one tube per time point taken at 15, 30, 45, 60, 90, and 120 minutes). The open tubes were incubated at 37° C. under 95% humidity and 5% $CO_2$.

Preparation of Samples for Analysis

At predetermined time points, reactions were terminated by the addition of 150 µL of the stop solution to each tube containing 50 µL of the reaction suspension. The composition of the stop solution was the following: 15 mL of acetonitrile (containing 1 µg/mL nebularine as an internal standard and 0.1% formic acid) combined with 1 mL water.

The calibration curves were prepared in the following way. To 80 µL of cell suspension (at the cell density of 1.25 million/mL) 10 µL of hepatocyte incubation medium and 10 µL of the appropriate concentration of the compound in hepatocyte incubation medium were added. Immediately following the compound addition, 300 µL of the stop solution (see above) was added.

All quenched samples were kept on wet ice until they were processed for analysis. Then they were mixed using a bench top Multi-Tube Vortexer (VWR Scientific Products) for approximately 30 seconds, and centrifuged at 4,000 rpm (3,220 rcf) for 10 minutes at 4° C. Clear supernatant (100 µL) was transferred into a clean deep well 96-well plate, evaporated to dryness under nitrogen, reconstituted in 100 µL of 90:10 water:acetonitrile, and analyzed for the parent form and metabolites of the test article using an appropriate LC/MS/MS method.

Bioanalysis

The compounds were quantified on an API3000 LC/MS/MS instrument in the ESI-Positive MRM (multiple reaction monitoring) mode. The summary of the results of Formula I prodrug degradation and product generation is given in Table 1.

TABLE 1

Concentration of the Metabolized Product Formed in Cynomolgus Monkey Hepatocytes after 2 hrs Incubation of 50 µM of a Formula I Prodrug

| Formula I Compound | Metabolized Product | Product Concentration (µM) | Response |
|---|---|---|---|
| 14 | 122 | 9.7 | + |
| 15 | 122 | 31.8 | ++++ |
| 13 | 122 | 24.2 | +++ |

TABLE 1-continued

Concentration of the Metabolized Product Formed in Cynomolgus Monkey Hepatocytes after 2 hrs Incubation of 50 µM of a Formula I Prodrug

| Formula I Compound | Metabolized Product | Product Concentration (µM) | Response |
|---|---|---|---|
| 114 | 134 | 21.7 | +++ |
| 30 | 117 | 21.5 | +++ |
| 103 | 141 | 13.1 | ++ |
| 57 | 157 | 1.7 | + |
| 65 | 148 | 14.7 | ++ |
| 76 | 132 | 21.4 | +++ |
| Famciclovir | Penciclovir | 5.9 | + |

In fresh cynomolgus monkey hepatocytes compounds 14, 15, 13, 114, 30, 103, 67, 65, and 76 as well as famciclovir are metabolized to yield the corresponding 6-oxy metabolites: 122 from the first three Formula I prodrugs and 134, 117, 141, 157, 148, and 132, respectively. Famciclovir produces penciclovir.

IFN-α Induction from Peripheral Blood Mononuclear Cells (PBMC)

Peripheral blood mononuclear cells (PBMCs) are prepared by standard methods from human blood and are primarily comprised of monocytes, NK cells, circulating dendritic cells and both T and B cells. Briefly, they are purified by density gradient centrifugation from a buffy coat, which is the component of whole blood that contains leukocytes and platelets. In turn, buffy coats are prepared by centrifuging whole blood and isolating the thin cream colored layer between the upper plasma layer and the lower red blood cell portion of the separated mixture.

PBMC Purification

Freshly collected donor buffy coats were obtained from the San Diego Blood Bank. PBMCs were isolated from the buffy coats using histopaque-1077 gradient (Sigma), essentially as described in the manufacturer's protocol. Buffy coats were transferred into 50 ml centrifuge tubes and PBS added to a total volume of 35 ml. Next 10 ml histopaque-1077 was underlayed at the bottom of each tube, which were then centrifuged at 259×g for 30 minutes at room temperature without brake in a 5804 R centrifuge (Eppendorf). The top PBS level from each tube was removed and discarded and the buffy coat layer transferred to a fresh tube. The total volume was made up to 50 ml with PBS and the tubes were then centrifuged for 10 minutes at 259×g at room temperature. The cells were washed an additional 3 times with PBS in this manner.

The cell (PBMC) pellet was then resuspended in 30-40 ml complete (RPMI 1640) media. PBMCs were seeded at either 2.5 or 7.5×10$^6$ cells/ml complete media (1× and 3× seedings, respectively) and allowed to rest overnight before compound exposure for 24 hours. The cells and media were then collected, centrifuged for 5 minutes at 735×g in a 5415 C microfuge (Eppendorf) at room temperature and the supernatant analyzed by IFN-α ELISA. The ability of Formula I prodrugs, Formula II compounds, and other compounds of the invention to demonstrate favorable oral delivery characteristics and to induce immune responses when administered by a selected route can be compared with the results of similar experiments with compounds described in the literature. Hereby incorporated by reference in their entireties are U.S. Pat. Nos. 5,041,426 and 4,880,784, and U.S. patent application Ser. No. 10/861,430 (U.S. Patent Application Publication No. US 2005/0070556), which disclose, inter alia, IFN-α induction of isatoribine.

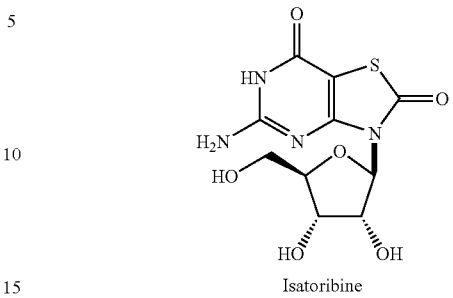

Isatoribine

Accordingly, relative activities of the compounds of the invention are expressed as a percentage of the level of IFN-α induction by either 32 or 100 µM isatoribine.

ELISA Protocol

Human IFN-α ELISA (#KHC4012) was performed as described in Biosource protocol. However, to ensure that readings were within the linear range of detection, PBMC supernatant samples were typically diluted 1:3 (2.5×10$^6$ cells/ml seeding) or 1:15 (7.5×10$^6$ cells/ml seeding) and then analyzed together with undiluted supernatant samples. The concentration in each sample was calculated from the O.D. by reference to a standard curve.

The compounds of the invention exhibited IFN-α induction from PBMCs relative to isatoribine in the following ranges:

0-10%: Compounds 142, 157, 141, 148, and 33
11-50%: Compounds 152 and 165
51-100%: Compounds 32, 160, 130, and 137
>100%: Compounds 133, 34, 147, 121, 122, 134, 117, 132, and 153.

Comparison to Isatoribine

Figure 2:
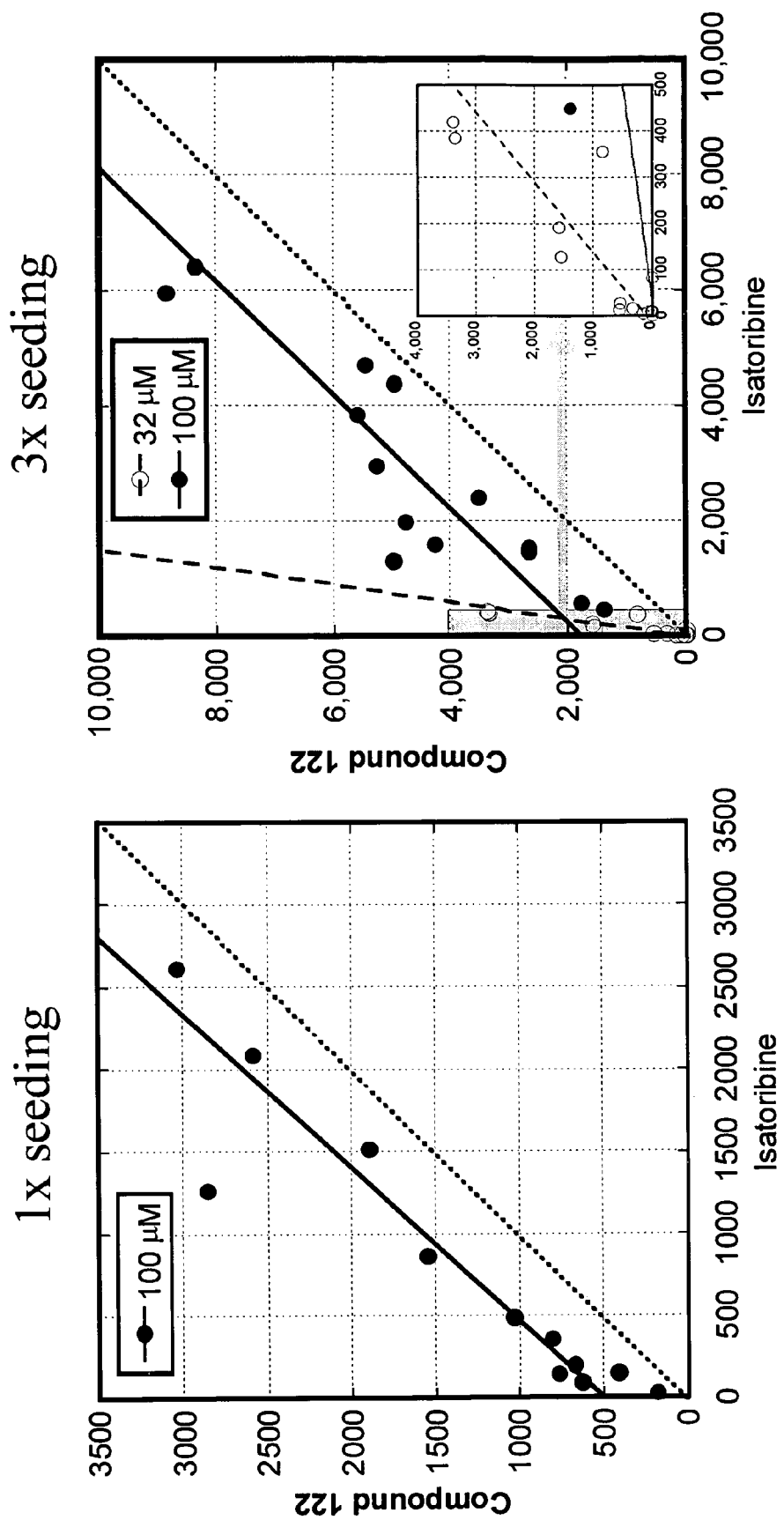
FIG. 2 shows a plot of pg/ml IFN-α induced in human PBMCs from compound 122 vs. pg/ml IFN-α induced by an identical concentration of isatoribine.

The results demonstrate the remarkable superiority of 134 and 122 to isatoribine with respect to enhancement of IFN-α production from human PBMCs in vitro. FIG. 1 and FIG. 2 show plots of pg/ml IFN-α induced in human PBMCs from compounds 134 and 122 vs pg/ml IFN-α induced by an identical concentration of isatoribine. The results may be summarized as follows.

At 1×PBMC seeding, both 134 and 122 induce significantly and substantially more IFN-α production at 100 µM test compound than does isatoribine, especially for weak responders to isatoribine (left panel on FIGS. 1 and 2). When seeding is increased to 3×, the difference between the amount of IFN-α produced at 100 µM test agent is less clear-cut although visually apparent and statistically significant (right panel, FIGS. 1 and 2). When the concentration of both 134 and 122 is 32 µM at 3× seeding, however, both 134 and 122 dramatically and unexpectedly outperform isatoribine (right panel and inserts of FIGS. 1 and 2).

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A compound selected from:

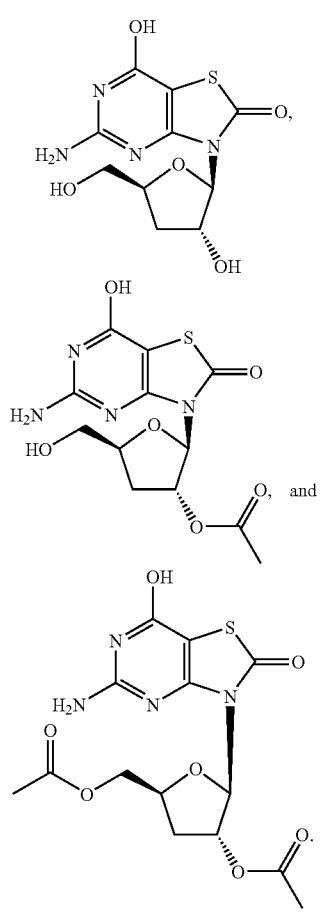

or a pharmaceutically acceptable salt or tautomer thereof.

2. A compound that is:

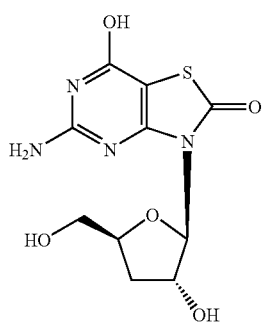

or a pharmaceutically acceptable salt or tautomer thereof.

3. A pharmaceutical composition comprising a pharmaceutically acceptable carrier and the compound according to claim 1.

4. A pharmaceutical composition comprising a pharmaceutically acceptable carrier and the compound according to claim 2.

5. A method of treating a hepatitis C virus infection comprising administering to a patient in need thereof a therapeutically effective amount of a compound according to claim 1.

6. A method of treating a hepatitis C virus infection comprising administering to a patient in need thereof a therapeutically effective amount of a compound according to claim 2.

7. A compound or pharmaceutically acceptable salt selected from the group consisting of

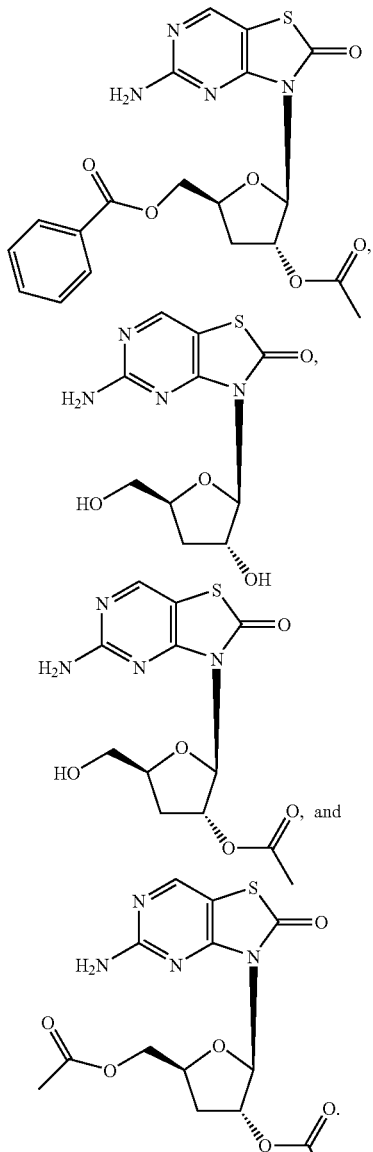

8. A pharmaceutical composition comprising a pharmaceutically acceptable carrier and a compound according to claim 7.

9. A method of treating a hepatitis C virus infection comprising administrating to a patient in need thereof a therapeutically effective amount of a compound according to claim 7.

10. A compound that is:

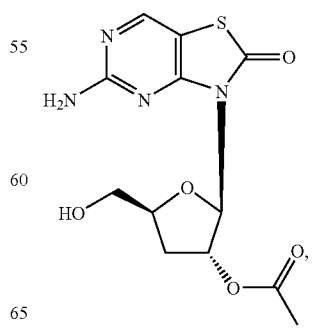

or a pharmaceutically acceptable salt thereof.

11. A pharmaceutical composition comprising a pharmaceutically acceptable carrier and a compound according to claim 10.

12. A method of treating hepatitis C virus infection comprising administrating to a patient in need thereof a therapeutically effective amount of a compound according to claim 10.

* * * * *